(12) United States Patent
Lonergan et al.

(10) Patent No.: US 11,459,309 B2
(45) Date of Patent: *Oct. 4, 2022

(54) CRYSTALLINE FORMS OF A LYSYL OXIDASE-LIKE 2 INHIBITOR AND METHODS OF MAKING

(71) Applicant: PHARMAKEA, INC., San Diego, CA (US)

(72) Inventors: David Lonergan, San Diego, CA (US); Kevin Ross Holme, San Diego, CA (US); Martin W. Rowbottom, San Diego, CA (US)

(73) Assignee: PHARMAKEA, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/983,759

(22) Filed: Aug. 3, 2020

(65) Prior Publication Data

US 2020/0361901 A1  Nov. 19, 2020

Related U.S. Application Data

(63) Continuation of application No. 16/331,095, filed as application No. PCT/US2017/050332 on Sep. 6, 2017, now Pat. No. 10,774,069.

(60) Provisional application No. 62/384,596, filed on Sep. 7, 2016.

(51) Int. Cl.
| | | |
|---|---|---|
| C07D 401/12 | (2006.01) | |
| C07D 207/12 | (2006.01) | |
| A61K 31/4439 | (2006.01) | |
| C07C 309/66 | (2006.01) | |

(52) U.S. Cl.
CPC ........ *C07D 401/12* (2013.01); *A61K 31/4439* (2013.01); *C07C 309/66* (2013.01); *C07D 207/12* (2013.01); *C07B 2200/13* (2013.01)

(58) Field of Classification Search
CPC .................................................. C07D 401/12
USPC .................................................... 546/276.4
See application file for complete search history.

(56) References Cited

U.S. PATENT DOCUMENTS

| | | | |
|---|---|---|---|
| 4,229,447 A | 10/1980 | Porter | |
| 4,596,795 A | 6/1986 | Pitha | |
| 4,755,386 A | 7/1988 | Hsiao et al. | |
| 5,021,456 A | 6/1991 | Palfreyman et al. | |
| 5,739,136 A | 4/1998 | Ellinwood, Jr. et al. | |
| 6,878,714 B2 | 4/2005 | Askew et al. | |
| 6,956,047 B1 | 10/2005 | Chen | |
| 6,995,162 B2 | 2/2006 | Chen et al. | |
| 7,060,697 B2 | 6/2006 | Marsilje et al. | |
| 7,067,664 B1 | 6/2006 | Chen | |
| 7,101,868 B2 | 9/2006 | Elbaum et al. | |
| 7,102,009 B2 | 9/2006 | Patel et al. | |
| 7,105,682 B2 | 9/2006 | Chen et al. | |
| 7,307,088 B2 | 12/2007 | Huang et al. | |
| 7,378,448 B2 | 5/2008 | Chappell et al. | |
| 7,381,750 B2 | 6/2008 | De La Torre et al. | |
| 7,482,340 B2 | 1/2009 | Otsomaa et al. | |
| 7,507,748 B2 | 3/2009 | Yuan et al. | |
| 7,514,564 B2 | 4/2009 | Chen et al. | |
| 7,687,643 B2 | 3/2010 | Askew et al. | |
| 7,723,331 B2 | 5/2010 | Giordanetto et al. | |
| 7,759,493 B2 | 7/2010 | Ge et al. | |
| 7,902,372 B2 | 3/2011 | Chappell et al. | |
| 8,058,445 B2 | 11/2011 | Chen et al. | |
| 8,247,430 B2 | 8/2012 | Yuan et al. | |
| 8,338,611 B2 | 12/2012 | Chappell et al. | |
| 8,343,944 B2 | 1/2013 | Xia et al. | |
| 8,642,624 B2 | 2/2014 | Chen et al. | |
| 10,150,732 B2 | 12/2018 | Rowbottom et al. | |
| 10,570,094 B2 | 2/2020 | Rowbottom et al. | |
| 10,766,860 B2 | 9/2020 | Rowbottom et al. | |
| 10,774,069 B2 * | 9/2020 | Lonergan | C07D 401/12 |
| 2002/0147198 A1 | 10/2002 | Chen et al. | |
| 2004/0087568 A1 | 5/2004 | Huang et al. | |
| 2005/0171086 A1 | 8/2005 | Brodney et al. | |
| 2006/0040966 A1 | 2/2006 | Yuan et al. | |
| 2007/0066658 A1 | 3/2007 | Chappell et al. | |
| 2007/0105866 A1 | 5/2007 | Hutchinson et al. | |
| 2007/0123522 A1 | 5/2007 | Hutchinson et al. | |
| 2007/0149579 A1 | 6/2007 | Blouin et al. | |
| 2007/0173508 A1 | 7/2007 | Hutchinson et al. | |
| 2007/0219206 A1 | 9/2007 | Hutchinson et al. | |

(Continued)

FOREIGN PATENT DOCUMENTS

| | | |
|---|---|---|
| EP | 0110405 A2 | 6/1984 |
| EP | 0706795 A2 | 4/1996 |

(Continued)

OTHER PUBLICATIONS

Allais et al. Metal-free multicomponent syntheses of pyridines. Chem Rev 114:10829-10868 (2014).
Ansel. Pharmaceutical Dosage Forms and Drug Delivery Systems 7th ed. (pp. 48-53) (1999).
Barr et al. American translation, modification, and validation of the St. George's Respiratory Questionnaire. Clin Ther. 22(9):1121-45 (2000).
Barry-Hamilton et al. Allosteric inhibition of lysyl oxidase-like-2 impedes the development of a pathologic microenvironment. Nat Med 16(9):1009-1017 (2010).

(Continued)

*Primary Examiner* — Nizal S Chandrakumar
(74) *Attorney, Agent, or Firm* — Maier & Maier, PLLC

(57) ABSTRACT

Described herein are crystalline forms of pharmaceutically acceptable salts of the lysyl oxidase-like 2 (LOXL2) inhibitor (3-(4-(aminomethyl)-6-(trifluoromethyl)pyridin-2-yloxy)phenyl)((3R,4R)-3-fluoro-4-hydroxypyrrolidin-1-yl)methanone. Also described are methods of making the LOXL2 inhibitor, pharmaceutical compositions and medicaments comprising the LOXL2 inhibitor, and methods of using the LOXL2 inhibitor in the treatment of conditions, diseases, or disorders associated with LOXL2 activity.

5 Claims, 12 Drawing Sheets

(56) References Cited

U.S. PATENT DOCUMENTS

| | | | |
|---|---|---|---|
| 2007/0225285 | A1 | 9/2007 | Hutchinson et al. |
| 2007/0270430 | A1 | 11/2007 | Ice et al. |
| 2008/0004269 | A1 | 1/2008 | Xu et al. |
| 2008/0027050 | A1 | 1/2008 | Terauchi et al. |
| 2008/0051405 | A1 | 2/2008 | Giordanetto et al. |
| 2008/0318926 | A1 | 12/2008 | Ice et al. |
| 2009/0143355 | A1 | 6/2009 | Yuan et al. |
| 2011/0076272 | A1 | 3/2011 | Smith et al. |
| 2011/0136763 | A1 | 6/2011 | Xia et al. |
| 2012/0149681 | A1 | 6/2012 | Rodgers et al. |
| 2014/0120102 | A1 | 5/2014 | Bornstein et al. |
| 2014/0302524 | A1 | 10/2014 | McCauley et al. |
| 2016/0222128 | A1 | 8/2016 | Neufeld et al. |
| 2019/0192495 | A1 | 6/2019 | Bain et al. |
| 2020/0115341 | A1 | 4/2020 | Rowbottom et al. |

FOREIGN PATENT DOCUMENTS

| | | |
|---|---|---|
| EP | 1775347 A2 | 4/2007 |
| WO | WO-9932117 A1 | 7/1999 |
| WO | WO-0153263 A1 | 7/2001 |
| WO | WO-2005090286 A1 | 9/2005 |
| WO | WO-2006053555 A2 | 5/2006 |
| WO | WO-2007016784 A1 | 2/2007 |
| WO | WO-2008009963 A2 | 1/2008 |
| WO | WO-2009017833 A2 | 2/2009 |
| WO | WO-2011017125 A1 | 2/2011 |
| WO | WO-2011109799 A1 | 9/2011 |
| WO | WO-2012068450 A1 | 5/2012 |
| WO | WO-2013026025 A1 | 2/2013 |
| WO | WO-2013059587 A1 | 4/2013 |
| WO | WO-2013161308 A1 | 10/2013 |
| WO | WO-2014070939 A1 | 5/2014 |
| WO | WO-2014098098 A1 | 6/2014 |
| WO | WO-2016020732 A1 | 2/2016 |
| WO | WO-2016028686 A1 | 2/2016 |
| WO | WO-2016128529 A1 | 8/2016 |
| WO | WO-2016144702 A1 | 9/2016 |
| WO | WO-2016144703 A1 | 9/2016 |
| WO | WO-2018048942 A1 | 3/2018 |
| WO | WO-2018048943 A1 | 3/2018 |

OTHER PUBLICATIONS

Berge et al. Pharmaceutical Salts. Journal of Pharmaceutical Sciences 66(1):1-19 (Jan. 1977).
Bertini et al. Alkylamino derivatives of 4-aminomethylpyridine as inhibitors of copper-containing amine oxidases. J Med Chem 48(3):664-670 (2005).
Cano et al. LOXL2 in epithelial cell plasticity and tumor progression. Future Oncol 8(9):1095-1108 (2012).
Chang et al. Pre-clinical evaluation of small molecule LOXL2 inhibitors in breast cancer. Oncotarget 8(16):26066-26078 (2017).
Chemical Abstract compounds, STN express—RN 1543432-15-0 (1 pg.) (Entered STN: Feb. 14, 2014).
Chien et al. Serum lysyl oxidase-like 2 levels and idiopathic pulmonary fibrosis disease progression. Eur Respir J 43(5):1430-1438 (2014).
Cosgrove et al. Ultrastructural, physiological, and molecular defects in the inner ear of a gene-knockout mouse model for autosomal Alport syndrome. Hear Res 121:84-98 (1998).
Cottet et al. Trifluoromethyl-Substituted Pyridines Through Displacement of Iodine by in situ Generated (Trifluoromethyl)copper. Eur J Org Chem 2002(2):327-330 (2002).
Friedlander. Fibrosis and diseases of the eye. J Clin Invest. 117:576-586 (2007).
Gabrielsen et al. Identification of Novel Serotonin Transporter Compounds by Virtual Screening. J Chem Inf Model 54(3):933-943 (2014).
Girogescu. Non-invasive Biochemical Markers of Liver Fibrosis. J. Gastrointestin. Liver Dis. 15(2):149-159(2006).
Hase et al. LOXL2 Status Correlates with Tumor Stage and Regulates Integrin Levels to Promote Tumor Progression in ccRCC. Mol Cancer Res 12(12):1807-1817 (2014).
Hutchinson et al. Small Molecule Lysyl Oxidase-like 2 (LOXL2) Inhibitors: The Identification of an Inhibitor Selective for LOXL2 over LOX. ACS Med. Chem. Lett. 8(4):423-427 (2017).
Ikenaga et al. A new Mdr2(-/-) mouse model of sclerosing cholangitis with rapid fibrosis progression, early-onset portal hypertension, and liver cancer. Am J Pathology 185:325-334 (2015).
Ishii et al. Fluid and Fibrosis in the Human Middle Ear. Am. J Otolaryngol 6(3):196-199 (1985).
Jones et al. A self-complete measure of health status for chronic airflow limitation. Am Rev Respir Dis 145:1321-1327 (1992).
Jones et al. The St. George's Respiratory Questionnaire. Resp Med 85:2531 (1991).
Jones. Interpreting thresholds for a clinically significant change in health status in asthma and COPD. Eur Respir J. 19(3):398-404 (2002).
Lee et al. A practical guide to pharmaceutical polymorph screening & selection. Asian Journal of Pharmaceutical Sciences 9(4):163-175 (2014).
Li et al. Liver fibrogenesis and the role of hepatic stellate cells: new insights and prospects for therapy. Gastroenterol. Hepatol. 14:618-633 (1999).
Liu et al. Recent progress in the synthesis of pyridinylboronic acids and esters. ARKIVOC 2013(i):135-153 (2013).
Londregan et al. General and mild preparation of 2-aminopyridines. Org Lett 12:5254-5257 (2010).
Marriott. Pharmaceutical Compound and Dispensing 2nd Ed. (pp. 1-288) (2010).
Mehal et al. Scraping fibrosis: expressway to the core of fibrosis. Nat Med. 17:552-553 (2011).
Nicholas et al. Lung Fibrosis: Fibroblast Biology, Thematic: Identification of Novel Small-Molecule Loxl2 Inhibitors By High Throughput Screening. Poster Session 2014 (1 pg.).
PCT/US2017/050332 International Search Report and Written Opinion dated Dec. 26, 2017.
Popov et al. Tissue transglutaminase does not affect fibrotic matrix stability or regression of liver fibrosis in mice. Gastroenetrology 140(5):1642-1652. (2011).
Rajagopalan et al. Biochemical and functional characterization of lysyl oxidase like 2 (LOXL2) inhibitors. Eur Resp Journal (44):P1518 (2014) (Abstract only).
Rodriguez et al. Modulation of lysyl oxidase-like 2 enzymatic activity by an allosteric antibody inhibitor. J Biol Chem 285(27):20964-20974 (2010).
Rowbottom et al. Identification of 4-(Aminomethyl)-6-(trifluoromethyl)-2-(phenoxy)pyridine Derivatives as Potent, Selective, and Orally Efficacious Inhibitors of the Copper-Dependent Amine Oxidase, Lysyl Oxidase-Like 2 (LOXL2). J Med Chem 50:4403-4423 (2017).
Sato et al. Comparative analysis of gene expression profiles in intact and damaged regions of human osteoarthritic cartilage. Arthritis & Rheumatism 54(3):808-817 (2006).
Schena et al. Pathogenic Mechanisms ofDiabetic Nephropathy. J. Am. Soc. Nephrol. 16:S30-33 (2005).
Tang et al. Beta-substituted ethylamine derivatives as suicide inhibitors of lysyl oxidase. J Biol Chem 259(2):975-979 (1984).
Taylor et al. Chapter 16: Amorphous Solids. Brittain, Polymorphism in Pharmaceutical Solids (pp. 587-629) (2009).
Threlfall. Analysis of organic polymorphs. A review. Analyst 120:2435-2460 (1995).
Tolboom et al. Invasiveness of fibroblast-like synoviocytes is an individual patient characteristic associated with the rate of joint destruction in patients with rheumatoid arthritis. Arthritis Rheum 52:1999-2002 (2005).
Van Bergen et al. The role of LOX and LOXL2 in scar formation after glaucoma surgery. Invest Ophthalmol Vis Sci. 54:5788-5796 (2013).
Van Bergen et al. The Role of LOX and LOXL2 in the Pathogenesis of an Experimental Model of Choroidal Neovascularization. Invest Ophthalmol Vis Sci 56(9):5280-5289 (2015).
West. Solid state chemistry and its applications Wiley New York pp. 358 and 365 (1988).

(56) References Cited

OTHER PUBLICATIONS

Whaley-Cannell et al. Chronic Kidney Disease and the Cardiometabolic Syndrome. J. Clin. Hypert. 8(8):546-48 (2006).

Williamson et al. Electronegativity of aromatic amines as a basis for the development of ground state inhibitors of lysyl oxidase. J Biol Chem 262(30):14520-14524 (1987).

Wuest et al. Targeting lysyl oxidase for molecular imaging in breast cancer. Breast Cancer Research 17:107 (2015).

Yin et al. A general and efficient 2-amination of pyridines and quinolines. J Org Chem 72:4554-4557 (2007).

Zablocki et al. Potent in vitro and in vivo inhibitors of platelet aggregation based upon the Arg-Gly-Asp sequence of fibrinogen. (Aminobenzamidino)succinyl (ABAS) series of orally active fibrinogen receptor antagonists. J Med Chem 38:2378-2394 (1995).

\* cited by examiner

XRPD of Compound 2, Form 1

DSC of Compound 2, Form 1

XRPD of Compound 2, Form 2

DSC of Compound 2, Form 3

XRPD of Compound 2, Form 4

DSC of Compound 2, Form 4

XRPD of Compound 1, Form 1

DSC of Compound 1, Form 1

DSC of Compound 1, Form 2

CRYSTALLINE FORMS OF A LYSYL OXIDASE-LIKE 2 INHIBITOR AND METHODS OF MAKING

CROSS-REFERENCE

This application is a continuation of U.S. patent application Ser. No. 16/331,095 filed Mar. 6, 2019, which is the U.S. National Phase entry of International Application No. PCT/US2017/050332 filed Sep. 6, 2017, which claims the benefit of U.S. Provisional Patent Application No. 62/384,596 filed on Sep. 7, 2016, each of which are incorporated by reference in their entireties.

FIELD OF THE INVENTION

Described herein are crystalline forms of the lysyl oxidase-like 2 (LOXL2) inhibitor (3-(4-(aminomethyl)-6-(trifluoromethyl)pyridin-2-yloxy)phenyl)((3R,4R)-3-fluoro-4-hydroxypyrrolidin-1-yl)methanone, pharmaceutically acceptable salts thereof, solvates thereof, as well as pharmaceutical compositions thereof, and methods of use thereof in the treatment or prevention of diseases or conditions associated with LOXL2 activity.

BACKGROUND OF THE INVENTION

Lysyl oxidase like-2 (LOXL2) is an amine oxidase enzyme that catalyzes crosslinking of extracellular matrix proteins. LOXL2 is also involved in intracellular processes such as mediating epithelial-to-mesenchymal transition of cells. LOXL2 signaling is implicated in, for example, in fibrotic diseases and cancer.

SUMMARY OF THE INVENTION

In one aspect, described herein is a pharmaceutically acceptable salt of (R,R)-trans-(3-((4-(aminomethyl)-6-(trifluoromethyl)pyridin-2-yl)oxy)phenyl)(3-fluoro-4-hydroxy-pyrrolidin-1-yl)methanone, wherein the pharmaceutically acceptable salt is a mesylate salt, hydrochloride salt, sulfate salt, maleate salt, phosphate salt, L-tartrate salt, fumarate salt, succinate salt, or acetate salt. In some embodiments, the pharmaceutically acceptable salt is a mesylate salt. In some embodiments, the pharmaceutically acceptable salt is a hydrochloride salt. In some embodiments, the pharmaceutically acceptable salt is a sulfate salt. In some embodiments, the pharmaceutically acceptable salt is a maleate salt. In some embodiments, the pharmaceutically acceptable salt is a phosphate salt. In some embodiments, the pharmaceutically acceptable salt is a L-tartrate salt. In some embodiments, the pharmaceutically acceptable salt is a fumarate salt. In some embodiments, the pharmaceutically acceptable salt is a succinate salt. In some embodiments, the pharmaceutically acceptable salt is an acetate salt.

In some embodiments, the pharmaceutically acceptable salt is a mesylate salt and has the structure of Compound 2:

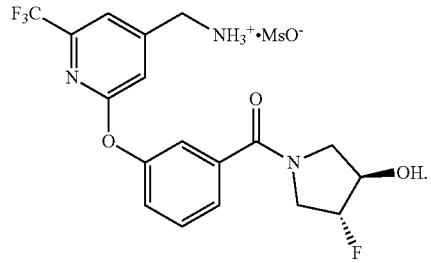

Compound 2

In some embodiments, Compound 2 is amorphous

In some embodiments, Compound 2 is crystalline. In some embodiments, Compound 2 is crystalline and has at least one of the following properties:
(a) an X-ray powder diffraction (XRPD) pattern with characteristic peaks at 13.6° 2-Theta, 16.9° 2-Theta, 19.4° 2-Theta, 20.1° 2-Theta, 20.3° 2-Theta, 20.6° 2-Theta, 23.1° 2-Theta, 23.6° 2-Theta;
(b) an X-ray powder diffraction (XRPD) pattern substantially the same as shown in FIG. 1;
(c) a DSC thermogram with endotherms at about 231° C. and about 236° C.; or
(d) a DSC thermogram substantially the same as shown in FIG. 2;
(e). reversible water uptake (~2.1% w/w) between 0 and 90% RH
(f) an unchanged XRPD after the GVS analysis.

In some embodiments, Compound 2 is crystalline and has an X-ray powder diffraction (XRPD) pattern with characteristic peaks at 13.6° 2-Theta, 16.9° 2-Theta, 19.4° 2-Theta, 20.1° 2-Theta, 20.3° 2-Theta, 20.6° 2-Theta, 23.1° 2-Theta, 23.6° 2-Theta. In some embodiments, Compound 2 is crystalline and has an X-ray powder diffraction (XRPD) pattern substantially the same as shown in FIG. 1. In some embodiments, Compound 2 is crystalline and has a DSC thermogram with endotherms at about 231° C. and about 236° C. In some embodiments, Compound 2 is crystalline and has a DSC thermogram substantially the same as shown in FIG. 2.

In some embodiments, Compound 2 is crystalline and has at least one of the following properties:
(a) an X-ray powder diffraction (XRPD) pattern with characteristic peaks at 2.6° 2-Theta, 3.2° 2-Theta, 6.3° 2-Theta, 9.4° 2-Theta, 15.7° 2-Theta, 22.1° 2-Theta;
(b) an X-ray powder diffraction (XRPD) pattern substantially the same as shown in FIG. 3;
(c) a DSC thermogram with three endotherms at about 121.7° C., 231.1° C. and 236.1° C.; or
(d) a DSC thermogram substantially the same as shown in FIG. 4;
(e) is anhydrous;
(f) transformation to Compound 2, Form 1 when heated above 150° C.;
(g) transformation to Compound 2, Form 1 after GVS analysis and 7 days at 40° C./75% RH;
(h) transformation to Compound 2, Form 1 after 7 days at 25° C./97% RH.

In some embodiments, Compound 2 is crystalline and has an X-ray powder diffraction (XRPD) pattern with characteristic peaks at 2.6° 2-Theta, 3.2° 2-Theta, 6.3° 2-Theta, 9.4° 2-Theta, 15.7° 2-Theta, 22.1° 2-Theta. In some embodiments, Compound 2 is crystalline and has an X-ray powder diffraction (XRPD) pattern substantially the same as shown in FIG. 3. In some embodiments, Compound 2 is crystalline and has a DSC thermogram with three endotherms at about 121.7° C., 231.1° C. and 236.1° C. In some embodiments, Compound 2 is crystalline and has a DSC thermogram substantially the same as shown in FIG. 4. In some embodiments, Compound 2 is crystalline and anhydrous.

In some embodiments, Compound 2 is crystalline and has at least one of the following properties:
(a) an X-ray powder diffraction (XRPD) pattern with characteristic peaks at 2.9° 2-Theta, 3.2° 2-Theta, 3.3° 2-Theta, 15.8° 2-Theta, 16.9° 2-Theta, 20.2° 2-Theta;
(b) an X-ray powder diffraction (XRPD) pattern substantially the same as shown in FIG. 5;
(c) a DSC thermogram with two endotherms at about 132.2° C. and 238.8° C.;
(d) a DSC thermogram substantially the same as shown in FIG. 6;
(e) solvated with dimethylsulfoxide (DMSO);
(f) transformation to Compound 2, Form 1 when heated above 130° C.;
(g) transformation to Compound 2, Form 1 after GVS analysis and 7 days at 40° C./75% RH;
(h) transformation to Compound 2, Form 1 after 7 days at 40° C. and 75% RH.

In some embodiments, Compound 2 is crystalline and has an X-ray powder diffraction (XRPD) pattern with characteristic peaks at 2.9° 2-Theta, 3.2° 2-Theta, 3.3° 2-Theta, 15.8° 2-Theta, 16.9° 2-Theta, 20.2° 2-Theta. In some embodiments, Compound 2 is crystalline and has an X-ray powder diffraction (XRPD) pattern substantially the same as shown in FIG. 5. In some embodiments, Compound 2 is crystalline and has a DSC thermogram with two endotherms at about 132.2° C. and 238.8° C. In some embodiments, Compound 2 is crystalline and has a DSC thermogram substantially the same as shown in FIG. 6. In some embodiments, Compound 2 is crystalline and solvated with dimethylsulfoxide (DMSO).

In some embodiments, Compound 2 is crystalline and has at least one of the following properties:
(a) an X-ray powder diffraction (XRPD) pattern with characteristic peaks at 13.9° 2-Theta, 16.6° 2-Theta, 18.8° 2-Theta, 19.1° 2-Theta, 19.7° 2-Theta, 19.9° 2-Theta, 20° 2-Theta, 21.2° 2-Theta, 22.3° 2-Theta, 22.7° 2-Theta, 23.4° 2-Theta, 23.8° 2-Theta;
(b) an X-ray powder diffraction (XRPD) pattern substantially the same as shown in FIG. 7;
(c) a DSC thermogram with an endotherm at about 233° C.; or
(d) a DSC thermogram substantially the same as shown in FIG. 8.

In some embodiments, Compound 2 is crystalline and has an X-ray powder diffraction (XRPD) pattern with characteristic peaks at 13.9° 2-Theta, 16.6° 2-Theta, 18.8° 2-Theta, 19.1° 2-Theta, 19.7° 2-Theta, 19.9° 2-Theta, 20° 2-Theta, 21.2° 2-Theta, 22.3° 2-Theta, 22.7° 2-Theta, 23.4° 2-Theta, 23.8° 2-Theta. In some embodiments, Compound 2 is crystalline and has an X-ray powder diffraction (XRPD) pattern substantially the same as shown in FIG. 7. In some embodiments, Compound 2 is crystalline and has a DSC thermogram with an endotherm at about 233° C. In some embodiments, Compound 2 is crystalline and has a DSC thermogram substantially the same as shown in FIG. 8.

In some embodiments, the pharmaceutically acceptable salt is a hydrochloride salt and has the structure of Compound 1:

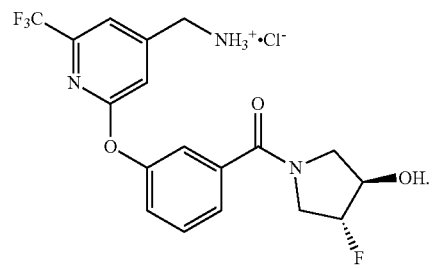

Compound 1

In some embodiments, Compound 1 is amorphous. In some embodiments, Compound 1 is amorphous and deliquesces at 40° C./75% RH.

In some embodiments, Compound 1 is crystalline. In some embodiments, Compound 1 is crystalline and has at least one of the following properties:
(a) an X-ray powder diffraction (XRPD) pattern with characteristic peaks at 5.5° 2-Theta, 7.5° 2-Theta, 18.5° 2-Theta, 19.4° 2-Theta, 21.8° 2-Theta, 23.5° 2-Theta;
(b) an X-ray powder diffraction (XRPD) pattern substantially the same as shown in FIG. 9;
(c) a DSC thermogram with an endotherm at about 153° C.; or
(d) a DSC thermogram substantially the same as shown in FIG. 10.

In some embodiments, Compound 1 is crystalline and has an X-ray powder diffraction (XRPD) pattern with characteristic peaks at 5.5° 2-Theta, 7.5° 2-Theta, 18.5° 2-Theta, 19.4° 2-Theta, 21.8° 2-Theta, 23.5° 2-Theta. In some embodiments, Compound 1 is crystalline and has an X-ray powder diffraction (XRPD) pattern substantially the same as shown in FIG. 9. In some embodiments, Compound 1 is crystalline and has a DSC thermogram with an endotherm at about 153° C. In some embodiments, Compound 1 is crystalline and has a DSC thermogram substantially the same as shown in FIG. 10. In some embodiments, Compound 1 is crystalline and is a hygroscopic solid.

In some embodiments, Compound 1 is crystalline and has at least one of the following properties:
(a) an X-ray powder diffraction (XRPD) pattern with characteristic peaks at 6.6° 2-Theta, 13.2° 2-Theta, 19.7° 2-Theta, 22.3° 2-Theta, 22.5° 2-Theta, 23.7° 2-Theta, 24.5° 2-Theta, 26.4° 2-Theta;
(b) an X-ray powder diffraction (XRPD) pattern substantially the same as shown in FIG. 11;
(c) a DSC thermogram with endotherms at about 43° C. and about 119° C.; or
(d) a DSC thermogram substantially the same as shown in FIG. 12.

In some embodiments, Compound 1 is crystalline and has an X-ray powder diffraction (XRPD) pattern with characteristic peaks at 6.6° 2-Theta, 13.2° 2-Theta, 19.7° 2-Theta, 22.3° 2-Theta, 22.5° 2-Theta, 23.7° 2-Theta, 24.5° 2-Theta, 26.4° 2-Theta. In some embodiments, Compound 1 is crystalline and has an X-ray powder diffraction (XRPD) pattern substantially the same as shown in FIG. 11. In some embodiments, Compound 1 is crystalline and has a DSC thermogram with endotherms at about 43° C. and about 119° C. In some embodiments, Compound 1 is crystalline and has a DSC thermogram substantially the same as shown in FIG. 12.

In one aspect, described herein is a pharmaceutical composition comprising a pharmaceutically acceptable salt of any one of the above embodiments, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is formulated for administration to a mammal by oral administration. In some embodiments, the pharmaceutical composition is formulated for administration to a mammal by oral administration in the form of a tablet, a pill, a capsule, a suspension, or a solution. In some embodiments, the pharmaceutical composition is in the form of a solid form pharmaceutical composition. In some embodiments, the pharmaceutical composition is in the form of a tablet, a pill, or a capsule. In some embodiments, the pharmaceutical composition comprises about 1 mg to about 2000 mg of (R,R)-trans-(3-((4-(aminomethyl)-6-(trifluoromethyl)pyridin-2-yl)oxy)phenyl)(3-fluoro-4-hydroxypyrrolidin-1-yl) methanone. In some embodiments, the pharmaceutical composition is in the form of a tablet and comprises about 50 mg or about 250 mg of (R,R)-trans-(3-((4-(aminomethyl)-6-(trifluoromethyl)pyridin-2-yl)oxy)phenyl)(3-fluoro-4-hydroxypyrrolidin-1-yl)methanone per tablet.

In another aspect, described herein is a process for the synthesis of (R,R)-trans-(3-((4-(aminomethyl)-6-(trifluoromethyl)pyridin-2-yl)oxy)phenyl)(3-fluoro-4-hydroxypyrrolidin-1-yl)methanone (Compound I) comprising the step of reducing nitrile Compound A-7 having the following structure:

Compound A-7

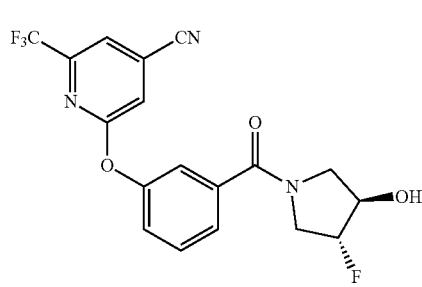

under suitable nitrile reducing conditions to provide (R,R)-trans-(3-((4-(aminomethyl)-6-(trifluoromethyl) pyridin-2-yl)oxy)phenyl)(3-fluoro-4-hydroxypyrrolidin-1-yl)methanone (Compound I):

Compound I

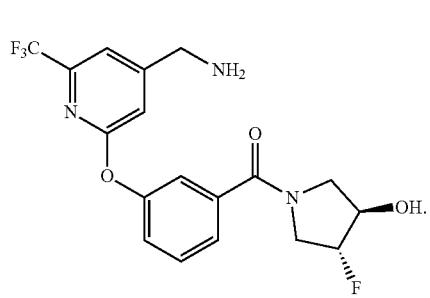

In some embodiments, the suitable nitrile reducing conditions comprise catalytic hydrogenation conditions.

In some embodiments, the catalytic hydrogenation conditions comprise: a palladium catalyst, platinum catalyst, iron catalyst, cobalt catalyst, nickel catalyst, ruthenium catalyst, rhodium catalyst, iridinium catalyst, or osmium catalyst; and hydrogen gas. In some embodiments, the catalytic hydrogenation conditions comprise: a palladium catalyst or platinum catalyst that is supported on activated carbon, $Al_2O_3$, $TiO_2$, $ZrO_2$, or $SiO_2$; and hydrogen gas. In some embodiments, the catalytic hydrogenation conditions comprise: acetic acid; palladium hydroxide on carbon; and hydrogen gas.

In some embodiments, nitrile compound A-7:

Compound A-7

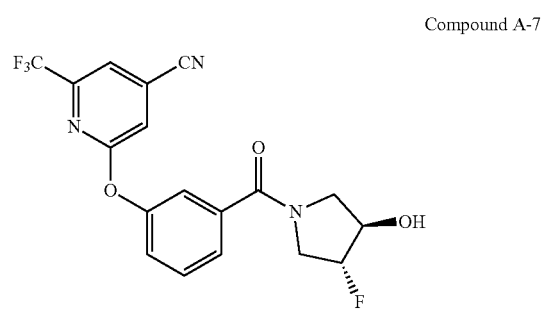 [SMILES: N#Cc1cc(Oc2cccc(C(=O)N3C[C@@H](O)[C@H](F)C3)c2)nc(C(F)(F)F)c1]

is prepared by coupling benzoic acid Compound A-6:

Compound A-6

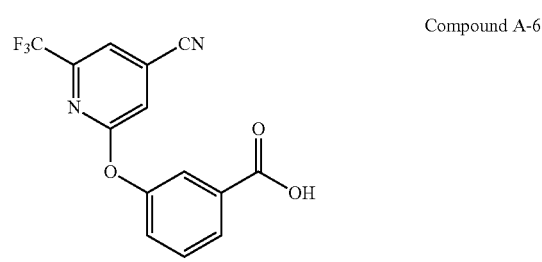 [SMILES: N#Cc1cc(Oc2cccc(C(=O)O)c2)nc(C(F)(F)F)c1]

with (3R,4R)-4-fluoropyrrolidin-3-ol under suitable coupling conditions.

In some embodiments, suitable coupling conditions comprise: conversion of benzoic acid A-6 into the corresponding acyl chloride; and coupling the corresponding acyl chloride of benzoic acid Compound A-6 with (3R,4R)-4-fluoropyrrolidin-3-ol.

In some embodiments, conversion of benzoic acid A-6 into the corresponding acyl halide comprises treating benzoic acid C with thionyl chloride ($SOCl_2$), oxalyl chloride (($COCl)_2$), phosphorus trichloride ($PCl_3$), phosphorus oxychloride ($POCl_3$), or phosphorus pentachloride ($PCl_5$).

In some embodiments, coupling the corresponding acyl chloride of benzoic acid A-6 with (3R,4R)-4-fluoropyrrolidin-3-ol comprises a non-nucleophilic tertiary amine base. In some embodiments, non-nucleophilic tertiary amine is tritheylamine, tributylamine, N,N-diisopropylethylamine, 8-diazabicycloundec-7-ene, 1,2,2,6,6-pentamethylpiperidine, N-methylmorpholine or pyridine.

In some embodiments, suitable coupling conditions comprise: the use of dicyclohexylcarbodiimide (DCC), diisopropylcarbodiimide (DIC), N-(3-dimethylaminopropyl)-N'-ethylcarbodiimide.HCl (EDC HCl), benzotriazol-1-yloxy-tris (dimethylamino)-phosphonium hexafluorophosphate (BOP), benzotriazol-1-yloxy-tripyrrolidino-phosphonium hexafluorophosphate (PyBOP), bromo-tripyrrolidino-phosphonium hexafluorophosphate (PyBrOP), 7-aza-benzotriazol-1-yloxy-tripyrrolidinophosphonium hexafluorophosphate (PyAOP), ethyl cyano(hydroxyimino)acetato-O₂)-tri-(1-pyrrolidinyl)-phosphonium hexafluorophosphate (PyOxim), 3-(diethoxy-phosphoryloxy)-1,2,3-benzo[d]triazin-4(3H)-one (DEPBT), 2-(1H-benzotriazol-1-yl)-N,N,N',N'-tetramethylaminium tetrafluoroborate/hexafluorophosphate (TBTU (BF₄⁻)), 2-(6-chloro-1H-benzotriazol-1-yl)-N,N,N',N'-tetramethylaminium hexafluorophosphate (HCTU), N-[(5-chloro-1H-benzotriazol-1-yl)-dimethylamino-morpholino]-uronium hexafluorophosphate N-oxide (HDMC), 2-(7-aza-1H-benzotriazol-1-yl)-N,N,N',N'-tetramethylaminium hexafluorophosphate (HATU), 1-[1-(cyano-2-ethoxy-2-oxoethylideneaminooxy)-dimethylamino-morpholino]-uronium hexafluorophosphate (COMU), 2-(1-oxy-pyridin-2-yl)-1,1,3,3-tetramethylisothiouronium tetrafluoroborate (TOTT), tetramethylfluoroformamidinium hexafluorophosphate (TFFH), N-ethoxycarbonyl-2-ethoxy-1,2-dihydroquinoline (EEDQ), 2-propanephosphonic acid anhydride (T3P), 4-(4,6-dimethoxy-1,3,5-triazin-2-yl)-4-methylmorpholinium salts (DMTMM), bis-trichloromethylcarbonate (BTC), or 1,1'-carbonyldiimidazole (CDI). In some embodiments, the suitable coupling conditions further comprise: one or more additives selected from the group consisting of 1-hydroxybenzotriazole (HOBt), 1-hydroxybenzotriazole-6-sulfonamidomethyl resin.HCl (HOBt-6-sulfonamidomethyl resin.HCl), hydroxy-3,4-dihydro-4-oxo-1,2,3-benzotriazine (HOOBt), N-hydroxysuccinimide (HOSu), 1-Hydroxy-7-aza-1H-benzotriazole (HOAt), ethyl 2-cyano-2-(hydroximino)acetate, and 4-(N,N-Dimethylamino)pyridine (DMAP).

In some embodiments, benzoic acid A-6:

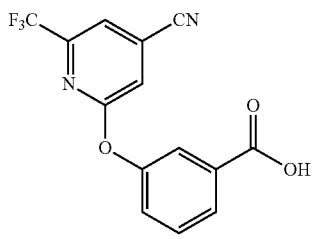

Compound A-6 is prepared by coupling 2-chloro-6-(trifluoromethyl)isonicotinonitrile:

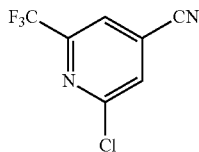

with 3-hydroxybenzoic acid:

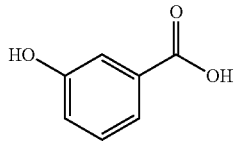

under suitable reaction conditions.

In some embodiments, suitable reaction conditions include nucleophilic aromatic substitution (SNAr) reaction conditions. In some embodiments, suitable reaction conditions comprise an organic or inorganic base in a suitable solvent. In some embodiments, suitable reaction conditions comprise an inorganic base selected from the group consisting of lithium hydroxide, sodium hydroxide, potassium hydroxide, sodium bicarbonate, potassium bicarbonate, cesium bicarbonate, sodium carbonate, potassium carbonate, cesium carbonate, sodium acetate, potassium acetate, sodium phosphate and potassium phosphate; and a suitable solvent selected from the group consisting of dimethylformamide, dimethylacetamide, tetrahydrofuran, tetrafropyran, and dioxane.

In another embodiments, described herein is a process for the synthesis of (R,R)-trans-(3-((4-(aminomethyl)-6-(trifluoromethyl)pyridin-2-yl)oxy)phenyl)(3-fluoro-4-hydroxypyrrolidin-1-yl)methanone, methanesulfonate salt (Compound 2) comprising the step of treating Compound C:

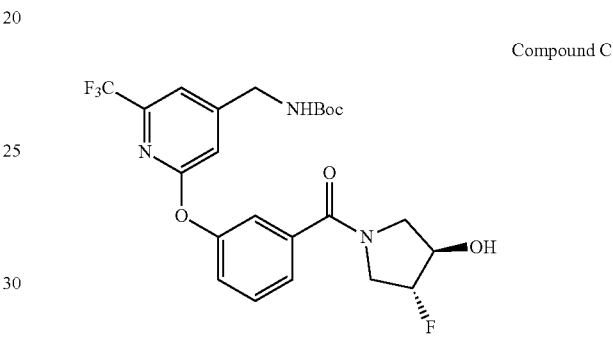

Compound C with methanesulfonic acid in a suitable solvent to provide Compound 2:

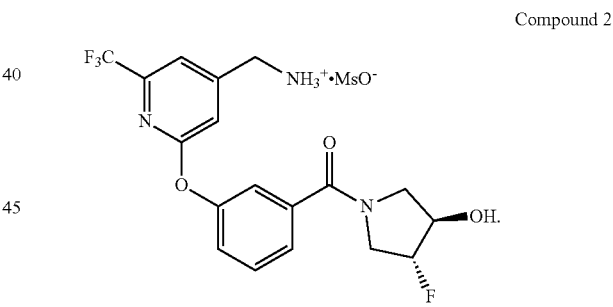

Compound 2

In some embodiments, the suitable solvent is dichloromethane.

In some embodiments, compound C:

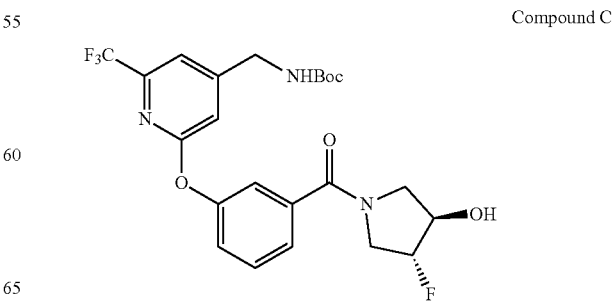

Compound C is prepared by coupling benzoic acid Compound A:

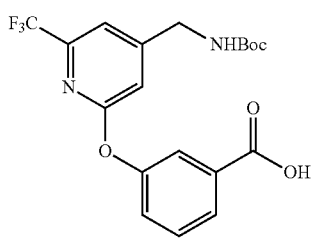

Compound A with (3R,4R)-4-fluoropyrrolidin-3-ol, hydrochloride under suitable coupling conditions.

In some embodiments, suitable coupling conditions comprise: conversion of benzoic acid Compound A into the corresponding acyl chloride; and coupling the corresponding acyl chloride of benzoic acid Compound A with (3R, 4R)-4-fluoropyrrolidin-3-ol, hydrochloride.

In some embodiments, conversion of benzoic acid Compound A into the corresponding acyl halide comprises treating benzoic acid Compound A with thionyl chloride ($SOCl_2$), oxalyl chloride (($COCl)_2$), phosphorus trichloride ($PCl_3$), phosphorus oxychloride ($POCl_3$), or phosphorus pentachloride ($PCl_5$).

In some embodiments, coupling the corresponding acyl chloride of benzoic acid Compound A with (3R,4R)-4-fluoropyrrolidin-3-ol, hydrochloride comprises a non-nucleophilic tertiary amine base. In some embodiments, the non-nucleophilic tertiary amine is triethylamine, tributylamine, N,N-diisopropylethylamine, 8-diazabicycloundec-7-ene, 1,2,2,6,6-pentamethylpiperidine, N-methylmorpholine or pyridine.

In some embodiments, suitable coupling conditions comprise: the use of dicyclohexylcarbodiimide (DCC), diisopropylcarbodiimide (DIC), N-(3-dimethylaminopropyl)-N'-ethylcarbodiimide.HCl (EDC HCl), benzotriazol-1-yloxy-tris(dimethylamino)-phosphonium hexafluorophosphate (BOP), benzotriazol-1-yloxy-tripyrrolidino-phosphonium hexafluorophosphate (PyBOP), bromo-tripyrrolidino-phosphonium hexafluorophosphate (PyBrOP), 7-aza-benzotriazol-1-yloxy-tripyrrolidinophosphonium hexafluorophosphate (PyAOP), ethyl cyano(hydroxyimino)acetato-$O_2$)-tri-(1-pyrrolidinyl)-phosphonium hexafluorophosphate (PyOxim), 3-(diethoxy-phosphoryloxy)-1,2,3-benzo[d]triazin-4(3H)-one (DEPBT), 2-(1H-benzotriazol-1-yl)-N,N,N',N'-tetramethylaminium tetrafluoroborate/hexafluorophosphate (TBTU ($BF_4^-$)), 2-(6-chloro-1H-benzotriazol-1-yl)-N,N,N',N'-tetramethylaminium hexafluorophosphate (HCTU), N-[(5-chloro-1H-benzotriazol-1-yl)-dimethylamino-morpholino]-uronium hexafluorophosphate N-oxide (HDMC), 2-(7-aza-1H-benzotriazol-1-yl)-N,N,N',N'-tetramethylaminium hexafluorophosphate (HATU), 1-[1-(cyano-2-ethoxy-2-oxoethylideneaminooxy)-dimethylamino-morpholino]-uronium hexafluorophosphate (COMU), 2-(1-oxy-pyridin-2-yl)-1,1,3,3-tetramethylisothiouronium tetrafluoroborate (TOTT), tetramethylfluoroformamidinium hexafluorophosphate (TFFH), N-ethoxycarbonyl-2-ethoxy-1,2-dihydroquinoline (EEDQ), 2-propanephosphonic acid anhydride (T3P), 4-(4,6-dimethoxy-1,3,5-triazin-2-yl)-4-methylmorpholinium salts (DMTMM), bis-trichloromethylcarbonate (BTC), or 1,1'-carbonyldiimidazole (CDI). In some embodiments, the suitable coupling conditions further comprise: one or more additives selected from the group consisting of 1-hydroxybenzotriazole (HOBt), 1-hydroxybenzotriazole-6-sulfonamidomethyl resin.HCl (HOBt-6-sulfonamidomethyl resin.HCl), hydroxy-3,4-dihydro-4-oxo-1,2,3-benzotriazine (HOOBt), N-hydroxysuccinimide (HOSu), 1-Hydroxy-7-aza-1H-benzotriazole (HOAt), ethyl 2-cyano-2-(hydroximino)acetate, and 4-(N,N-Dimethylamino)pyridine (DMAP).

In yet another aspect, described herein is a process for the synthesis of (R,R)-trans-(3-((4-(aminomethyl)-6-(trifluoromethyl)pyridin-2-yl)oxy)phenyl)(3-fluoro-4-hydroxypyrrolidin-1-yl)methanone, methanesulfonate salt (Compound 2) comprising the step of treating (R,R)-trans-(3-((4-(aminomethyl)-6-(trifluoromethyl)pyridin-2-yl)oxy)phenyl)(3-fluoro-4-hydroxypyrrolidin-1-yl)methanone (Compound I) with 0.92 eq of methanesulfonic acid in acetonitrile and then isolating Compound 2 by filtration and drying under vacuum. In some embodiments, the step of treating Compound I with methanesulfonic acid in acetonitrile further comprises stirring the solution at ambient temperature followed by refluxing the solution.

In another aspect, described herein is a process for the synthesis of (3R,4R)-4-fluoropyrrolidin-3-ol, hydrochloride comprising:
a) subjecting racemic-(trans-3-fluoro-4-hydroxypyrrolidin-1-yl)(phenyl)methanone to enzymatic biocatalysis to provide ((3R,4R)-3-fluoro-4-hydroxypyrrolidin-1-yl)(phenyl)methanone; and
b) cleaving the amide bond of ((3R,4R)-3-fluoro-4-hydroxypyrrolidin-1-yl)(phenyl)methanone to provide (3R,4R)-4-fluoropyrrolidin-3-ol, hydrochloride.

In some embodiments, enzyme biocatalysis includes the use of a suitable lipase. In some embodiments, the suitable lipase is capable of lipase-catalyzed transesterification of secondary alcohols. In some embodiments, the suitable lipase is a fungal lipase or a bacterial lipase. In some embodiments, the fungal lipase is derived from *Candida rugose* (CRL), *Candida antarctica* A (CAL-A), *Candida antarctica* B (CAL-B), *Thermomyces lanuginosus* (TL IL), or *Rhizomucor miehei* (RL IM). In some embodiments, the bacterial lipase is derived from *Pseudomonas fluorescens* (AK, PFL), *Burkholderia cepacia* (PS), *Chromobacterium viscosum* (CVL). In some embodiments, the suitable lipase is Novozyme 435, Novocor AD L and Lipozyme CALB L. In some embodiments, the lipase-catalyzed transesterification is performed in the presence of an acyl donor. In some embodiments, the acyl donor is an irreversible acyl donor. In some embodiments, the acyl donor is an enol ester or anhydride. In some embodiments, the enol ester is a vinyl ester, isoprenyl ester, or ethoxy vinyl ester. In some embodiments, the enol ester is a vinyl ester that is selected from the group consisting of acetate vinyl ester, pivalate vinyl ester, 4-pentenoate vinyl ester, crotonate vinyl ester, methacrylate vinyl ester, benzoate vinyl ester, cinnamate vinyl ester, N-Boc glycinate vinyl ester, and phenyl(thio)acetate vinyl ester. In some embodiments, the enzymatic biocatalysis is performed in an organic solvent. In some embodiments, the organic solvent is dimethylsulfoxide, N,N-dimethylformamide, methanol, ethanol, acetone, methyl acetate, ethyl acetate, butanol, diethylether, TBME, DIPE, toluene, cyclohexane, hexane, or heptane. In some embodiments, the organic solvent is acetone, tetrahydrofuran, diethyl ether, tert-amyl alcohol, DIPE, or toluene.

In some embodiments, step b) comprises treating ((3R, 4R)-3-fluoro-4-hydroxypyrrolidin-1-yl)(phenyl)methanone with an acid in a suitable solvent. In some embodiments, the acid is hydrochloric acid. In some embodiments, the suitable solvent is an organic solvent. In some embodiments, the organic solvent is an ether solvent. In some embodiments, the organic solvent is 1,4-dioxane, tetrahydrofuran, tetrahydropyran, dimethoxyethane or diethyl ether.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by inhalation; and/or (e) t administered by nasal administration; or and/or (f) administered by injection to the mammal; and/or (g) administered topically to the mammal; and/or (h) administered by ophthalmic administration; and/or (i) administered rectally to the mammal; and/or (j) adminstered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the aforementioned aspects involving the treatment of a disease or condition are further embodiments comprising administering at least one additional agent in addition to the administration of a compound of Formula (I) described herein, or a pharmaceutically acceptable salt thereof. In various embodiments, each agent is administered in any order, including simultaneously.

In any of the embodiments disclosed herein, the mammal is a human.

In some embodiments, compounds provided herein are administered to a human.

In some embodiments, compounds provided herein are orally administered.

Articles of manufacture, which include packaging material, a compound described herein, or a pharmaceutically acceptable salt thereof, within the packaging material, and a label that indicates that the compound or composition, or pharmaceutically acceptable salt, pharmaceutically active metabolite, pharmaceutically acceptable prodrug, or pharmaceutically acceptable solvate thereof, is used for inhibiting the activity of LOXL2, or for the treatment, prevention or amelioration of one or more symptoms of a disease or condition that would benefit from inhibition or reduction of the LOXL2 activity, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Figure 1:
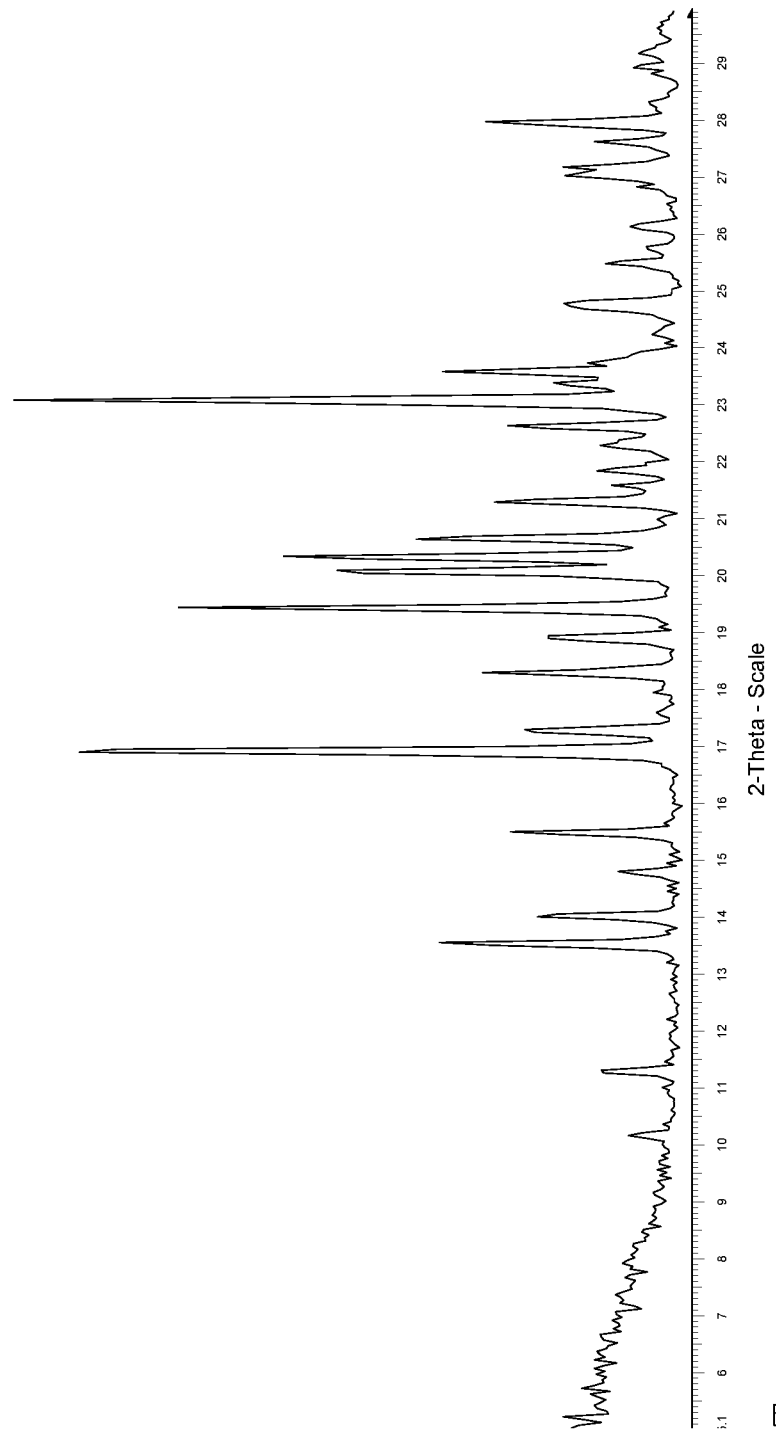
FIG. 1 illustrates the X-ray powder diffraction pattern for Form 1 of Compound 2.

Lysyl oxidase like-2 (LOXL2) is a member of the lysyl oxidase (LOX) family, which comprises $Cu^{2+}$ and lysine tyrosylquinone (LTQ)-dependent amine oxidases. The family comprises five genes: lox (LOX), loxl1 (lysyl oxidase like-1, LOXL1), loxl2 (LOXL2), loxl3 (lysyl oxidase like-3, LOXL3), and loxl4 (lysyl oxidase like-4, LOXL4). The LOX family is known for catalyzing the oxidative deamination of the ε-amino group of lysines and hydroxylysines in collagen and elastin to promote crosslinking of these molecules. Crosslinking of collagen and elastin is essential for maintaining tensile strength of the extracellular matrix.

The development of pathologic stroma plays an important role in disease. Pathologic stroma is composed of activated stromal cells, collagenous matrix, growth factors, and angiogenic structures. During pathologic conditions such as fibrogenesis, fibroblasts are recruited and activated resulting in the generation of a microenvironment that fosters increased synthesis and deposition of extracellular matrix proteins leading to the development of fibrosis.

Disease-associated fibroblast activation in fibrotic disease and cancer results in remodeling of the extracellular matrix that ultimately leads to excessive deposition of extracellular matrix proteins, including collagen I and III, increased cross-linking of the newly deposited collagen and enhanced tissue stiffness. In addition, activated fibroblasts express numerous pro-angiogenic, pro-vasculogenic, and pro-proliferative growth factors and cytokines such as transforming growth factor beta (TGF-β), connective tissue growth factor (CTGF), stromal cell-derived factor 1 (SDF-1), and vascular endothelial growth factor (VEGF), thereby playing important roles in paracrine signaling in disease progression. Disrupting the development of this pathologic stroma through inhibition of fibroblast activation and recruitment and/or their signaling pathways represents a novel therapeutic strategy in fibrotic disease.

Despite similar catalytic activity, each lysyl oxidase enzyme has been reported to have unique expression and functional activities. LOXL2 plays a central role in the development of pathologic stroma in fibrotic diseases by activating and recruiting fibroblasts to the pathologic site.

LOXL2 has been demonstrated to have intracellular functions aside from its role in remodeling of the extracellular matrix. LOXL2 positively regulates the epithelial-to-mesenchymal transition (EMT) transducer, Snail1, by promoting Snail1 stability and functional activity. LOXL2 contributes positively to the activation of the focal adhesion kinase (FAK) signaling pathway and participates in the organization of focal adhesion complexes. Silencing of LOXL2 gene leads to reacquisition of epithelial cell polarity and decreases the migratory and invasive ability of mammary cell lines. The modulation of cell adhesion and cell polarity has been reported to be mediated by intracellular LOXL2. LOXL2 transcriptionally represses E-cadherin as well as tight junction and cell polarity genes by Snail1-dependent and Snail1-independent mechanisms. LOXL2 has been more recently described to be associated with chromatin and reported to be involved in histone H3 trimethyl deamination, a function that is dependent on the LOXL2 catalytic domain.

LOXL2 is involved in fibrotic processes. Fibrotic processes include an excessive deposition of extracellular matrix components, such as collagen, which alters the physical, biochemical and biomechanical matrix properties leading to defective organ function and organ failure. Tissue fibrosis is also associated with cancer progression by direct promotion of cellular transformation and metastasis. Tumors are typically stiffer than normal tissue and tumor rigidity influences tumor metastasis.

Excessive LOXL2 enzyme activity has been implicated in the increased stiffness of tumors. Elevated LOXL2 is also associated with fibrotic lesions from livers of patients suffering from Wilson disease, primary biliary cirrhosis and NASH. Additionally, the administration of a LOXL2-specific monoclonal antibody, AB0023, was efficacious in reducing disease in a model of fibrosis. AB0023 was shown to inhibit the production of growth factors and of crosslinked collagenous matrix and TGF-beta signaling.

LOXL2 promotes type I collagen cross-linking and is a core regulator of fibrogenesis of various etiologies and in various organs. Levels of circulating LOXL2 correlate with fibrotic stage. LOXL2 is a core pathway target in fibrotic disease. Mehal et al. "Expressway to the core of fibrosis," Nat Med. 2011. 17: 552-553.

In some embodiments, disclosed herein is the use of Compound I, or a pharmaceutically acceptable salt or solvate thereof, in the treatment or prevention of fibrosis in a mammal.

"Fibrosis," as used herein, refers to the accumulation of extracellular matrix constituents that occurs following trauma, inflammation, tissue repair, immunological reactions, cellular hyperplasia, and neoplasia.

In some embodiments, disclosed herein is a method of reducing fibrosis in a tissue comprising contacting a fibrotic cell or tissue with a compound disclosed herein, in an amount sufficient to decrease or inhibit the fibrosis. In some embodiments, the fibrosis includes a fibrotic condition.

In some embodiments, the fibrosis comprises lung fibrosis, liver fibrosis, kidney fibrosis, cardiac fibrosis, peritoneal fibrosis, ocular fibrosis, myelofibrosis or cutaneous fibrosis. In some embodiments, the fibrosis comprises lung fibrosis. In some embodiments, the fibrosis comprises liver fibrosis. In some embodiments, the fibrosis comprises kidney fibrosis. In some embodiments, the fibrosis comprises cardiac fibrosis. In some embodiments, the fibrosis comprises peritoneal fibrosis. In some embodiments, the fibrosis comprises ocular fibrosis. In some embodiments, the fibrosis comprises cutaneous fibrosis.

Increased LOXL2 expression is associated with poor prognosis in patients with colon, esophageal tumors, oral squamous cell carcinomas, laryngeal squamous cell carcinomas, and head and neck squamous cell carcinomas. LOXL2 has been proposed to participate in cancers of the breast, colon, gastric, head and neck, lung, and melanoma.

In some embodiments, disclosed herein are methods of treating cancer with a compound disclosed herein.

The term "cancer" as used herein, refers to an abnormal growth of cells that tend to proliferate in an uncontrolled way and, in some cases, to metastasize (spread). Types of cancer include, but are not limited to, solid tumors (such as those of the bladder, bowel, brain, breast, endometrium, heart, kidney, lung, liver, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

In some embodiments, disclosed herein is a method of treating rheumatoid arthritis, juvenile idiopathic arthritis, osteoarthritis, psoriatic arthritis, or ankylosing spondylitis in a mammal comprising Compound I, or a pharmaceutically acceptable salt thereof (e.g. Compound 1 or Compound 2), or a pharmaceutically acceptable salt thereof, to the mammal in need thereof.

(R,R)-trans-(3-((4-(Aminomethyl)-6-(trifluoromethyl)pyridin-2-yl)oxy)phenyl)(3-fluoro-4-hydroxypyrrolidin-1-yl)methanone (Compound I)

"Compound I" or "(R,R)-trans-(3-((4-(aminomethyl)-6-(trifluoromethyl)pyridin-2-yl)oxy)phenyl)(3-fluoro-4-hydroxypyrrolidin-1-yl)methanone" or "(3-((4-(aminomethyl)-6-(trifluoromethyl)-pyridin-2-yl)oxy)phenyl)(3R,4R)-3-fluoro-4-hydroxypyrrolidin-1-yl)methanone", or any other similar name refers to the compound with the following structure:

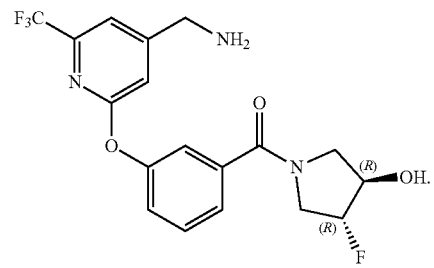

In some embodiments, Compound I is substantially free of the (S,S)-isomer (i.e. Compound I is substantially free of "(S,S)-trans-(3-((4-(aminomethyl)-6-(trifluoromethyl)pyridin-2-yl)oxy)phenyl)(3-fluoro-4-hydroxypyrrolidin-1-yl) methanone" or "(3-((4-(aminomethyl)-6-(trifluoromethyl)-pyridin-2-yl)oxy)phenyl)(3S,4S)-3-fluoro-4-hydroxypyrrolidin-1-yl)methanone", or any other similar name).

"Substantially free" with respect to an enantiomer, means that the referenced enantiomer is not present or there is less than 5%, less than 4%, less than 3%, less than 2% or less than 1% of the referenced enantiomer.

"Compound Ent-I" or "(S,S)-trans-(3-((4-(aminomethyl)-6-(trifluoromethyl)pyridin-2-yl)oxy)phenyl)(3-fluoro-4-hydroxypyrrolidin-1-yl)methanone" or "(3-((4-(aminomethyl)-6-(trifluoromethyl)-pyridin-2-yl)oxy)phenyl)(3S,4S)-3-fluoro-4-hydroxypyrrolidin-1-yl)methanone", or any other similar name refers to the compound with the following structure:

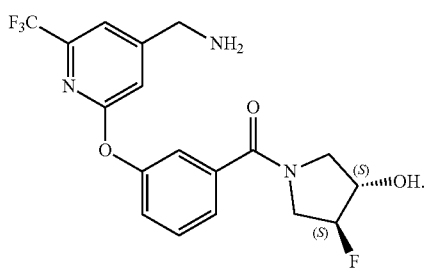

In some embodiments, racemic-trans-(3-((4-(aminomethyl)-6-(trifluoromethyl)pyridin-2-yl)oxy)phenyl)(3-fluoro-4-hydroxypyrrolidin-1-yl)methanone is used instead of Compound I. Racemic Compound I (Compound Rac-I) is depicted as follows:

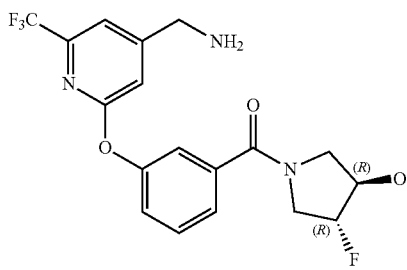
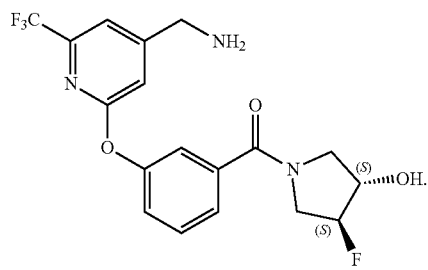

1:1 mixture

Compound I is a potent, and mechanism-based LOXL2 inhibitor. Compound I is a high affinity, selective, pseudo-irreversible, small-molecule inhibitor of LOXL2. In some embodiments, the aminomethyl pyridine moiety of Compound I interacts with the enzyme active site to form a time-dependent, pseudo-irreversible inhibitory complex. Profiling studies suggest that the two enantiomers of Compound I (i.e. (R,R) and (S,S)) are very similar to each other and to racemic Compound I in pharmacological and pharmacokinetic profile. Compound I was more potent than the (S,S)-isomer in in vitro assays. In some embodiments, Compound I was less than 2-fold more potent than the (S,S)-isomer in in vitro assays.

In some embodiments, Compound I specifically inhibits and/or binds to LOXL2. In some embodiments, Compound I specifically inhibits and/or binds to LOXL2 and does not substantially inhibit and/or bind to any other lysyl oxidase. Other lysyl oxidases include LOX, LOXL1, LOXL3, and LOXL4. In some embodiments, Compound I is specific for LOXL2. In some embodiments, Compound I inhibits the activity of LOXL2 and does not substantially inhibit the activity of LOX. In some embodiments, Compound I inhibits the activity of LOXL2 and does not substantially inhibit the activity of another lysyl oxidase-like protein.

As used herein, "selective LOXL2 inhibitor" refers to a small molecule inhibitor of LOXL2 that does not substantially inhibit and/or bind to any other lysyl oxidase. Other lysyl oxidases include LOX, LOXL1, LOXL3, and LOXL4. In some embodiments, a selective LOXL2 inhibitor does not substantially inhibit and/or bind to LOX or LOXL3. In some embodiments, a selective LOXL2 inhibitor is at least 2 times, at least 3 times, at least 4 times, at least 5 times, at least 10 times, at least 20 times, at least 30 times, at least 40 times, at least 50 times, at least 60 times, at least 70 times, at least 80 times, at least 90 times, at least 100 times, at least 120 times, at least 140 times, at least 160 times, at least 180 times, at least 200 times, at least 250 times, at least 300 times, at least 350 times, at least 400 times, at least 450 times, at least 500 times, at least 550 times, at least 600 times, at least 650 times, at least 700 times, at least 800 times, at least 900 times, or at least 1000 times more selective for LOXL2 than for LOX. In some embodiments, a selective LOXL2 inhibitor is at least 400 times more selective for LOXL2 than for LOX. In some embodiments, a selective LOXL2 inhibitor is at least 2 times, at least 3 times, at least 4 times, at least 5 times, at least 10 times, at least 20 times, at least 30 times, at least 40 times, at least 50 times, at least 60 times, at least 70 times, at least 80 times, at least 90 times, at least 100 times, at least 120 times, at least 140 times, at least 160 times, at least 180 times, at least 200 times, at least 250 times, at least 300 times, at least 350 times, at least 400 times, at least 450 times, at least 500 times, at least 550 times, at least 600 times, at least 650 times, at least 700 times, at least 800 times, at least 900 times, or at least 1000 times more selective for LOXL2 than for LOXL3. In some embodiments, a selective LOXL2 inhibitor is at least 5 times more selective for LOXL2 than for LOXL3.

In any of the embodiments disclosed herein (including methods, uses, formulations, combination therapy, etc.), Compound I, or a pharmaceutically acceptable salt or solvate thereof, is replaced with: a) Compound I, or a pharmaceutically acceptable salt or solvate thereof, of lower chiral purity; b) "(S,S)-trans-(3-((4-(aminomethyl)-6-(trifluoromethyl)pyridin-2-yl)oxy)phenyl)(3-fluoro-4-hydroxypyrrolidin-1-yl)methanone", or a pharmaceutically acceptable salt or solvate thereof of any optical purity; or c) racemic-trans-(3-((4-(aminomethyl)-6-(trifluoromethyl)pyridin-2-yl)oxy)phenyl)(3-fluoro-4-hydroxypyrrolidin-1-yl)methanone, or a pharmaceutically acceptable salt or solvate thereof.

The term "pharmaceutically acceptable salt" in reference to Compound I refers to a salt of Compound I, which does not cause significant irritation to a mammal to which it is administered and does not substantially abrogate the biological activity and properties of the compound. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviours. Also, because the salt-forming molecule can be in equilibrium with a neutral form, passage through biological membranes can be adjusted.

It should be understood that a reference to a pharmaceutically acceptable salt includes the solvent addition forms (solvates). Solvates contain either stoichiometric or non-stoichiometric amounts of a solvent, and are formed during the process of product formation or isolation with pharmaceutically acceptable solvents such as water, ethanol, methyl tert-butyl ether, isopropanol, acetonitrile, heptane, and the like. In one aspect, solvates are formed using, but not limited to, Class 3 solvent(s). Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005). Hydrates are formed when the solvent is water, or alcoholates are formed when the solvent is alcohol. In one embodiment, solvates of Compound I, or pharmaceutically acceptable salts thereof, are conveniently prepared or formed during the processes of preparing Compound I, or pharmaceutically acceptable salts thereof. In addition, Compound I, or pharmaceutically acceptable salts thereof, exist in unsolvated form. In some embodiments, Compound I, or a pharmaceutically acceptable salt thereof, is hydrated.

A wide variety of pharmaceutically acceptable salts are formed from Compound I and include:
  salts formed when Compound I (i.e. free base form) is treated with an inorganic acid. Inorganic acids include, but are not limited to, hydrochloric acid, hydrobromic acid, sulfuric acid, phosphoric acid, nitric acid, and metaphosphoric acid;
  salts formed when Compound I (i.e. free base form) is treated with an organic acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; monomethyl fumarate, naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

Pharmaceutically acceptable salts of Compound I include the hydrochloride salt, sulfate salt, mesylate salt, maleate salt, phosphate salt, L-tartrate salt, fumarate salt, succinate salt, or acetate salt. In some embodiments, the pharmaceutically acceptable salt is the hydrochloride salt. In some embodiments, the pharmaceutically acceptable salt is the sulfate salt. In some embodiments, the pharmaceutically acceptable salt is the mesylate salt. In some embodiments, the pharmaceutically acceptable salt is the maleate salt. In some embodiments, the pharmaceutically acceptable salt is the phosphate salt. In some embodiments, the pharmaceutically acceptable salt is the L-tartrate salt. In some embodiments, the pharmaceutically acceptable salt is the fumarate salt. In some embodiments, the pharmaceutically acceptable salt is the succinate salt. In some embodiments, the pharmaceutically acceptable salt is the acetate salt.

In some embodiments, Compound I is treated with sulfuric acid in a solvent to form the corresponding sulfate salt. In some embodiments, Compound I is treated with phosphoric acid in a solvent to form the corresponding phosphate salt. In some embodiments, Compound I is treated with L-tartaric acid in a solvent to form the corresponding L-tartrate salt. In some embodiments, Compound I is treated with citric acid in a solvent to form the corresponding citrate salt. In some embodiments, the solvent is acetonitrile or ethanol.

In some embodiments, the pharmaceutically acceptable salt is amorphous. In some embodiments, the pharmaceutically acceptable salt is crystalline.

In some embodiments, Compound I described herein is prepared as a chloride salt, sulfate salt, bromide salt, mesylate salt, maleate salt, citrate salt or phosphate salt. In some embodiments, Compound I described herein is prepared as a hydrochloride salt. In some embodiments, a Compound I described herein is prepared as a mesylate salt.

As used herein, "MsO−" is an abbreviation for the methanesulfonate anion, $CH_3S(O)_2O^-$.

(R,R)-trans-(3-((4-(Aminomethyl)-6-(trifluoromethyl)pyridin-2-yl)oxy)phenyl)(3-fluoro-4-hydroxypyrrolidin-1-yl)methanone, hydrochloride salt
(Compound 1)

"Compound 1" or "(R,R)-trans-(3-((4-(aminomethyl)-6-(trifluoromethyl)pyridin-2-yl)oxy)phenyl)(3-fluoro-4-hydroxypyrrolidin-1-yl)methanone, hydrochloride salt" or "(3-((4-(aminomethyl)-6-(trifluoromethyl)-pyridin-2-yl)oxy)phenyl)(3R,4R)-3-fluoro-4-hydroxypyrrolidin-1-yl) methanone, hydrochloride salt", or any other similar name refers to the compound with the following structure:

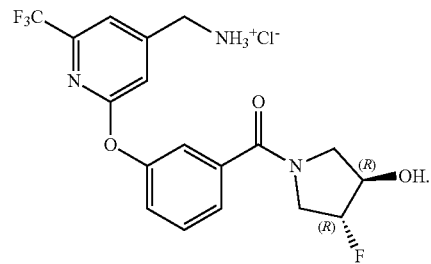

The (S,S)-enantiomer of Compound 1 (Compound Ent-1) has the following structure:

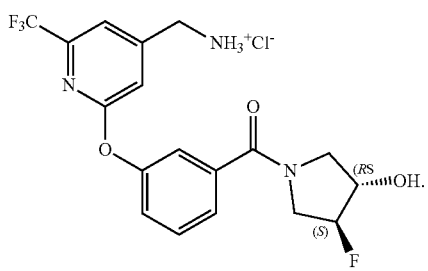

Racemic Compound 1 (Compound Rac-1) is depicted as follows:

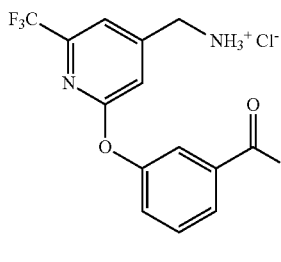 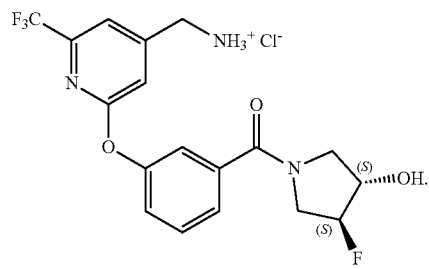

1:1 mixture

Amorphous Compound 1

In some embodiments, Compound 1 is amorphous. In some embodiments, the amorphous phase of Compound 1 has an XRPD pattern showing a lack of crystallinity.

Amorphous Compound 1 deliquesces at 40° C./75% RH.

Form 1 of Compound 1

Figure 9:
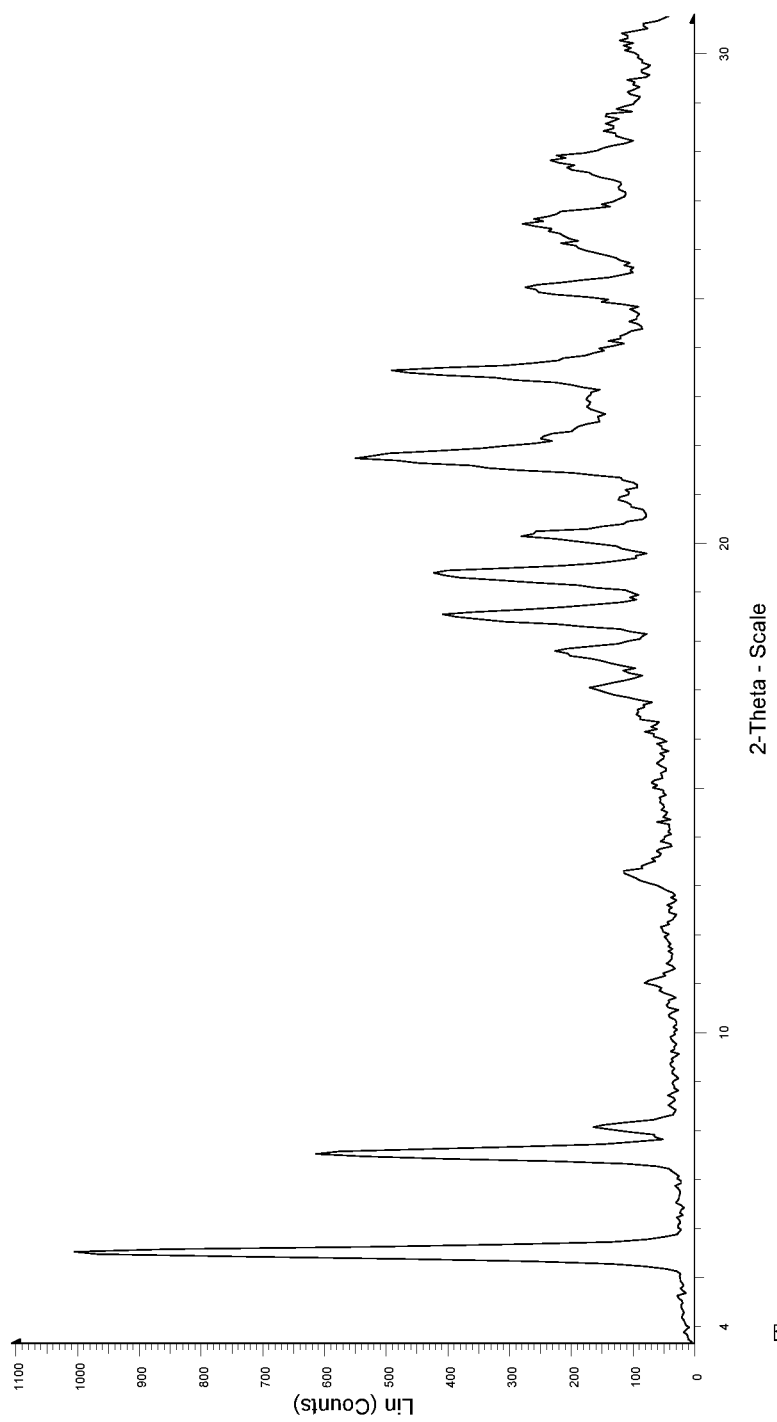
FIG. 9 illustrates the X-ray powder diffraction pattern for Form 1 of Compound 1.
Figure 10:
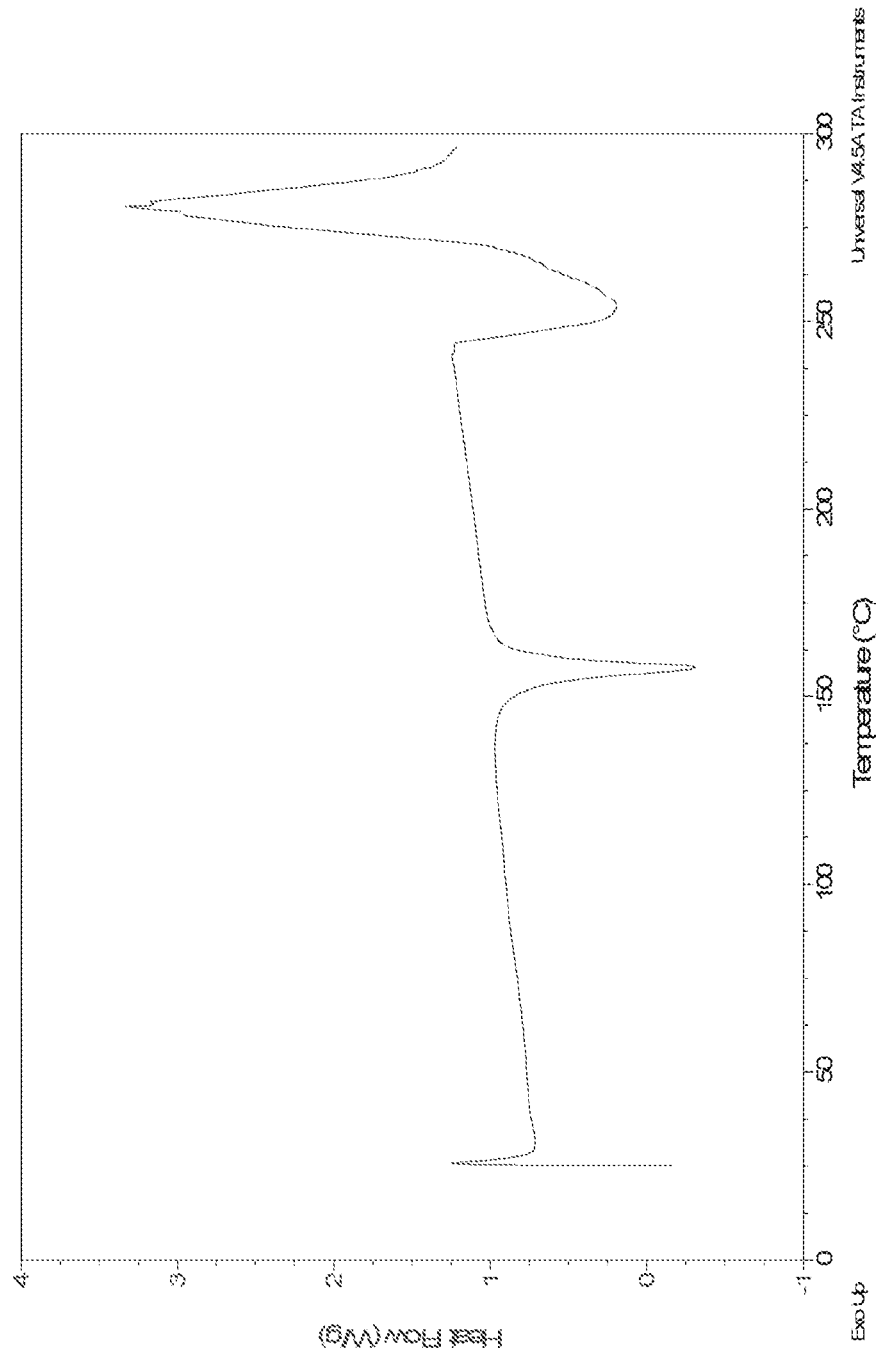
FIG. 10 illustrates a representative DSC thermogram for Form 1 of Compound 1.

In some embodiments, Compound 1 is crystalline. In some embodiments, Compound 1 is crystalline Form 1. In some embodiments, Compound 1 is crystalline Form 1 and has at least one of the following properties:
(a) an X-ray powder diffraction (XRPD) pattern with characteristic peaks at 5.5° 2-Theta, 7.5° 2-Theta, 18.5° 2-Theta, 19.4° 2-Theta, 21.8° 2-Theta, 23.5° 2-Theta;
(b) an X-ray powder diffraction (XRPD) pattern substantially the same as shown in FIG. 9;
(c) a DSC thermogram with an endotherm at about 153° C.; or
(d) a DSC thermogram substantially the same as shown in FIG. 10.

In some embodiments, Compound 1 is crystalline Form 1 and has at least properties selected from the group consisting of (a), (b), (c), and (d). In some embodiments, Compound 1 is crystalline Form 1 and has at three properties selected from the group consisting of (a), (b), (c), and (d). In some embodiments, Compound 1 is crystalline Form 1 and has properties (a), (b), (c), and (d).

In some embodiments, Compound 1 is crystalline and has an X-ray powder diffraction (XRPD) pattern with characteristic peaks at 5.5° 2-Theta, 7.5° 2-Theta, 18.5° 2-Theta, 19.4° 2-Theta, 21.8° 2-Theta, 23.5° 2-Theta.

In some embodiments, Compound 1 is crystalline and has an X-ray powder diffraction (XRPD) pattern substantially the same as shown in FIG. 9.

In some embodiments, Compound 1 is crystalline and has a DSC thermogram with an endotherm at about 153° C.

In some embodiments, Compound 1 is crystalline and has a DSC thermogram substantially the same as shown in FIG. 10.

In some embodiments, Compound 1 is crystalline Form 1 and is obtained from a solution of tetrahydrofuran, ethyl acetate, acetonitrile, dimethoxyethane, or tetrahydrofuran/water (95:5).

Form 1 is a hygroscopic solid, which transforms to Form 2 when stored at 40° C./75% RH for one week.

Form 2 of Compound 1

Figure 11:
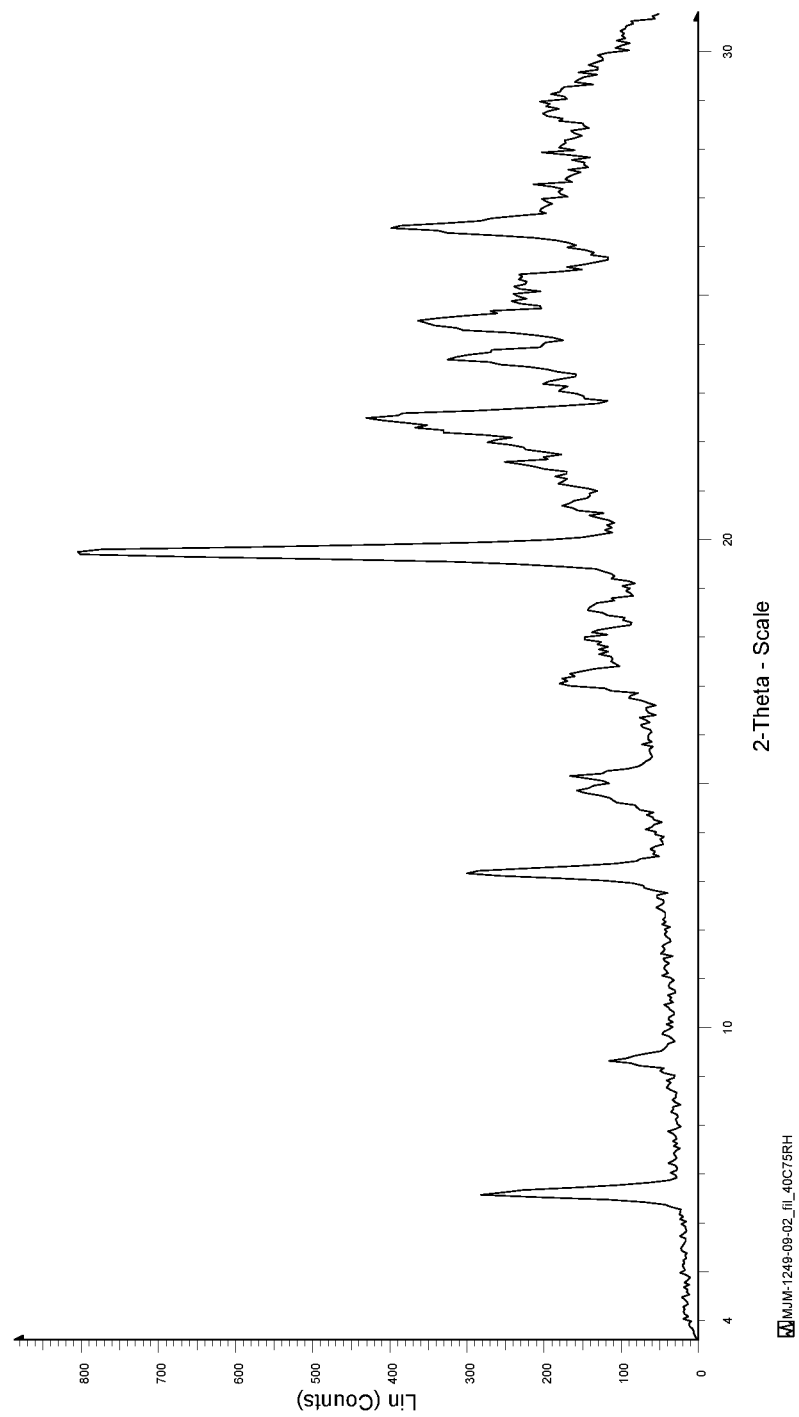
FIG. 11 illustrates the X-ray powder diffraction pattern for Form 2 of Compound 1.
Figure 12:
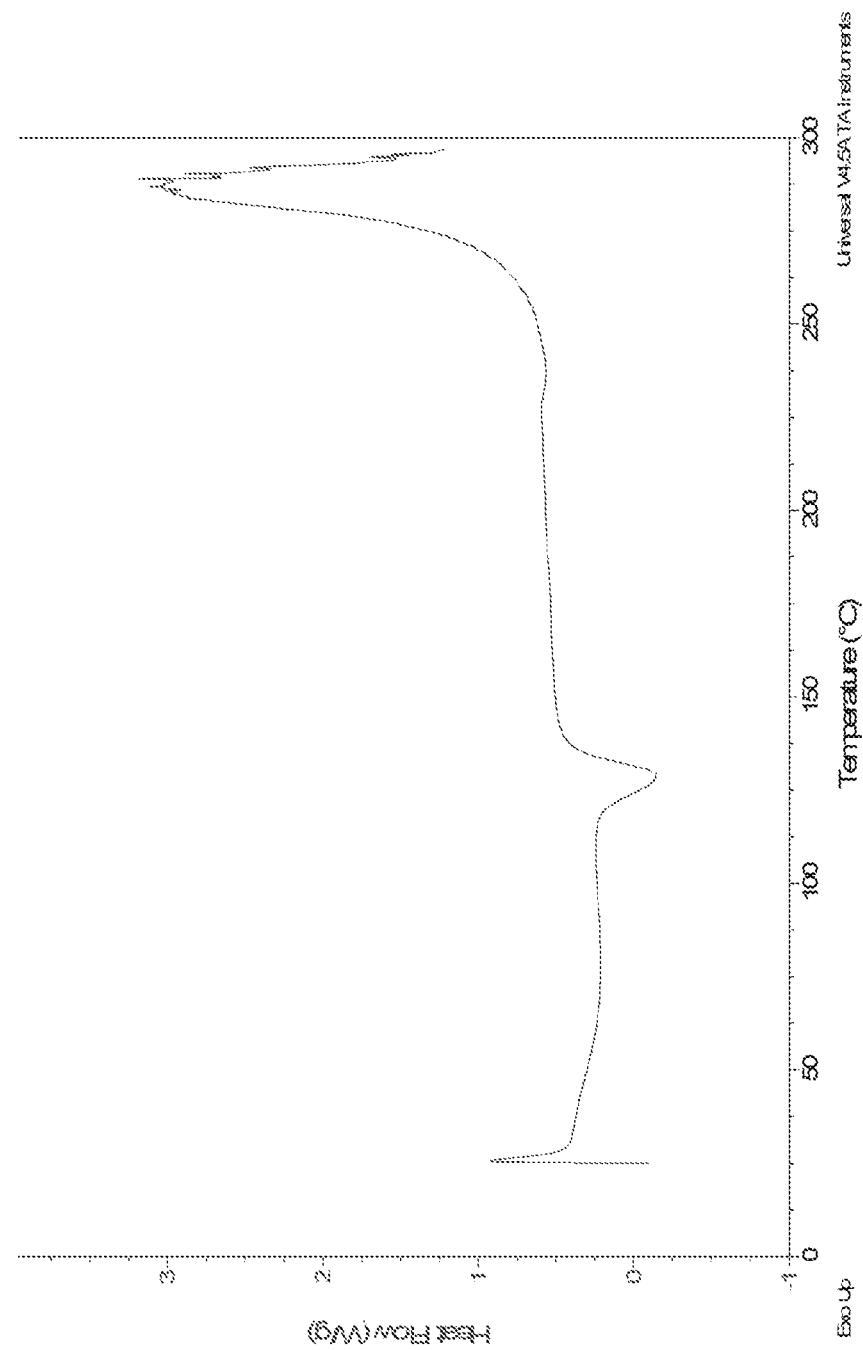
FIG. 12 illustrates a representative DSC thermogram for Form 2 of Compound 1.

In some embodiments, Compound 1 is crystalline. In some embodiments, Compound 1 is crystalline Form 2. In some embodiments, Compound 1 is crystalline Form 2 and has at least one of the following properties:
(a) an X-ray powder diffraction (XRPD) pattern with characteristic peaks at 6.6° 2-Theta, 13.2° 2-Theta, 19.7° 2-Theta, 22.3° 2-Theta, 22.5° 2-Theta, 23.7° 2-Theta, 24.5° 2-Theta, 26.4° 2-Theta;
(b) an X-ray powder diffraction (XRPD) pattern substantially the same as shown in FIG. 11;
(c) a DSC thermogram with endotherms at about 43° C. and about 119° C.; or
(d) a DSC thermogram substantially the same as shown in FIG. 12.

In some embodiments, Compound 1 is crystalline Form 2 and has at least properties selected from the group consisting of (a), (b), (c), and (d). In some embodiments, Compound 1 is crystalline Form 2 and has at three properties selected from the group consisting of (a), (b), (c), and (d). In some embodiments, Compound 1 is crystalline Form 2 and has properties (a), (b), (c), and (d).

In some embodiments, Compound 1 is crystalline and has an X-ray powder diffraction (XRPD) pattern with characteristic peaks at 6.6° 2-Theta, 13.2° 2-Theta, 19.7° 2-Theta, 22.3° 2-Theta, 22.5° 2-Theta, 23.7° 2-Theta, 24.5° 2-Theta, 26.4° 2-Theta.

In some embodiments, Compound 1 is crystalline and has an X-ray powder diffraction (XRPD) pattern substantially the same as shown in FIG. 11.

In some embodiments, Compound 1 is crystalline and has a DSC thermogram with endotherms at about 43° C. and about 119° C.

In some embodiments, Compound 1 is crystalline and has a DSC thermogram substantially the same as shown in FIG. 12.

Form 2 is thermally stable but converts over time to a waxy solid not suitable for manufacturing.

Synthesis of Compound 1

In some embodiments, Compound 1 is prepared via the synthetic route that uses chiral separation following scheme below:

Scheme 1. Preparation via Chiral Separation

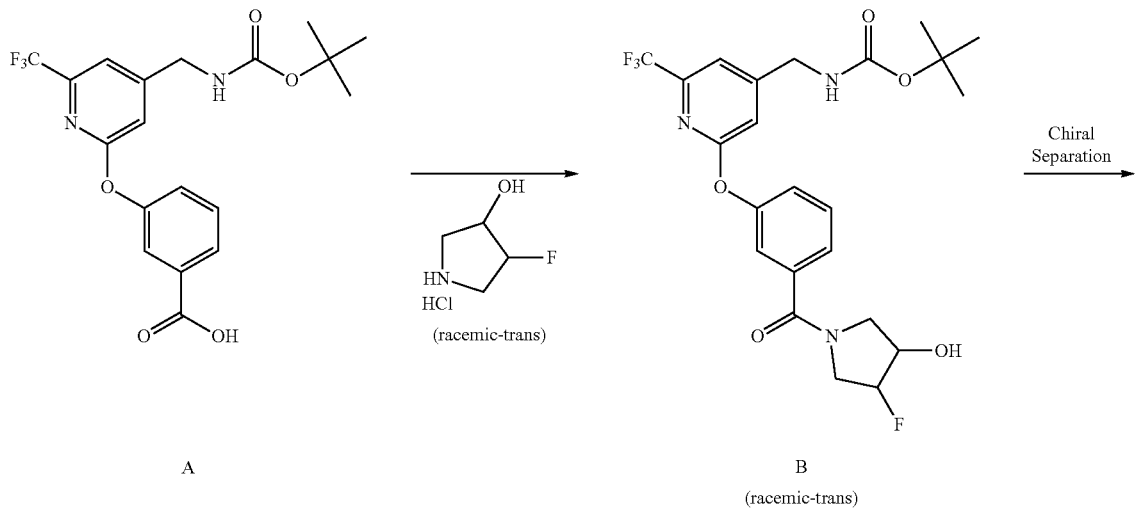

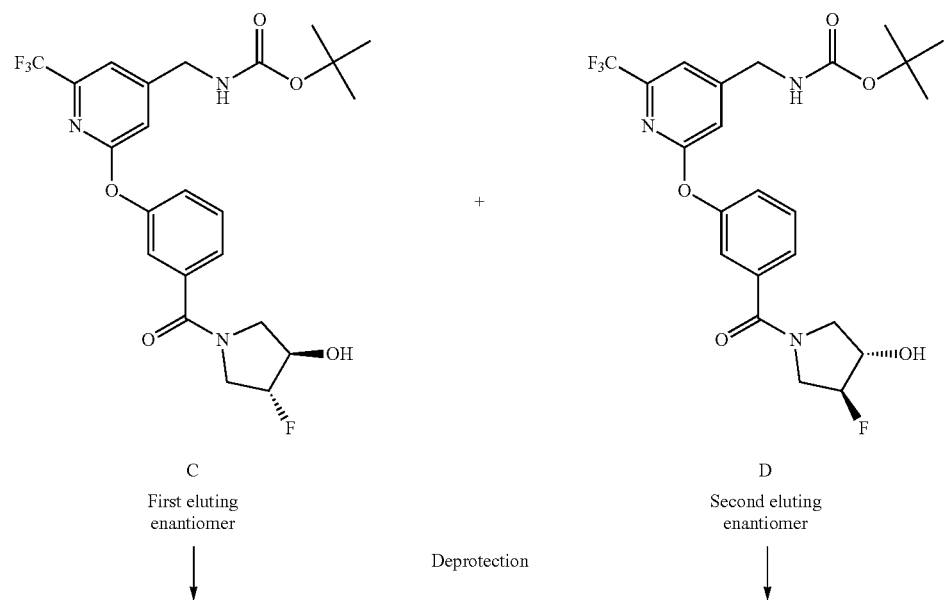

C
First eluting enantiomer

D
Second eluting enantiomer

Deprotection

23

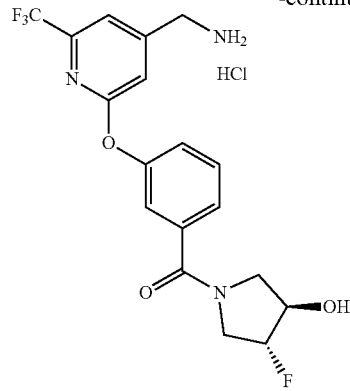

1

24

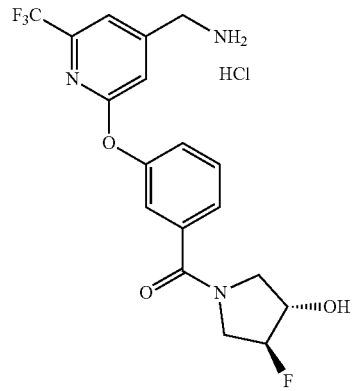

Ent-1

As shown in the above scheme, in some embodiments, 3-(4-((tert-butoxycarbonylamino)methyl)-6-(trifluoromethyl)pyridin-2-yloxy)benzoic acid (Compound A) is treated under appropriate coupling conditions with racemic trans-4-fluoro-3-hydroxypyrrolidine hydrochloride to provide racemic-trans-tert-butyl((2-(3-(3-fluoro-4-hydroxypyrrolidine-1-carbonyl)phenoxy)-6-(trifluoromethyl)pyridin-4-yl)methyl)carbamate (Compound B).

In some embodiments, appropriate coupling conditions include the use of EDC, DCC, BOP, HATU or the like. In some embodiments, the appropriate coupling conditions include the use of a base. In some embodiments, the base is an organic base. In some embodiments, the base is a hindered base such as trimethylamine (TEA), diisopropylethylamine (DIEA or DIPEA), N-methylmorpholine, pyridine or the like. In some embodiments, the appropriate coupling conditions include the use of a solvent. Suitable solvents include dichloromethane, dichloroethane, tetrahydrofuran, dimethoxyethane or the like. In some embodiments, appropriate coupling conditions include HATU and DIEA in DCM/DMF at room temperature. In some embodiments, racemic-trans-tert-butyl ((2-(3-(3-fluoro-4-hydroxypyrrolidine-1-carbonyl)phenoxy)-6-(trifluoromethyl)pyridin-4-yl)methyl)carbamate (Compound B) is separated into individual enantiomers using appropriate chiral HPLC methods to provide tert-butyl (2-(3-((3R,4R)-3-fluoro-4-hydroxypyrrolidine-1-carbonyl)phenoxy)-6-(trifluoromethyl)pyridin-4-yl)methylcarbamate (Compound C). tert-Butyl (2-(3-((3R,4R)-3-fluoro-4-hydroxypyrrolidine-1-carbonyl)phenoxy)-6-(trifluoromethyl)pyridin-4-yl) methylcarbamate (Compound C) is treated with a suitable acid in a suitable solvent to provide (R,R)-trans-(3-((4-(aminomethyl)-6-(trifluoromethyl)pyridin-2-yl)oxy)phenyl) (3-fluoro-4-hydroxypyrrolidin-1-yl)methanone, hydrochloride salt (Compound 1). In some embodiments, the suitable acid is hydrochlodic acid (HCl), methanesulfonic acid, trifluoroacetic acid, benzensulfonic acid or tolunesulfonic acid. In some embodiments, the suitable acid is hydrochlodic acid (HCl). In some embodiments, the suitable solvent is diethylether (Et$_2$O).

In some embodiments, Compound 1 is prepared via the synthetic route that following scheme below:

Scheme 2. Preparation of Compound 1 without Chiral Separation.

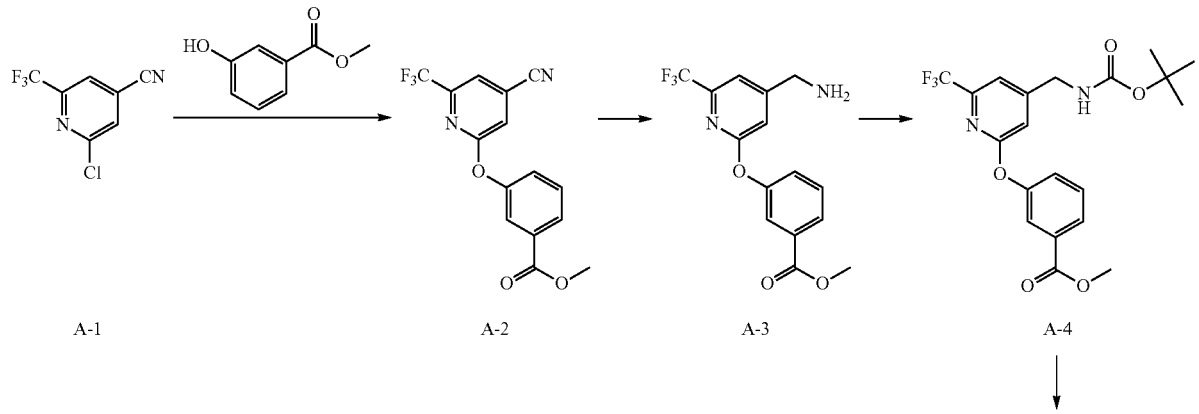

A-1   A-2   A-3   A-4

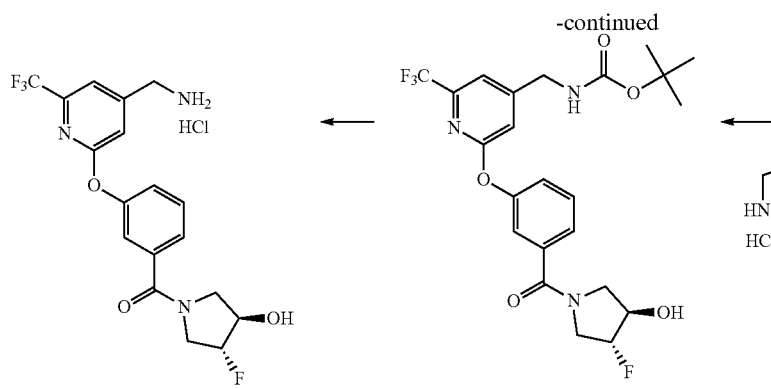

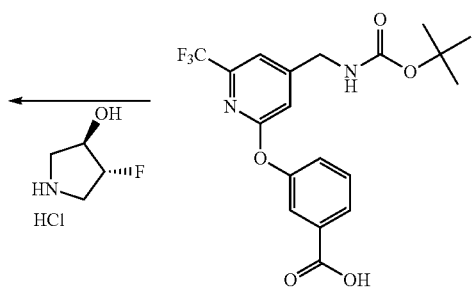

As shown in the scheme above, in some embodiments, 2-chloro-6-(trifluoromethyl)isonicotinonitrile (Compound A-1) is subjected under appropriate reaction conditions to provide methyl 3-((4-cyano-6-(trifluoromethyl)pyridin-2-yl)oxy)benzoate (Compound A-2). In some embodiments, appropriate reaction conditions include nucleophilic aromatic substitution (SNAr) reaction conditions. A nucleophilic aromatic substitution is a substitution reaction in which the nucleophile displaces a good leaving group, such as a halide, on an aromatic ring. In some embodiments, appropriate reaction conditions include methyl 3-hydroxybenzoate with $K_2CO_3$ in THF/DMF.

Methods of forming aromatic ethers include those described herein or described in the art including but not limited to the Ulman Ether synthesis, Chan-Lam coupling, and Buchwald-Hartwig synthesis (D. Ma, Q. Cai, *Org. Lett.*, 2003, 5, 3799-3802; C. G. Bates, et al., *Org. Lett.*, 2002, 4, 2803-2806; C. H. Burgos, et al., *Angew. Chem. Int. Ed.*, 2006, 45, 4321-4326; C. H. Burgos, et al., *Angew. Chem. Int. Ed.*, 2006, 45, 4321-4326; D. M. T. Chan, et al., *Tetrahedron Lett.*, 1998, 39, 2933-2936; Z. Liu, R. C. Larock, *J. Org. Chem.*, 2006, 71, 3198-3209; Y.-J. Chen, H.-H. Chen, *Org. Lett.*, 2006, 8, 5609-5612; F. Li, Q. et al., *Org. Lett.*, 2003, 5, 2169-2171; D. A. Evans, et al., *Tetrahedron Letters*, 1998, 39, 2937-2940; C.-E. Yeom, et al., *Synlett*, 2007, 146-150).

In some embodiments, methyl 3-((4-cyano-6-(trifluoromethyl)pyridin-2-yl)oxy)benzoate (Compound A-2) is treated with $CoCl_2$ and $NaBH_4$ under suitable reaction conditions to provide methyl 3-((4-(aminomethyl)-6-(trifluoromethyl)pyridin-2-yl)oxy)benzoate (Compound A-3). In some embodiments, the suitable reaction conditions include THF/MeOH at 0° C. In some embodiments, methyl 3-((4-(aminomethyl)-6-(trifluoromethyl)pyridin-2-yl)oxy)benzoate (Compound A-3) is converted to methyl 3-(4-(((tert-butoxycarbonyl)amino)methyl)-6-(trifluoromethyl)pyridin-2-yl)oxy)benzoate (Compound A-4) with di-tert-butyl dicarbonate. In some embodiments, methyl 3-((4-(((tert-butoxycarbonyl)amino)methyl)-6-(trifluoromethyl)pyridin-2-yl)oxy)benzoate (Compound A-4) is hydrolyzed to the corresponding acid, 3-((4-(((tert-butoxycarbonyl)amino)methyl)-6-(trifluoromethyl)pyridin-2-yl)oxy)benzoic acid (Compound A-5), via treatment with LiOH. In some embodiments, 3-((4-(((tert-butoxycarbonyl)amino)methyl)-6-(trifluoromethyl)pyridin-2-yl)oxy)benzoic acid (Compound A-5) is treated with (3R,4R)-4-fluoropyrrolidin-3-ol hydrochloride to provide tert-butyl ((2-(3-((3R,4R)-3-fluoro-4-hydroxypyrrolidine-1-carbonyl)phenoxy)-6-(trifluoromethyl)pyridin-4-yl)methyl)carbamate (Compound C) under suitable reaction conditions. In some embodiments, suitable reaction conditions include HATU and DIPEA in DCM/DMF. In some embodiments, tert-butyl ((2-(3-((3R,4R)-3-fluoro-4-hydroxypyrrolidine-1-carbonyl)phenoxy)-6-(trifluoromethyl)pyridin-4-yl)methyl)carbamate (Compound C) is treated under appropriate acidic reaction conditions to provide (3-((4-(aminomethyl)-6-(trifluoromethyl)pyridin-2-yl)oxy)phenyl)((3R,4R)-3-fluoro-4-hydroxypyrrolidin-1-yl)methanone, hydrochloride salt (Compound 1). In some embodiments, appropriate reaction conditions include HCl/MTBE in DCM.

In some embodiments, samples of Compound 1 are greater than 90% pure. In some embodiments, samples of Compound 1 are greater than 95% pure, greater than 96% pure, greater than 97% pure, greater than 98% pure, or greater than 99% pure.

In some embodiments, samples of Compound 1 have a chiral purity of greater than 90%. In some embodiments, samples of Compound 1 have a chiral purity of greater than 95%, greater than 96%, greater than 97%, greater than 98%, or greater than 99%.

In some embodiments, samples of Compound 1 include a detectable amount of the (S,S)-enantiomer of Compound 1.

In some embodiments, samples of Compound 1 contain less than 5% of (3R,4R)-4-fluoropyrrolidin-3-ol. In some embodiments, samples of Compound 1 contain less 5%, 4%, 3%, 2%, or 1% of (3R,4R)-4-fluoropyrrolidin-3-ol.

(R,R)-trans-(3-((4-(Aminomethyl)-6-(trifluoromethyl)pyridin-2-yl)oxy)phenyl)(3-fluoro-4-hydroxypyrrolidin-1-yl)methanone, methanesulfonate salt (Compound 2)

"Compound 2" or "(R,R)-trans-(3-((4-(aminomethyl)-6-(trifluoromethyl)pyridin-2-yl)oxy)phenyl)(3-fluoro-4-hydroxypyrrolidin-1-yl)methanone, methanesulfonate salt" or "(3-((4-(aminomethyl)-6-(trifluoromethyl)-pyridin-2-yl)oxy)phenyl)(3R,4R)-3-fluoro-4-hydroxypyrrolidin-1-yl)methanone, methanesulfonate salt", or any other similar name (e.g. Compound 2, mesylate salt) refers to the compound with the following structure:

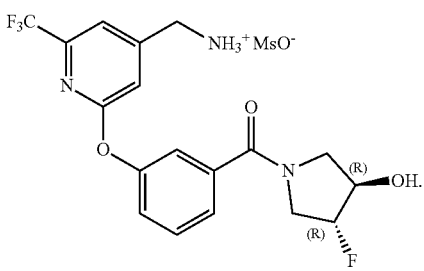

The (S,S)-enantiomer of Compound 2 (Compound Ent-2) has the following structure:

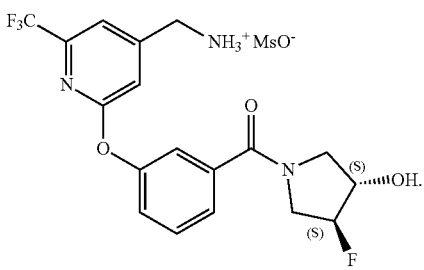

Racemic Compound 2 (Compound Rac-2) is depicted as follows:

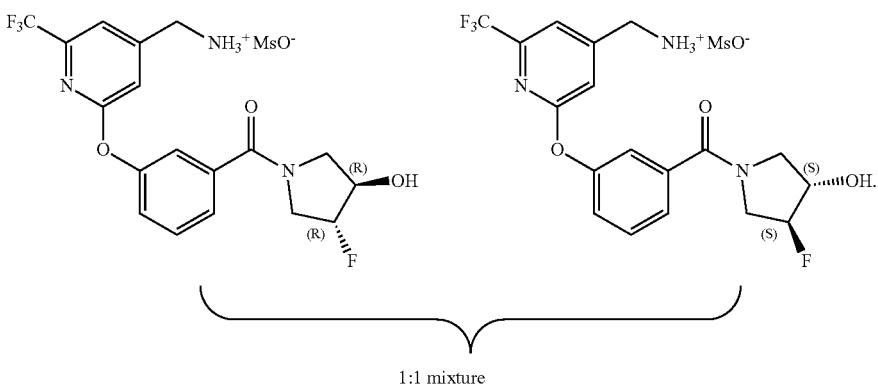

1:1 mixture

Amorphous Compound 2

In some embodiments, Compound 2 is amorphous. In some embodiments, the amorphous phase of Compound 2 has an XRPD pattern showing a lack of crystallinity.

Form 1 of Compound 2

Figure 2:
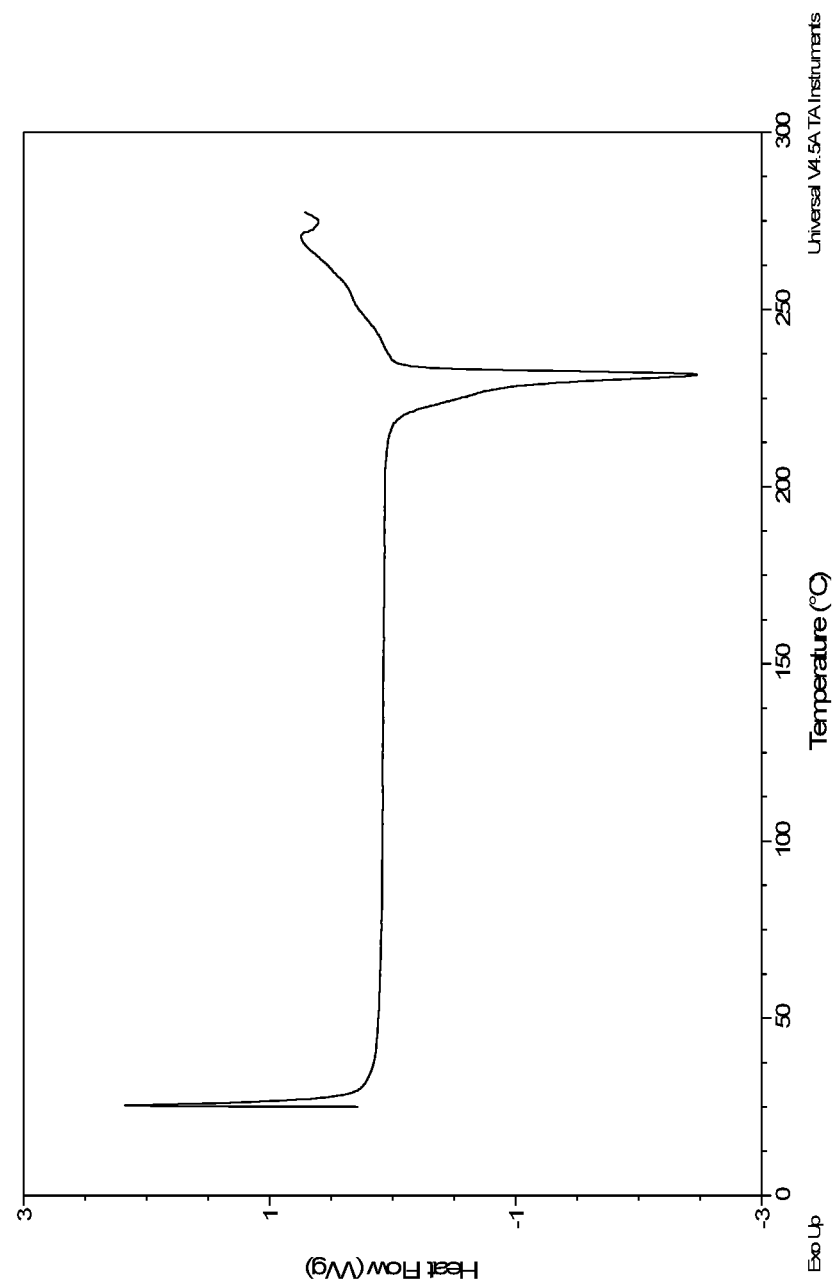
FIG. 2 illustrates a representative DSC thermogram for Form 1 of Compound 2.

In some embodiments, Compound 2 is crystalline. In some embodiments, Compound 2 is crystalline Form 1. In some embodiments, Compound 2 is crystalline Form 1 and has at least one of the following properties:
  (a) an X-ray powder diffraction (XRPD) pattern with characteristic peaks at 13.6° 2-Theta, 16.9° 2-Theta, 19.4° 2-Theta, 20.1° 2-Theta, 20.3° 2-Theta, 20.6° 2-Theta, 23.1° 2-Theta, 23.6° 2-Theta;
  (b) an X-ray powder diffraction (XRPD) pattern substantially the same as shown in FIG. 1;
  (c) a DSC thermogram with endotherms at about 231° C. and about 236° C.; or
  (d) a DSC thermogram substantially the same as shown in FIG. 2;
  (e) reversible water uptake (~2.1% w/w) between 0 and 90% RH;
  (f) an unchanged XRPD after the GVS analysis.

In some embodiments, Compound 2 is crystalline Form 1 and has at least properties selected from the group consisting of (a), (b), (c), (d), (e), and (f). In some embodiments, Compound 2 is crystalline Form 1 and has at three properties selected from the group consisting of (a), (b), (c), (d), (e), and (f). In some embodiments, Compound 2 is crystalline Form 1 and has at four properties selected from the group consisting of (a), (b), (c), (d), (e), and (f). In some embodiments, Compound 2 is crystalline Form 1 and has at five properties selected from the group consisting of (a), (b), (c), (d), (e), and (f). In some embodiments, Compound 2 is crystalline Form 1 and has properties (a), (b), (c), (d), (e), and (0.

In some embodiments, Compound 2 is crystalline and has an X-ray powder diffraction (XRPD) pattern with characteristic peaks at 13.6° 2-Theta, 16.9° 2-Theta, 19.4° 2-Theta, 20.1° 2-Theta, 20.3° 2-Theta, 20.6° 2-Theta, 23.1° 2-Theta, 23.6° 2-Theta.

In some embodiments, Compound 2 is crystalline and has an X-ray powder diffraction (XRPD) pattern substantially the same as shown in FIG. 1.

In some embodiments, Compound 2 is crystalline and has a DSC thermogram with endotherms at about 231° C. and about 236° C.

In some embodiments, Compound 2 is crystalline and has a DSC thermogram substantially the same as shown in FIG. 2.

In some embodiments, Compound 2 is crystalline and has reversible water uptake (~2.1% w/w) between 0 and 90% RH.

In some embodiments, Compound 2 is crystalline and has an unchanged XRPD after the GVS analysis.

In some embodiments, Compound 2 is crystalline Form 1 and is obtained from a solution of ethanol or acetonitrile.

Form 2 of Compound 2

Figure 3:
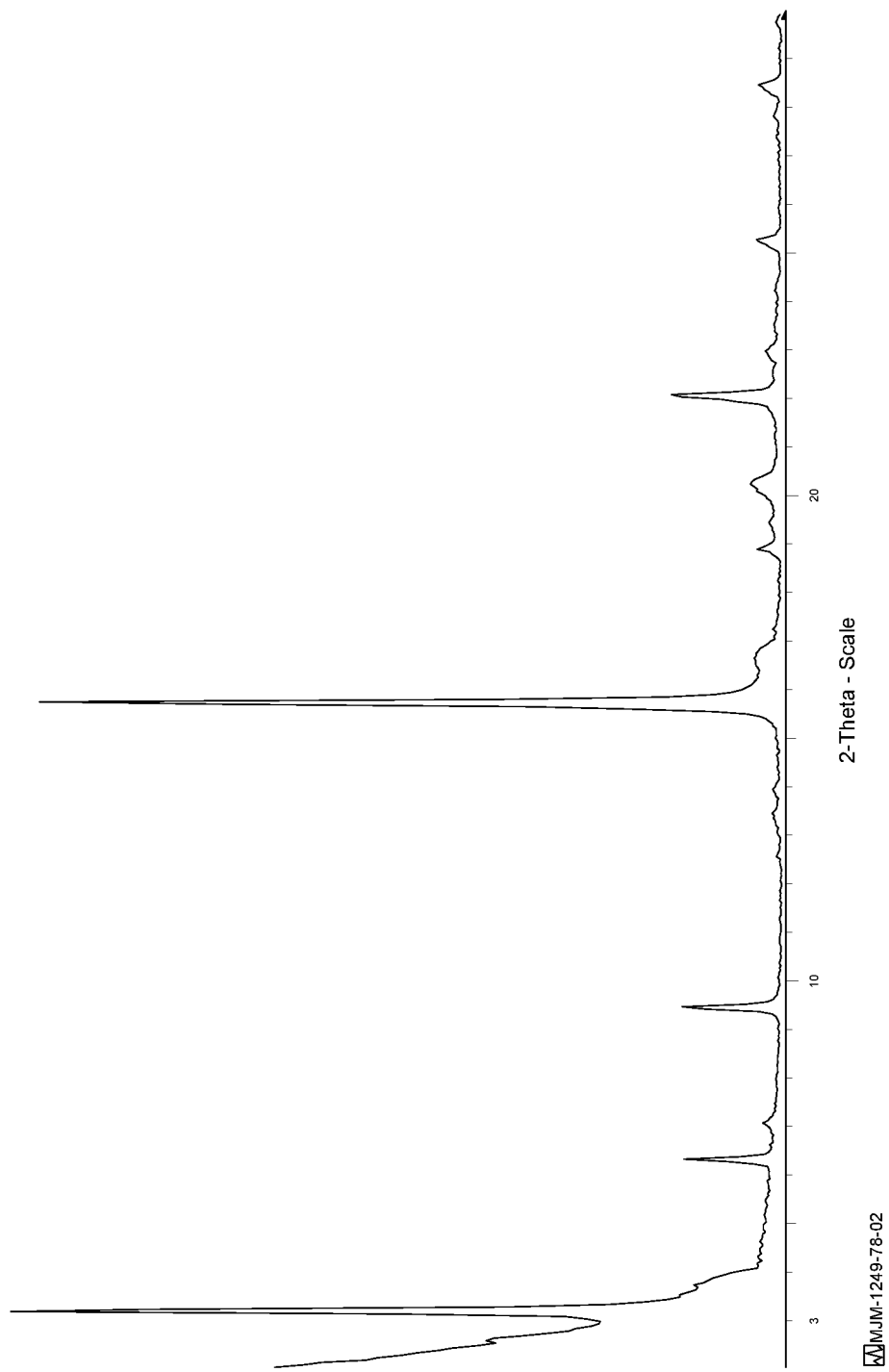
FIG. 3 illustrates the X-ray powder diffraction pattern for Form 2 of Compound 2.
Figure 4:
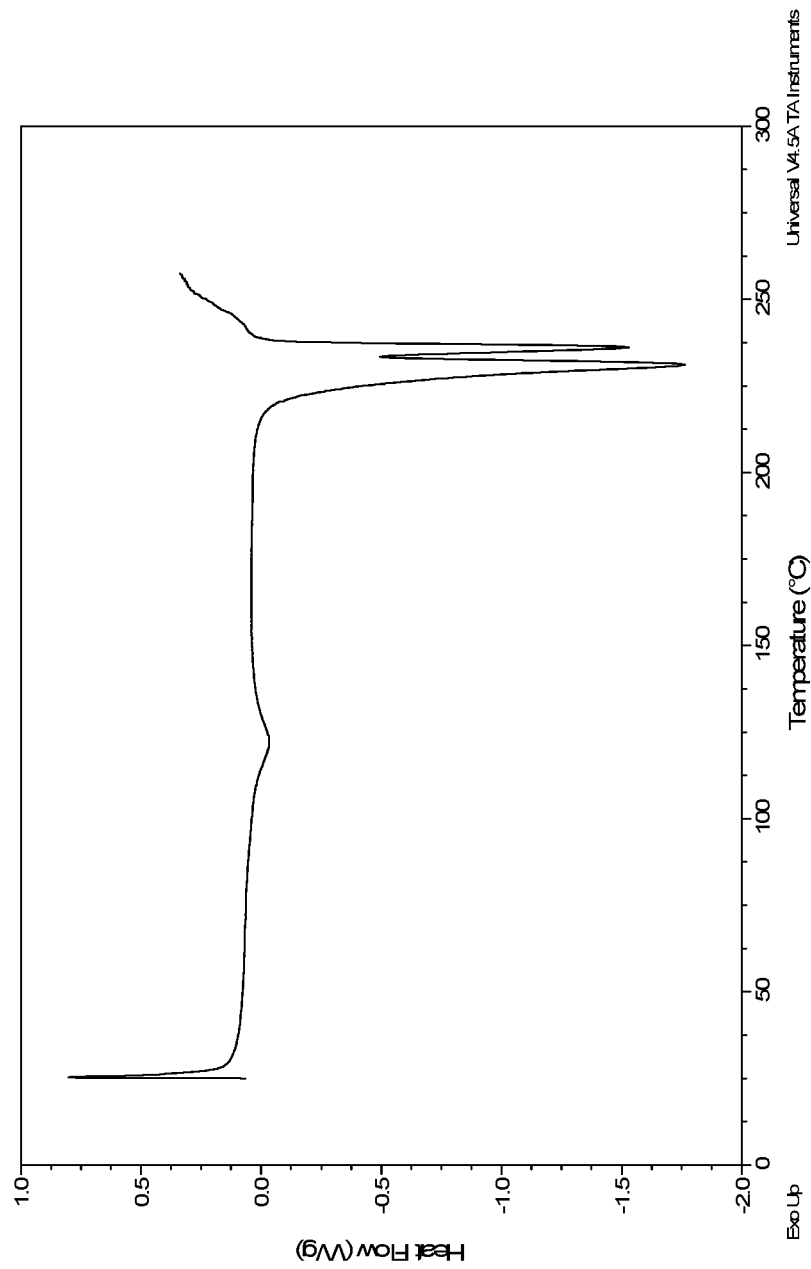
FIG. 4 illustrates a representative DSC thermogram for Form 2 of Compound 2.

In some embodiments, Compound 2 is crystalline. In some embodiments, Compound 2 is crystalline Form 2. In some embodiments, Compound 2 is crystalline Form 2 and has at least one of the following properties:
  (a) an X-ray powder diffraction (XRPD) pattern with characteristic peaks at 2.6° 2-Theta, 3.2° 2-Theta, 6.3° 2-Theta, 9.4° 2-Theta, 15.7° 2-Theta, 22.1° 2-Theta;
  (b) an X-ray powder diffraction (XRPD) pattern substantially the same as shown in FIG. 3;
  (c) a DSC thermogram with three endotherms at about 121.7° C., 231.1° C. and 236.1° C.;

(d) a DSC thermogram substantially the same as shown in FIG. 4;
(e) is anhydrous;
(f) transformation to Compound 2, Form 1 when heated above 150° C.;
(g) transformation to Compound 2, Form 1 after GVS analysis and 7 days at 40° C./75% RH;
(h) transformation to Compound 2, Form 1 after 7 days at 25° C./97% RH.

In some embodiments, Compound 2 is crystalline Form 2 and has at least two properties selected from the group consisting of (a), (b), (c), (d), (e), (f), (g), and (h). In some embodiments, Compound 2 is crystalline Form 2 and has at three properties selected from the group consisting of (a), (b), (c), (d), (e), (f), (g), and (h). In some embodiments, Compound 2 is crystalline Form 2 and has at least four properties selected from the group consisting of (a), (b), (c), (d), (e), (f), (g), and (h). In some embodiments, Compound 2 is crystalline Form 2 and has at five properties selected from the group consisting of (a), (b), (c), (d), (e), (f), (g), and (h). In some embodiments, Compound 2 is crystalline Form 2 and has at least six properties selected from the group consisting of (a), (b), (c), (d), (e), (f), (g), and (h). In some embodiments, Compound 2 is crystalline Form 2 and has at least seven properties selected from the group consisting of (a), (b), (c), (d), (e), (f), (g), and (h). In some embodiments, Compound 2 is crystalline Form 2 and has properties (a), (b), (c), (d), (e), (f), (g), and (h).

Form 2 converts to Form 1 in humidity.

In some embodiments, Compound 2 is crystalline and has an X-ray powder diffraction (XRPD) pattern with characteristic peaks at 2.6° 2-Theta, 3.2° 2-Theta, 6.3° 2-Theta, 9.4° 2-Theta, 15.7° 2-Theta, 22.1° 2-Theta.

In some embodiments, Compound 2 is crystalline and has an X-ray powder diffraction (XRPD) pattern substantially the same as shown in FIG. 3.

In some embodiments, Compound 2 is crystalline and has a DSC thermogram with three endotherms at about 121.7° C., 231.1° C. and 236.1° C.

In some embodiments, Compound 2 is crystalline and has a DSC thermogram substantially the same as shown in FIG. 4.

In some embodiments, Compound 2 is crystalline and is anhydrous.

In some embodiments, Compound 2 is crystalline Form 2 and is obtained from a solution of ethanol and n-heptane.

Form 3 of Compound 2

Figure 5:
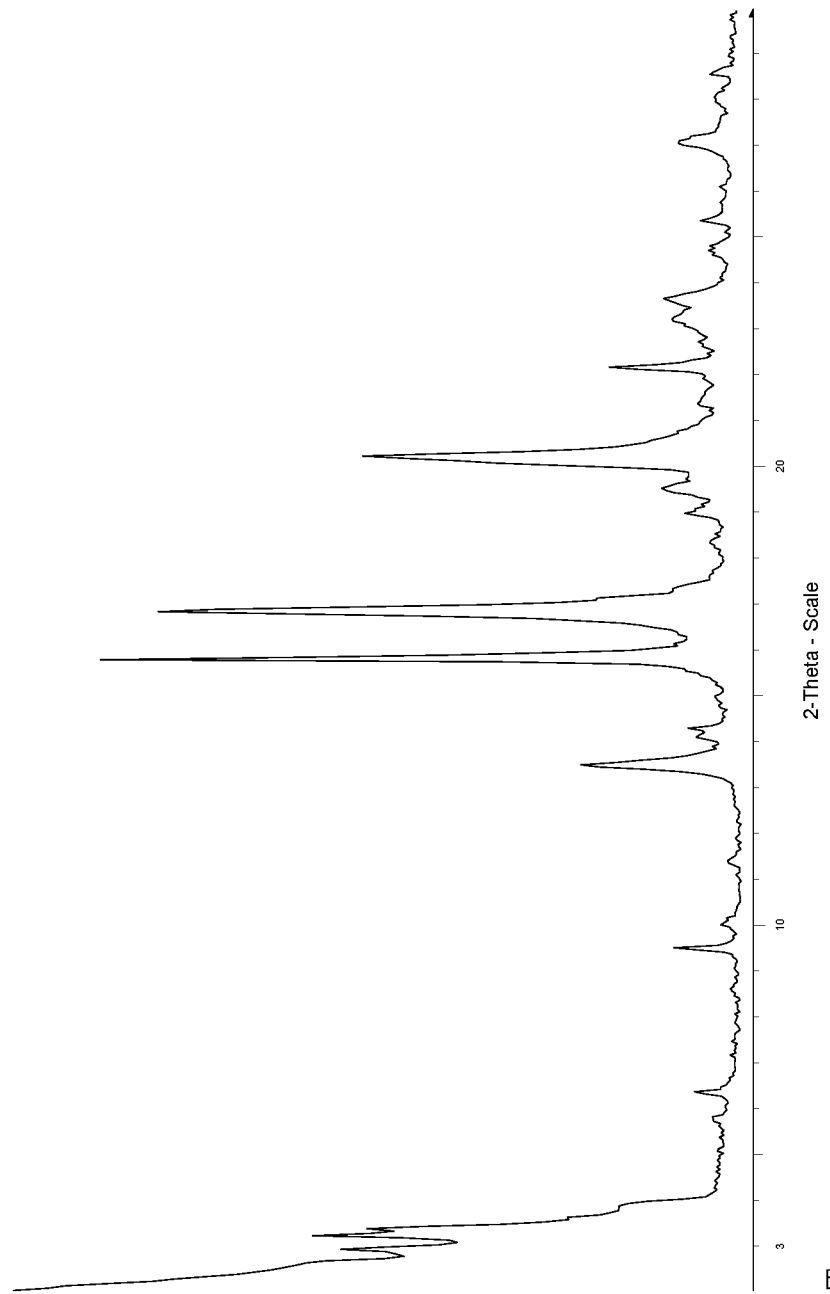
FIG. 5 illustrates the X-ray powder diffraction pattern for Form 3 of Compound 2.
Figure 6:
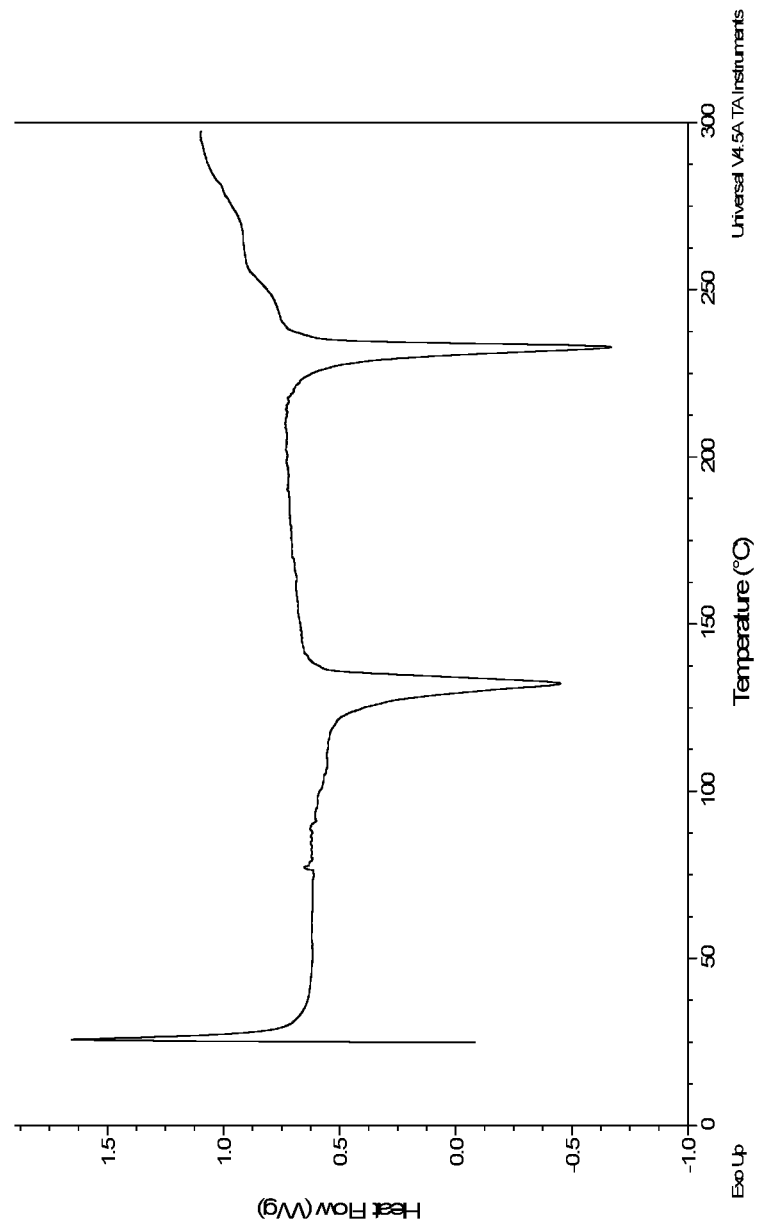
FIG. 6 illustrates a representative DSC thermogram for Form 3 of Compound 2.

In some embodiments, Compound 2 is crystalline. In some embodiments, Compound 2 is crystalline Form 3. In some embodiments, Compound 2 is crystalline Form 3 and has at least one of the following properties:
(a) an X-ray powder diffraction (XRPD) pattern with characteristic peaks at 2.9° 2-Theta, 3.2° 2-Theta, 3.3° 2-Theta, 15.8° 2-Theta, 16.9° 2-Theta, 20.2° 2-Theta;
(b) an X-ray powder diffraction (XRPD) pattern substantially the same as shown in FIG. 5;
(c) a DSC thermogram with two endotherms at about 132.2° C. and 238.8° C.;
(d) a DSC thermogram substantially the same as shown in FIG. 6;
(e) solvated with dimethylsulfoxide (DMSO);
(f) transformation to Compound 2, Form 1 when heated above 130° C.;
(g) transformation to Compound 2, Form 1 after GVS analysis and 7 days at 40° C./75% RH;
(h) transformation to Compound 2, Form 1 after 7 days at 40° C. and 75% RH.

In some embodiments, Compound 2 is crystalline Form 3 and has at least two properties selected from the group consisting of (a), (b), (c), (d), (e), (f), (g), and (h). In some embodiments, Compound 2 is crystalline Form 3 and has at three properties selected from the group consisting of (a), (b), (c), (d), (e), (f), (g), and (h). In some embodiments, Compound 2 is crystalline Form 3 and has at least four properties selected from the group consisting of (a), (b), (c), (d), (e), (f), (g), and (h). In some embodiments, Compound 2 is crystalline Form 3 and has at five properties selected from the group consisting of (a), (b), (c), (d), (e), (f), (g), and (h). In some embodiments, Compound 2 is crystalline Form 3 and has at least six properties selected from the group consisting of (a), (b), (c), (d), (e), (f), (g), and (h). In some embodiments, Compound 2 is crystalline Form 3 and has at least seven properties selected from the group consisting of (a), (b), (c), (d), (e), (f), (g), and (h). In some embodiments, Compound 2 is crystalline Form 3 and has properties (a), (b), (c), (d), (e), (f), (g), and (h).

Form 3 is a DMSO solvate. A XRPD changed to Form 1 when heating Form 3 to 130° C. and upon the storage conditions, which could indicate that Form 3 is a metastable solvate that transforms to Form 1.

In some embodiments, Compound 2 is crystalline and has an X-ray powder diffraction (XRPD) pattern with characteristic peaks at 2.9° 2-Theta, 3.2° 2-Theta, 3.3° 2-Theta, 15.8° 2-Theta, 16.9° 2-Theta, 20.2° 2-Theta.

In some embodiments, Compound 2 is crystalline and has an X-ray powder diffraction (XRPD) pattern substantially the same as shown in FIG. 5.

In some embodiments, Compound 2 is crystalline and has a DSC thermogram with two endotherms at about 132.2° C. and 238.8° C.

In some embodiments, Compound 2 is crystalline and has a DSC thermogram substantially the same as shown in FIG. 6.

In some embodiments, Compound 2 is crystalline and is solvated with dimethylsulfoxide (DMSO).

In some embodiments, Compound 2 is crystalline Form 3 and is obtained from a solution of dimethyl sulfoxide (DMSO) and acetonitrile (MeCN).

Form 4 of Compound 2

Figure 7:
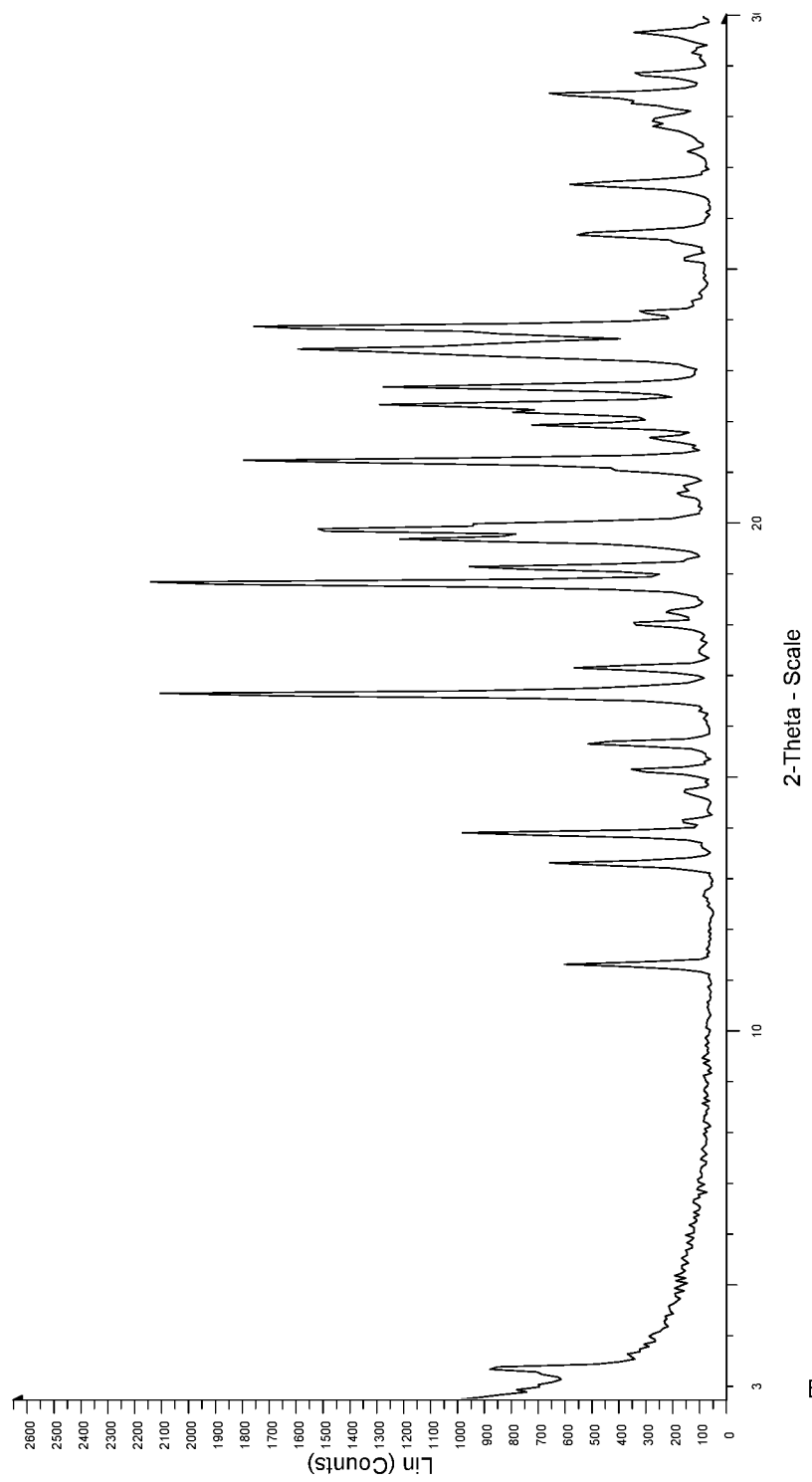
FIG. 7 illustrates the X-ray powder diffraction pattern for Form 4 of Compound 2.

In some embodiments, Compound 2 is crystalline. In some embodiments, Compound 2 is crystalline Form 4. In some embodiments, Compound 2 is crystalline Form 4 and has at least one of the following properties:
(a) an X-ray powder diffraction (XRPD) pattern with characteristic peaks at 13.9° 2-Theta, 16.6° 2-Theta, 18.8° 2-Theta, 19.1° 2-Theta, 19.7° 2-Theta, 19.9° 2-Theta, 20° 2-Theta, 21.2° 2-Theta, 22.3° 2-Theta, 22.7° 2-Theta, 23.4° 2-Theta, 23.8° 2-Theta;
(b) an X-ray powder diffraction (XRPD) pattern substantially the same as shown in FIG. 7;
(c) a DSC thermogram with an endotherm at about 233° C.; or
(d) a DSC thermogram substantially the same as shown in FIG. 9.

In some embodiments, Compound 2 is crystalline Form 4 and has at least properties selected from the group consisting of (a), (b), (c), and (d). In some embodiments, Compound 2 is crystalline Form 4 and has at three properties selected from the group consisting of (a), (b), (c), and (d). In some embodiments, Compound 2 is crystalline Form 4 and has properties (a), (b), (c), and (d).

In some embodiments, Compound 2 is crystalline and has an X-ray powder diffraction (XRPD) pattern with characteristic peaks at 13.9° 2-Theta, 16.6° 2-Theta, 18.8° 2-Theta, 19.1° 2-Theta, 19.7° 2-Theta, 19.9° 2-Theta, 20° 2-Theta, 21.2° 2-Theta, 22.3° 2-Theta, 22.7° 2-Theta, 23.4° 2-Theta, 23.8° 2-Theta.

In some embodiments, Compound 2 is crystalline and has an X-ray powder diffraction (XRPD) pattern substantially the same as shown in FIG. 7.

In some embodiments, Compound 2 is crystalline and has a DSC thermogram with an endotherm at about 233° C.

Figure 8:
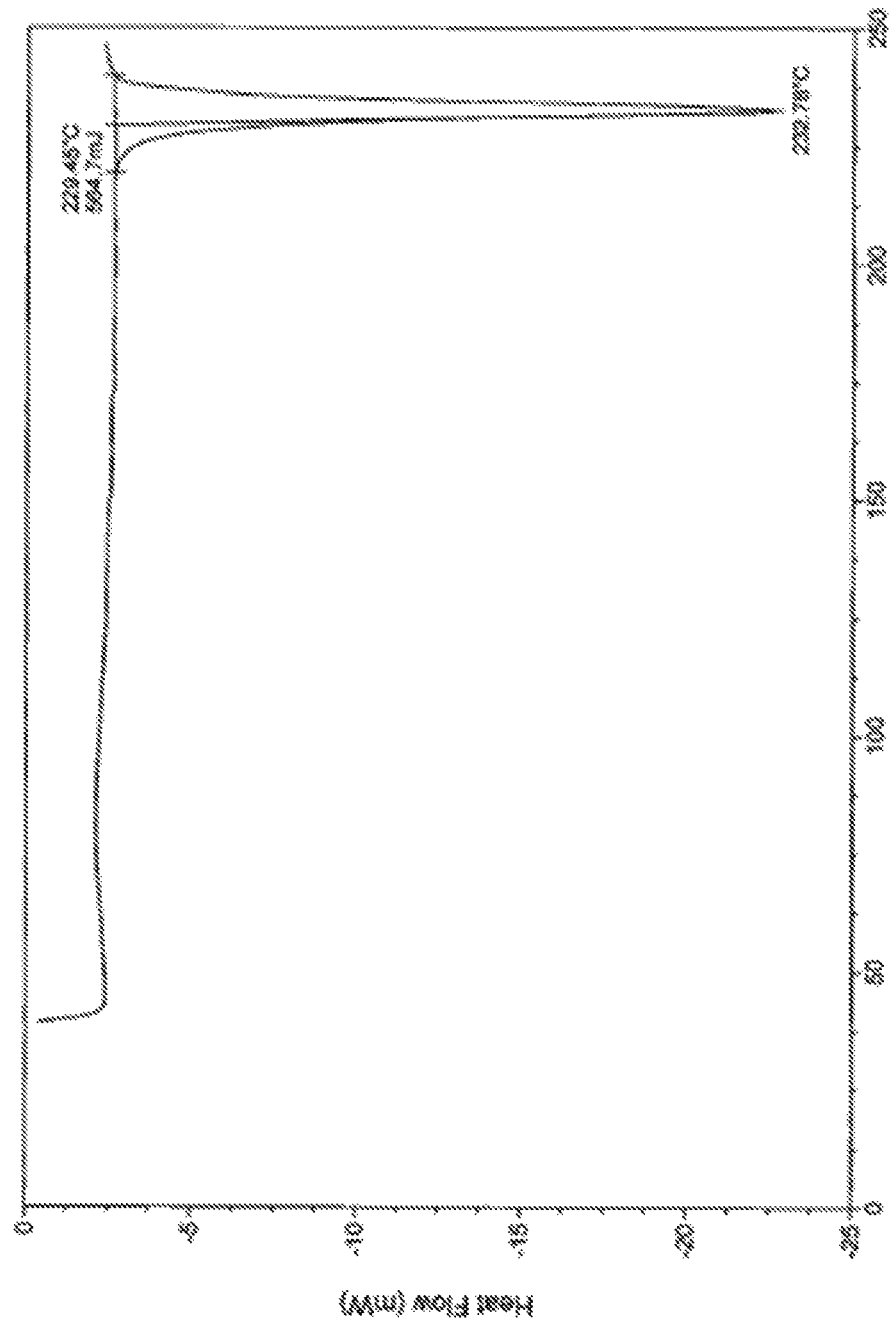
FIG. 8 illustrates a representative DSC thermogram for Form 4 of Compound 2.

In some embodiments, Compound 2 is crystalline and has a DSC thermogram substantially the same as shown in FIG. 8.

In some embodiments, Compound 2 is crystalline Form 4 and is isolated from a slurry of Compound 2 in acetonitrile.

Synthesis of Compound 2

In some embodiments, Compound 2 is prepared via the synthetic route as shown in the following scheme below:

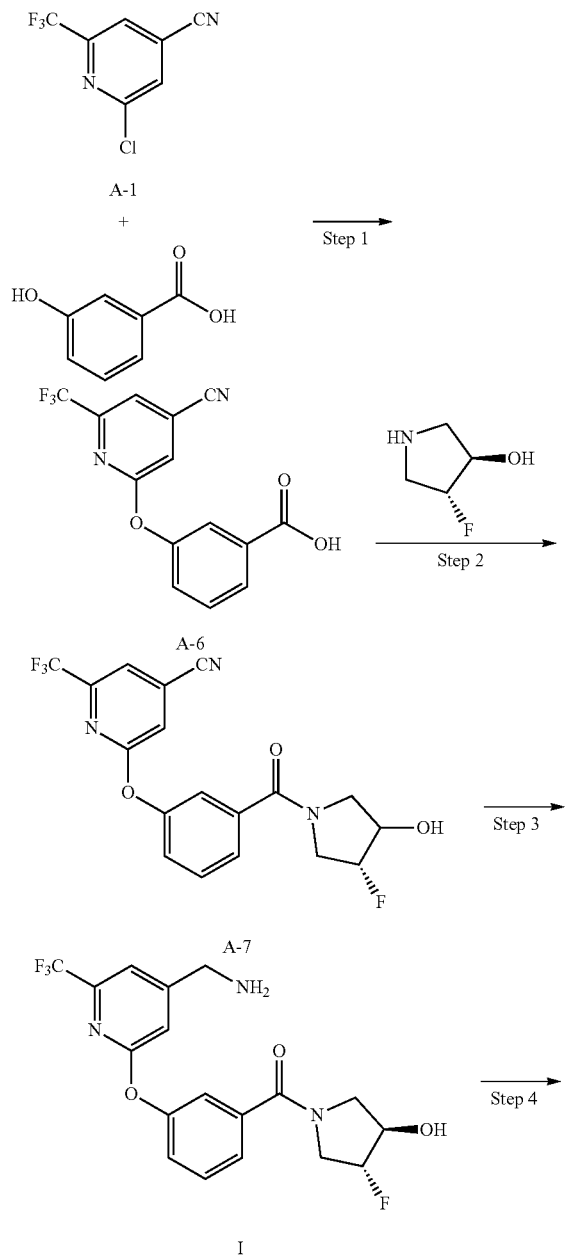

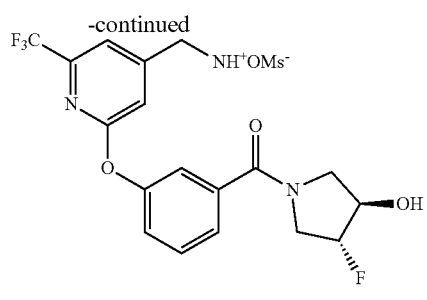

As shown in the scheme above, 2-chloro-6-(trifluoromethyl)isonicotinonitrile (Compound A-1) and 3-hydroxybenzoic acid are reacted under suitable reaction conditions to provide 3-((4-cyano-6-(trifluoromethyl)pyridin-2-yl)oxy)benzoic acid (Compound A-6). In some embodiments, suitable reaction conditions include nucleophilic aromatic substitution (SNAr) reaction conditions. A nucleophilic aromatic substitution is a substitution reaction in which the nucleophile displaces a good leaving group, such as a halide, on an aromatic ring. In some embodiments, suitable reaction conditions include the use of $Cs_2CO_3$ in DMF.

Methods of forming aromatic ethers include those described herein or described in the art including but not limited to the Ulman Ether synthesis, Chan-Lam coupling, and Buchwald-Hartwig synthesis (D. Ma, Q. Cai, *Org. Lett.*, 2003, 5, 3799-3802; C. G. Bates, et al., *Org. Lett.*, 2002, 4, 2803-2806; C. H. Burgos, et al., *Angew. Chem. Int. Ed.*, 2006, 45, 4321-4326; C. H. Burgos, et al., *Angew. Chem. Int. Ed.*, 2006, 45, 4321-4326; D. M. T. Chan, et al., *Tetrahedron Lett.*, 1998, 39, 2933-2936; Z. Liu, R. C. Larock, *J. Org. Chem.*, 2006, 71, 3198-3209; Y.-J. Chen, H.-H. Chen, *Org. Lett.*, 2006, 8, 5609-5612; F. Li, Q. et al., *Org. Lett.*, 2003, 5, 2169-2171; D. A. Evans, et al., *Tetrahedron Letters*, 1998, 39, 2937-2940; C.-E. Yeom, et al., *Synlett*, 2007, 146-150).

In some embodiments, 3-((4-cyano-6-(trifluoromethyl)pyridin-2-yl)oxy)benzoic acid (Compound A-6) is treated with (3R,4R)-4-fluoropyrrolidin-3-ol hydrochloride under suitable coupling conditions to provide 2-(3-((3R,4R)-3-fluoro-4-hydroxypyrrolidine-1-carbonyl)phenoxy)-6-(trifluoromethyl)isonicotinonitrile (Compound A-7).

In some embodiments, appropriate coupling conditions include the use of EDC, DCC, BOP, HATU or the like. In some embodiments, the appropriate coupling conditions include the use of a base. In some embodiments, the base is an organic base. In some embodiments, the base is a hindered base such as trimethylamine, triethylamine (TEA), diisopropylethylamine (DIEA), N-methylmorpholine, pyridine or the like. In some embodiments, the appropriate coupling conditions include the use of a solvent. Suitable solvents include dichloromethane, dichloroethane, tetrahydrofuran, dimethoxyethane or the like.

In some embodiments, appropriate coupling conditions include the use of dicyclohexylcarbodiimide (DCC), diisopropylcarbodiimide (DIC), N-(3-dimethylaminopropyl)-N'-ethylcarbodiimide.HCl (EDC HCl), benzotriazol-1-yloxy-tris(dimethylamino)-phosphonium hexafluorophosphate (BOP), benzotriazol-1-yloxy-tripyrrolidino-phosphonium hexafluorophosphate (PyBOP), bromo-tripyrrolidino-phosphonium hexafluorophosphate (PyBrOP), 7-aza-benzotriazol-1-yloxy-tripyrrolidinophosphonium hexafluorophosphate (PyAOP), ethyl cyano(hydroxyimino)acetato-$O_2$)-tri-(1-pyrrolidinyl)-phosphonium hexafluorophosphate (PyOxim), 3-(diethoxy-phosphoryloxy)-1,2,3-benzo[d]triazin-4(3H)-one (DEPBT), 2-(1H-benzotriazol-1-yl)-N,N,N',N'-tetramethylaminium tetrafluoroborate/hexafluorophosphate (TBTU (BF$_4^-$)), 2-(6-chloro-1H-benzotriazol-1-yl)-N,N,N',N'-tetramethylaminium hexafluorophosphate (HCTU), N-[(5-chloro-1H-benzotriazol-1-yl)-dimethylamino-morpholino]-uronium hexafluorophosphate N-oxide (HDMC), 2-(7-aza-1H-benzotriazol-1-yl)-N,N,N',N'-tetramethylaminium hexafluorophosphate (HATU), 1-[1-(cyano-2-ethoxy-2-oxoethylideneaminooxy)-dimethylamino-morpholino]-uronium hexafluorophosphate (COMU), 2-(1-oxy-pyridin-2-yl)-1,1,3,3-tetramethylisothiouronium tetrafluoroborate (TOTT), tetramethylfluoroformamidinium hexafluorophosphate (TFFH), N-ethoxycarbonyl-2-ethoxy-1,2-dihydroquinoline (EEDQ), 2-propanephosphonic acid anhydride (T3P), 4-(4,6-dimethoxy-1,3,5-triazin-2-yl)-4-methylmorpholinium salts (DMTMM), bis-trichloromethylcarbonate (BTC), or 1,1'-carbonyldiimidazole (CDI).

In some embodiments, the coupling reactions include one or more additives selected from the group consisting of 1-Hydroxybenzotriazole (HOBt), 1-Hydroxybenzotriazole-6-sulfonamidomethyl resin.HCl (HOBt-6-sulfonamidomethyl resin.HCl), Hydroxy-3,4-dihydro-4-oxo-1,2,3-benzotriazine (HOOBt), N-Hydroxysuccinimide (HOSu), 1-Hydroxy-7-aza-1H-benzotriazole (HOAt), Ethyl 2-cyano-2-(hydroximino)acetate, and 4-(N,N-Dimethylamino)pyridine (DMAP).

In some embodiments, suitable reaction conditions include a two-step process, involving first the conversion of the acid into an acyl halide followed by the coupling with (3R,4R)-4-fluoropyrrolidin-3-ol hydrochloride. In some embodiments, suitable reagents for the conversion of the acid into an acyl halide include the use of thionyl chloride (SOCl$_2$), oxalyl chloride ((COCl)$_2$), phosphorus trichloride (PCl$_3$), phosphorus oxychloride (POCl$_3$), and phosphorus pentachloride (PCl$_5$). These reactions are often promoted by the addition of a catalytic amount of dimethylformamide (DMF).

Additional suitable reagents for the conversion of the acid into an acyl halide include the use of cyanuric chloride (2,4,6-trichloro-1,3,5-triazine) in the presence of trimethylamine, triphenylphosphine (TPP) and a source of chloride (e.g. carbon tetrachloride, trichloroacetonitrile), and tetramethyl-α-chloroenamine.

Coupling reactions with acyl chlorides normally requires the use of an additional base to trap the formed HCl. Couplings are usually performed in inert dry solvents, in the presence of a non-nucleophilic tertiary amine (NEt$_3$, iPr$_2$NEt [also called Hunig's base], or N-methylmorpholine). In some embodiments, the coupling reaction is accelerated with a catalytic amount of pyridine or N,N-dimethylaminopyridine (DMAP). In some cases, pyridine is used as the solvent. In some embodiments, the use of metallic zinc can also accelerate the coupling at room temperature.

In some embodiments, suitable reaction conditions include pretreatment of the benzoic acid C with oxalyl chloride prior to addition of the (3R,4R)-4-fluoropyrrolidin-3-ol hydrochloride.

In some embodiments, 2-(3-((3R,4R)-3-fluoro-4-hydroxypyrrolidine-1-carbonyl)phenoxy)-6-(trifluoromethyl) isonicotinonitrile (Compound A-7) is subjected under appropriate reducing conditions to provide 3-((4-(aminomethyl)-6-(trifluoromethyl)pyridin-2-yl)oxy)phenyl)((3R,4R)-3-fluoro-4-hydroxypyrrolidin-1-yl)methanone (Compound I). Suitable nitrile reduction conditions for the reduction of a nitrile to an amine are known (Nishimura, Shigeo (2001). Handbook of Heterogeneous Catalytic Hydrogenation for Organic Synthesis (1st ed.). Wiley-Interscience. pp. 254-277; March, Jerry (1985), Advanced Organic Chemistry: Reactions, Mechanisms, and Structure (3rd ed.), Wiley).

In some embodiments, suitable nitrile reduction conditions include catalytic hydrogenation of nitriles (Karsten et al., (2000). "Amines, Aliphatic". Ullmann's Encyclopedia of Industrial Chemistry). As catalysts for hydrogenating the nitrile function to the corresponding amine, it is possible to use catalysts which comprise one or more elements of the transition group of the Periodic Table, such as, but not limited to, iron, cobalt, nickel, ruthenium, rhodium, palladium, platinum, iridium, or osmium. The catalysts can be doped with promoters that include, for example, chromium, iron, cobalt, manganese, molybdenum, titanium, tin, metals of the alkali metal group, metals of the alkaline earth metal group and/or phosphorus.

Skeletal catalysts (also referred to as Raney type i.e. Raney catalyst) which are obtained by leaching (activating) an alloy of hydrogenation-active metal and a further component (e.g aluminum) are also contemplated. Such catalysts include Raney nickel catalysts and Raney cobalt catalysts.

In some embodiments, supported palladium or platinum catalysts are used as catalysts. In some embodiments, support materials include, but are not limited to, activated carbon, Al$_2$O$_3$, TiO$_2$, ZrO$_2$, and SiO$_2$.

In some embodiments, the catalytic hydrogenation catalyst includes the uses of Raney nickel, palladium black, or platinum dioxide. Other catalysts, such as cobalt boride are contemplated.

Other important factors for the hydrogenation include solvent choice, solution pH, steric effects, temperature, and the pressure of hydrogen inside the hydrogenation vessel.

In some embodiments, appropriate hydrogenation conditions include AcOH 5%, Pd(OH)$_2$/C, and H$_2$.

In some embodiments, non-catalytic reducing agents for the non-catalytic conversion of nitriles to amines include lithium aluminium hydride, lithium borohydride, diborane, or elemental sodium in alcohol solvents.

In some embodiments, 3-((4-(aminomethyl)-6-(trifluoromethyl)pyridin-2-yl)oxy)phenyl)((3R,4R)-3-fluoro-4-hydroxypyrrolidin-1-yl)methanone (Compound I) is treated under appropriate reaction conditions to provide (3-((4-(aminomethyl)-6-(trifluoromethyl)pyridin-2-yl)oxy)phenyl) ((3R,4R)-3-fluoro-4-hydroxypyrrolidin-1-yl)methanone, methanesulfonate salt (Compound 2). In some embodiments, appropriate reaction conditions include diluting Compound I in ACN, slowly adding methanesulfonic acid (MSA), and adjusting MSA concentration by HPLC purity. In some embodiments, reaction solution was aged for about 1 hour at about 20±5° C. and heated to reflux (~82°-85° C.) for about 2 hours. In some embodiments, the mixture was allowed to stir over night at room temperature and the heating cycle was repeated 3 more times until the DSC conformed.

In some embodiments, Compound 2 is prepared via the synthetic route as shown in the following scheme below:

Scheme 4. Alternative Preparation of Compound 2.

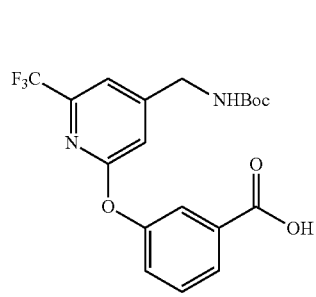
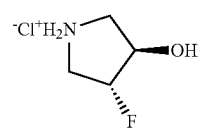
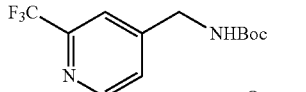
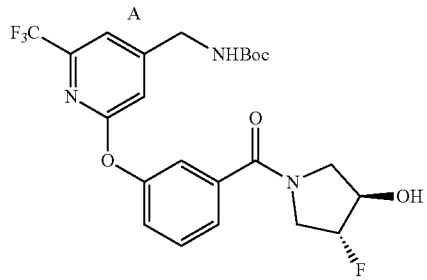
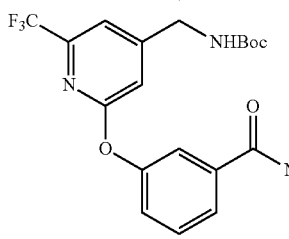
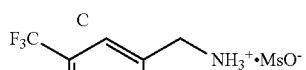

Compound 2

As shown in the scheme above, in some embodiments, (3-(4-((tert-butoxycarbonyl)methyl)-6-(trifluoromethyl)pyridin-2-yloxy)benzoic acid) (Compound A) and ((3R,4R)-4-fluoropyrrolidin-3-ol hydrochloride ((R,R)-FP) are reacted under appropriate coupling conditions to provide tert-butyl ((2-(3-((3R,4R)-3-fluoro-4-hydroxypyrrolidine-1-carbonyl)phenoxy)-6-(trifluoromethyl)pyridin-4-yl)methyl) carbamate (Compound C). Appropriate coupling conditions are discussed above. In some embodiments, appropriate coupling conditions include HATU, DIPEA, and DCM/DMF.

In some embodiments, Compound C is treated with methanesulfonic acid under appropriate reaction conditions to provide (3-((4-(aminomethyl)-6-(trifluoromethyl)pyridin-2-yl)oxy)phenyl)((3R,4R)-3-fluoro-4-hydroxypyrrolidin-1-yl)methanone, methanesulfonate salt (Compound 2). In some embodiments, appropriate reaction conditions include dissolving Compound C in DCM, transferring the solution to the reactor, and diluting with DCM. In some embodiments, methanesulfonic acid was charged, and the reaction heated to reflux and stirred over night until being deemed complete. In some embodiments, the resultant thick white slurry was diluted with DCM, cooled and filtered, and rinsed with methyl-tert-butyl-ether (MTBE).

In some embodiments, samples of Compound 2 are greater than 90% pure. In some embodiments, samples of Compound 2 are greater than 95% pure, greater than 96% pure, greater than 97% pure, greater than 98% pure, or greater than 99% pure.

In some embodiments, samples of Compound 2 include a detectable amount of at least one of the following compounds:

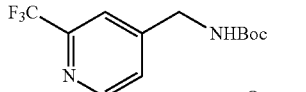
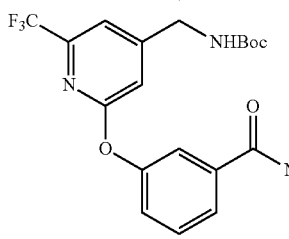
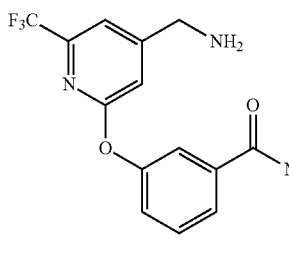
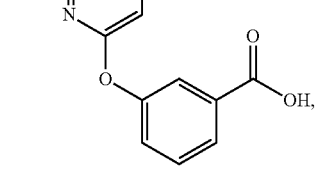
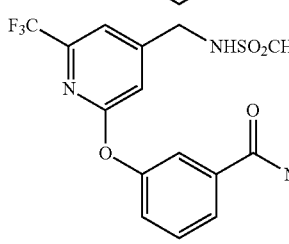
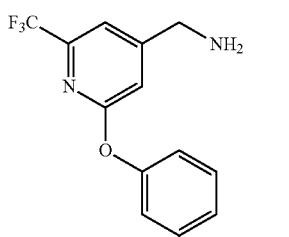
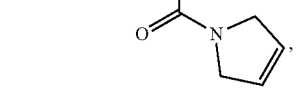

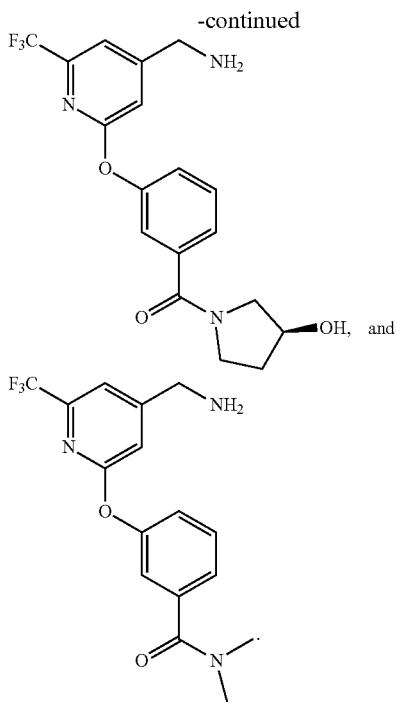

In some embodiments, samples of Compound 2 have a chiral purity of greater than 90%. In some embodiments, samples of Compound 2 have a chiral purity of greater than 95%, greater than 96%, greater than 97%, greater than 98%, or greater than 99%.

In some embodiments, samples of Compound 2 include a detectable amount of the (S,S)-enantiomer of Compound 2.

In some embodiments, samples of Compound 2 contain less than 5% of (3R,4R)-4-fluoropyrrolidin-3-ol. In some embodiments, samples of Compound 2 contain less 5%, 4%, 3%, 2%, or 1% of (3R,4R)-4-fluoropyrrolidin-3-ol.

Preparation of Crystalline Forms

In some embodiments, a crystalline form of a pharmaceutically acceptable salt of "(R,R)-trans-(3-((4-(aminomethyl)-6-(trifluoromethyl)pyridin-2-yl)oxy)phenyl)(3-fluoro-4-hydroxypyrrolidin-1-yl)methanone (e.g. (R,R)-trans-(3-(4-(aminomethyl)-6-(trifluoromethyl)pyridin-2-yl)oxy)phenyl)(3-fluoro-4-hydroxypyrrolidin-1-yl)methanone, hydrochloride salt or (R,R)-trans-(3-((4-(aminomethyl)-6-(trifluoromethyl)pyridin-2-yl)oxy)phenyl)(3-fluoro-4-hydroxypyrrolidin-1-yl)methanone, methanesulfonate salt) is prepared as outlined in the Examples. It is noted that solvents, temperatures and other reaction conditions presented herein may vary.

Suitable Solvents

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. Preferred solvents are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene.

Class 3 solvents, which possess low toxicity, include: acetic acid, acetone, anisole, 1-butanol, 2-butanol, butyl acetate, tert-butylmethyl ether (MTBE), cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran.

Residual solvents in active pharmaceutical ingredients (APIs) originate from the manufacture of API. In some cases, the solvents are not completely removed by practical manufacturing techniques. Appropriate selection of the solvent for the synthesis of APIs may enhance the yield, or determine characteristics such as crystal form, purity, and solubility. Therefore, the solvent is a critical parameter in the synthetic process.

In some embodiments, compositions comprising salts of Compound I comprise an organic solvent(s). In some embodiments, compositions comprising salts of Compound I comprise a residual amount of an organic solvent(s). In some embodiments, compositions comprising salts of Compound I comprise a residual amount of a Class 2 solvent. In some embodiments, the Class 2 solvent is selected from acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene. In some embodiments, the Class 2 solvent is dichloromethane, acetonitrile, and N,N-dimethylformamide. In some embodiments, compositions comprising salts of Compound I comprise a residual amount of a Class 3 solvent. In some embodiments, the organic solvent is a Class 3 solvent. In some embodiments, the Class 3 solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran. In some embodiments, the Class 3 solvent is selected from ethyl acetate, tert-butylmethylether, heptane, and acetone.

In some embodiments, the compositions comprising a salt of Compound I include a detectable amount of an organic solvent. In some embodiments, the salt of Compound I is a hydrochloride salt (i.e. Compound 1). In some embodiments, the salt of Compound I is a mesylate salt (i.e. Compound 2). In some embodiments, the organic solvent is a Class 2 solvent. In some embodiments, the organic solvent is a Class 3 solvent.

(3R,4R)-4-Fluoropyrrolidin-3-ol

In some embodiments, (3R,4R)-4-fluoropyrrolidin-3-ol-hydrochloride is prepared as described in Scheme 5.

Scheme 5. Preparation of (3R,4R)-4-fluoropyrrolidin-3-ol, hydrochloride (Compound C6)

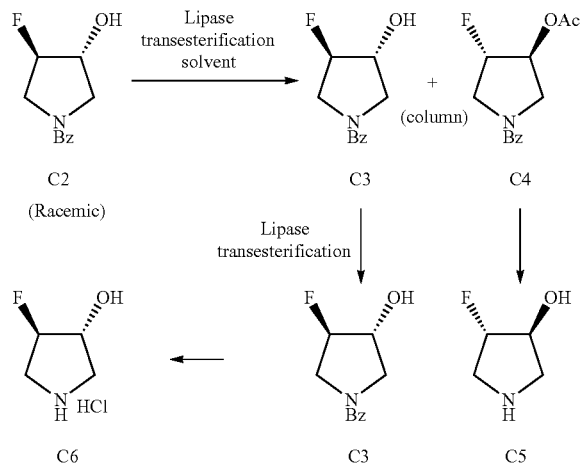

In some embodiments, (3R,4R)-4-fluoropyrrolidin-3-ol is prepared from racemic (trans-3-fluoro-4-hydroxypyrrolidin-1-yl)(phenyl)methanone with the use of enzyme biocatalysis. In some embodiments, the enzyme biocatalysis includes the use of a suitable lipase. Lipases are one of the most commonly used classes of enzymes in biocatalysis. They have been used on a variety of substrates and show very broad substrate specificity. Lipases catalyze the hydrolysis of triacylglycerols to diacylglycerol, monoacylglycerol, glycerol and free fatty acids. The reaction reverses under anhydrous conditions and the enzyme is able to synthesize new molecules by esterification, alcoholysis and transesterification. All reactions can be performed with high regio- and enantioselectivity under mild reaction conditions.

The synthetic applications of lipases exploit their chemo-, regio- and stereoselectivity. Lipases catalyze regio- and chemoselective reactions of polyfunctional compounds which include protective and deprotective techniques.

The stereoselectivity of lipase-catalyzed transesterifications is used for the preparation of enantiopure alcohols by the kinetic resolution of the corresponding racemates. Other functionalities are accepted in the alcohol structure, although lipase catalysis is maintained for the hydroxyl functionality. The enantioselectivity obtained with secondary alcohols is often high compared to what is observed with primary or tertiary alcohols. Lipase catalysis for secondary alcohols is orientated to the hydroxyl function directly attached to the asymmetric center.

The kinetic resolution of secondary alcohols and esters is performed in organic solvents by lipase-catalyzed acylation and alcoholysis, respectively. It leads to the formation of one enantiomer as an alcohol and the other enantiomer as an ester. The maximum theoretical yield for each enantiomer is 50%.

Lipase-catalysed resolution of alcohols is performed in the presence of an acyl donor. In some embodiments, the lipase-catalysed resolution of alcohols is performed in the presence of quasi-irreversible or irreversible acyl donors. In some embodiments, the lipase-catalysed resolution of alcohols is performed in the presence of enol esters as irreversible transesterification reagents.

Quasi-irreversible and irreversible acyl donors belong to activated acyl donors and they contribute to the increase of the rates of enzymatic reactions. Quasi-irreversible acyl donors include, but are not limited to, 2,2,2-trifluoroethyl esters, cyanomethyl esters, and oxime esters. Irreversible acyl donors include, but are not limited to, anhydrides and enol esters. Enol esters include, but are not limited to, vinyl esters, isoprenyl esters, and ethoxy vinyl esters. Vinyl esters include, but are not limited to, acetate vinyl ester, pivalate vinyl ester, 4-pentenoate vinyl ester, crotonate vinyl ester, methacrylate vinyl ester, benzoate vinyl ester, cinnamate vinyl ester, N-Boc glycinate vinyl ester, and phenyl(thio)acetate vinyl ester.

When reversible acyl donors (alkyl esters and thioesters) are used for the acylation, thermodynamic equilibrium can be shifted towards the product formation by using an excess of an acyl donor or by removal of a product formed in the reaction mixture.

In some embodiments, the enzymatic reaction is performed in an organic solvent. In some embodiments, the organic solvent is dimethylsulfoxide, N,N-dimethylformamide, methanol, ethanol, acetone, methyl acetate, ethyl acetate, butanol, diethylether, TBME, DIPE, toluene, cyclohexane, hexane, or heptane. In some embodiments, the organic solvent is acetone, tetrahydrofuran, diethyl ether, tert-amyl alcohol, DIPE, or toluene. In some embodiments, the organic solvent is acetone.

Lipases used in synthetic reactions are generally derived from microorganisms. Fungal lipases include *Candida rugose* (CRL), *Candida antarctica* A (CAL-A), *Candida antarctica* B (CAL-B), *Thermomyces lanuginosus* (TL IL), *Rhizomucor miehei* (RL IM). Bacterial lipases include *Pseudomonas fluorescens* (AK, PFL), *Burkholderia cepacia* (PS), *Chromobacterium viscosum* (CVL).

Lipases include *Candida antarctica* lipase B, *Burkholderia cepacia* lipases, and *Thermomyces lanuginosus* lipases. The yeast *Candida antarctica* produces two different lipases, A (CAL-A) and B (CAL-B). Both lipases have been purified, characterized and are available in immobilized forms. CAL-B is a protein with a molecular mass of 33 kDa and pI of 6.0. The enzyme is stable in aqueous media over the pH range 3.5-9.5. The denaturation temperature is between 50-60° C. The most often used CAL-B preparation is Novozyme 435 which contains the enzyme immobilized on macroporous acrylic polymer resin based on an undisclosed protocol. Additional enzymatic preparations containing CAL-B include, but are not limited to, IMMCALB-T1-1500, IMMCALB-T2-150, IMMCALB-T2-350, IMMCALB-T3-150, IMMCALBY-T1-1500, IMMCALBY-T2-150, IMMCALBY-T2-350, IMMCALBY-T3-150.

Immobilization methods are either adsorption on dry polypropylene beads or covalent attachment to dry or wet acrylic beads. The size of the beads may vary (150-300 μm, 350-700 μm, <1500 μm).

*Burkholderia cepacia* lipase (previously named *Pseudomonas cepacia*) has a bacterial origin. *Burkholderia cepacia* lipase is a protein consisting of 320 amino acids and with a molecular mass of 33 kDa. This lipase is available in free form (lipase SL and lipase AH), immobilized by adsorption on diatomaceous earth (PS-D), or immobilized by strong adsorption forces on ceramics Toyonite 200 (PS-C II).

*Thermomyces lanuginosus* lipase (previously named *Humicola lanuginosa*) has a fungal origin. This protein has a molecular mass of 30 kDa and 269 amino acids. The optimum pH is 11-12 and thermostability is kept until 55-60° C. *Thermomyces lanuginosus* lipase is the active component of the commercial preparation Lipolase®. Lipase preparations from *Thermomyces Lanuginosus* include Lipozyme TL IM (lipase immobilized on silica), IMMTLL-T1-1500 (lipase immobilized by adsorption on polypropylene) and IMMTLL-T2-150 (lipase immobilized covalently on polyacrylic beads).

In addition, one mammalian lipase (porcine pancreas (PPL)), has proved to be useful.

In some embodiments, lipase enzymes contemplated for use herein include immobilized lipase enzymes. Immobilization of lipase enzymes on a solid carrier leads to a number of benefits for biocatalysis. Benefits of immobilized lipase enzymes include better performance in non-aqueous solvents, efficient recovery and separation of reaction product, can be recycled for cost savings, minimizes protein contamination of product, enhanced stability from heat, organic solvents or autolysis, higher catalyst productivity for cost-efficiency, and convenient and safer handling.

Immobilized enzymes are useful for the enantioselective resolution of esters, acylation of alcohols to form esters, mild hydrolysis or acylation of sensitive substrates, kinetic resolution by transesterification of racemic alcohols, kinetic resolution by hydrolysis of racemic esters.

In organic solvents, lipases are used in dried forms obtained by lyophilization and increasingly by immobilization. Advantages of using immobilized lipases are those derived from heterogeneous catalysis, such as easy recovery, recyclability, and possibility to develop continuous processes. Immobilization is used to increase the stability in organic solvents. Moreover, activity, substrate specificity and enantioselectivity may be improved by immobilization. The methods available for immobilization are adsorption on a carrier and encapsulation or covalent attachment to a carrier. Cross-linking of enzyme is a particular case of immobilization based on the formation of covalent bonds without using a carrier.

In some embodiments, Novozyme® 435 is used as the lipase enzyme for the kinetic resolution by transesterification of racemic alcohol C2. Novozyme® 435 is a CALB lipase immobilized on a hydrophobic carrier (acrylic resin). Additional lipase enzymes contemplated for the resolution of racemic alcohol C2 include Novocor® AD L (from *Candida Antarctica* A (CALA)) and Lipozyme® CALB L (from *Candida Antarctica* B (CALB)).

In some embodiments, racemic alcohol C2 is treated with vinyl acetate and Novozyme® 435 in acetone to provide unreacted alcohol C3 and ester C4. Alcohol C3 and ester C4 are the separated. In some embodiments, alcohol C3 and ester C4 are separated by column chromatography.

In some embodiments, the chiral purity of alcohol C3 is enhanced by subjecting alcohol C3 to a second round of vinyl acetate and Novozyme® 435 in acetone. After the reaction is deemed to be complete, alcohol C3 is purified. In some embodiments, alcohol C3 is purified by column chromatography.

The amide of compound C3 is then hydrolyzed to provide (3R,4R)-4-fluoropyrrolidin-3-ol. In some embodiments, compound C3 is treated with an acid in a suitable solvent to provide (3R,4R)-4-fluoropyrrolidin-3-ol. In some embodiments, the acid is hydrochloric acid. In some embodiments, the suitable solvent is an organic solvent. In some embodiments, the organic solvent is an ether solvent. In some embodiments, the organic solvent is 1,4-dioxane, tetrahydrofuran, tetrahydropyran, dimethoxyethane or diethyl ether. In some embodiments, the organic solvent is 1,4-dioxane.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein, or a pharmaceutically acceptable salt thereof, and a co-agent, are both administered to a patient simultaneously in the form of a single entity or dosage. The term "non-fixed combination" means that the active ingredients, e.g. a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions/Formulations

Pharmaceutical compositions are formulated in a conventional manner using one or more physiologically acceptable carriers comprising excipients and auxiliaries which facilitate processing of the active compounds into preparations which are used pharmaceutically. Suitable techniques, carriers, and excipients include those found within, for example, *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems, Seventh Ed.* (Lippincott Williams & Wilkins 1999), herein incorporated by reference in their entirety.

In some embodiments, for oral administration, Compound I, or a pharmaceutically acceptably salt thereof (e.g. Compound 1 or Compound 2), are formulated by combining the active compound with pharmaceutically acceptable carriers or excipients. Such carriers enable Compound I, or a pharmaceutically acceptably salt thereof (e.g. Compound 1 or Compound 2) to be formulated as tablets, powders, pills, dragees, capsules, liquids, gels, syrups, elixirs, slurries, suspensions and the like, for oral ingestion by a patient to be treated. In some embodiments, for oral administration, Compound I, or a pharmaceutically acceptably salt thereof (e.g. Compound 1 or Compound 2), is formulated without combining the active compound with pharmaceutically acceptable carriers or excipients and is placed directly into a capsule for administration to a mammal.

The pharmaceutical compositions described herein include Compound I, or a pharmaceutically acceptable salt thereof (e.g. Compound 1 or Compound 2). In some embodiments, the pharmaceutical compositions described herein include Compound 1. In some embodiments, the pharmaceutical compositions described herein include amorphous Compound 1. In some embodiments, the pharmaceutical compositions described herein include crystalline Compound 1. In some embodiments, the pharmaceutical compositions described herein include Compound 2. In some embodiments, the pharmaceutical compositions described herein include amorphous Compound 2. In some embodiments, the pharmaceutical compositions described herein include crystalline Compound 2.

In some embodiments, the pharmaceutical compositions described herein include: (a) Compound I, or a pharmaceutically acceptable salt thereof (e.g. Compound 1 or Compound 2); and one or more of the following: (b) binders; (c) disintegrants; (d) fillers (diluents); (e) lubricants; (f) glidants (flow enhancers); (g) compression aids; (h) colors; (i) sweeteners; (j) preservatives; (k) suspending/dispersing agents; (1) film formers/coatings; (m) flavors; (o) printing inks; (p) solubilizers; (q) alkalizing agents; (r) buffering agents; (s) antioxidants; (t) effervsescent agents.

In some embodiments, the pharmaceutical compositions described herein include: (a) Compound I, or a pharmaceutically acceptable salt thereof (e.g. Compound 1 or Compound 2); and (b) a capsule shell.

In some embodiments, pharmaceutical compositions described herein include one or more of the following in addition to Compound I, or a pharmaceutically acceptable salt thereof (e.g. Compound 1 or Compound 2): (a) magnesium stearate; (b) lactose; (c) microcrystalline cellulose; (d) silicified microcrystalline cellulose; (e) mannitol; (f) starch (corn); (g) silicon dioxide; (h) titanium dioxide; (i) stearic acid; (j) sodium starch glycolate; (k) gelatin; (l) talc; (m) sucrose; (n) aspartame; (o) calcium stearate; (p) povidone; (q) pregelatinized starch; (r) hydroxy propyl methylcellulose; (s) OPA products (coatings & inks); (t) croscarmellose; (u) hydroxy propyl cellulose; (v) ethylcellulose; (w) calcium phosphate (dibasic); (x) crospovidone; (y) shellac (and glaze); (z) sodium carbonate; (aa) hypromellose.

In one embodiment, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, silicified microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate.

In one embodiment, the pharmaceutical compositions described herein are formulated into any suitable dosage form, including but not limited to, aqueous oral dispersions, solid oral dosage forms, fast melt formulations, effervescent formulations, lyophilized formulations, tablets, capsules, pills, controlled release formulations, enteric coated tablets, inhaled powder, inhaled dispersion, IV formulations.

In further embodiments, the pharmaceutical compositions provided herein may be provided as compressed tablets, tablet triturates, rapidly dissolving tablets, multiple compressed tablets, or enteric-coated tablets, sugar-coated, or film-coated tablets.

Pharmaceutical dosage forms can be formulated in a variety of methods and can provide a variety of drug release profiles, including immediate release, sustained release, and delayed release. In some cases it may be desirable to prevent drug release after drug administration until a certain amount of time has passed (i.e. timed release), to provide substantially continuous release over a predetermined time period (i.e. sustained release) or to provide release immediately following drug administration (i.e., immediate release).

In some embodiments, formulations provide a therapeutically effective amount of Compound I, or a pharmaceutically acceptable salt thereof (e.g. Compound 1 or Compound 2), enabling, for example, once a week, twice a week, three times a week, four times a week, five times a week, once every other day, once-a-day, twice-a-day (b.i.d.), or three times a day (t.i.d.) administration if desired. In one embodiment, the formulation provides a therapeutically effective amount of Compound I, or a pharmaceutically acceptable salt thereof (e.g. Compound 1 or Compound 2) enabling once-a-day administration.

In one embodiment, Compound I, or a pharmaceutically acceptable salt thereof (e.g. Compound 1 or Compound 2) is formulated into an immediate release form that provides for once-a-day administration. Generally speaking, one will desire to administer an amount of Compound I, or a pharmaceutically acceptable salt thereof (e.g. Compound 1 or Compound 2) that is effective to achieve a plasma level commensurate with the concentrations found to be effective in vivo for a period of time effective to elicit a therapeutic effect.

In some embodiments, Compound I, or a pharmaceutically acceptable salt thereof (e.g. Compound 1 or Compound 2) and one or more excipients are dry blended and compressed into a mass, such as a tablet, having a hardness sufficient to provide a pharmaceutical composition that substantially disintegrates within less than about 10 minutes, less than about 15 minutes, less than about 20 minutes, less than about 25 minutes, less than about 30 minutes, less than about 35 minutes, or less than about 40 minutes, after oral administration, thereby releasing the Compound I, or a pharmaceutically acceptable salt thereof (e.g. Compound 1 or Compound 2) formulation into the gastrointestinal fluid.

In some embodiments, the pharmaceutical compositions provided herein in an immediate release dosage form are capable of releasing not less than 75% of the therapeutically active ingredient or combination and/or meet the disintegration or dissolution requirements for immediate release tablets of the particular therapeutic agents or combination included in the tablet core, as set forth in USP XXII, 1990 (The United States Pharmacopeia). Immediate release pharmaceutical compositions include capsules, tablets, pills, oral solutions, powders, beads, pellets, particles, and the like.

Excipients used in pharmaceutical compositions should be selected on the basis of compatibility with Compound I, or a pharmaceutically acceptable salt thereof (e.g. Compound 1 or Compound 2) and the release profile properties of the desired dosage form. Exemplary excipients include, e.g., binders, suspending agents, disintegration agents, filling agents, surfactants, solubilizers, stabilizers, lubricants, wetting agents, diluents, and the like.

Binders impart cohesiveness to solid oral dosage form formulations: for powder filled capsule formulation, they aid in plug formation that is filled into soft or hard shell capsules and for tablet formulation, they ensure the tablet remaining intact after compression and help assure blend uniformity prior to a compression or fill step.

In some embodiments, the binder(s) are selected from starches, sugars, povidone, cellulose or modified cellulose such as microcrystalline cellulose, hydroxypropyl methyl cellulose, lactose, or sugar alcohols like xylitol, sorbitol or maltitol. In some embodiments, the binder is hydroxypropyl methyl cellulose. In some embodiments, the binder is hypromellose (e.g., Methocel E5).

In general, binder levels of 20-70% are used in powder-filled gelatin capsule formulations. Binder usage level in tablet formulations varies whether direct compression, wet granulation, roller compaction, or usage of other excipients such as fillers which itself acts as moderate binder.

Dispersing agents, and/or viscosity modulating agents include materials that control the diffusion and homogeneity of a drug through liquid media or a granulation method or blend method. In some embodiments, these agents also facilitate the effectiveness of a coating or eroding matrix.

Diluents increase bulk of the composition to facilitate compression or create sufficient bulk for homogenous blend for capsule filling.

The term "disintegrate" includes both the dissolution and dispersion of the dosage form when contacted with gastrointestinal fluid. "Disintegration agents or disintegrants" facilitate the breakup or disintegration of a substance. In some embodiments, one aspect, solid oral dosage forms include up to 15% w/w of disintegrant. In some embodiments, the disintegrant is croscarmellose sodium. In another aspect, the disintegrant is sodium starch glycolate or crospovidone.

Filling agents include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

In one aspect, the filler is lactose (e.g. monohydrate). In another aspect, the filler is mannitol, or dicalcium phosphate. In another aspect, the filler is mannitol, microcrystalline cellulose, dicalcium phosphate or sorbitol.

Gastrointestinal fluid is the fluid of stomach secretions of a subject or the saliva of a subject after oral administration of a composition described herein, or the equivalent thereof. An "equivalent of stomach secretion" includes, e.g., an in vitro fluid having similar content and/or pH as stomach secretions such as a 1% sodium dodecyl sulfate solution or 0.1N HCl solution in water. In addition, simulated intestinal fluid (USP) is an aqueous phosphate buffer system at pH 6.8.

Lubricants and glidants are compounds that prevent, reduce or inhibit adhesion or friction of materials. In one aspect, solid oral dosage forms include about 0.25% w/w to about 2.5% w/w of lubricant. In another aspect solid oral dosage forms include about 0.5% w/w to about 1.5% w/w of lubricant.

In some embodiments, the solid dosage forms described herein are in the form of a tablet, (including an immediate release tablet, an extended release tablet, a sustained release tablet, a enteric coated tablet, a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, multiparticulate dosage forms, pellets, or granules.

In other embodiments, the pharmaceutical formulation is in the form of a powder. In still other embodiments, the pharmaceutical formulation is in the form of a tablet, including but not limited to, an immediate release tablet. Additionally, pharmaceutical formulations described herein are administered as a single dosage or in multiple dosages. In some embodiments, the pharmaceutical formulation is administered in two, or three, or four tablets.

In some embodiments, solid dosage forms, e.g., tablets, effervescent tablets, and capsules, are prepared by mixing Compound I, or a pharmaceutically acceptable salt thereof (e.g. Compound 1 or Compound 2) with one or more pharmaceutical excipients to form a bulk blend composition. When referring to these bulk blend compositions as homogeneous, it is meant that the Compound I, or a pharmaceutically acceptable salt thereof (e.g. Compound 1 or Compound 2) particles are dispersed evenly throughout the composition so that the composition is capable of being readily subdivided into equally effective unit dosage forms, such as tablets, pills, or capsules. In one embodiment, the individual unit dosages also include film coatings, which disintegrate upon oral ingestion or upon contact with diluent. In one embodiment, these formulations are manufactured by conventional techniques.

Conventional techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

Compressed tablets are solid dosage forms prepared by compacting the bulk blend formulations described above. In various embodiments, compressed tablets which are designed to dissolve in the mouth will include one or more flavoring agents. In other embodiments, the compressed tablets will include a film surrounding the final compressed tablet. In some embodiments, the film coating aids in patient compliance (e.g., Opadry® coatings or sugar coating). Film coatings comprising Opadry® typically range from about 1% to about 5% of the tablet weight. In other embodiments, the compressed tablets include one or more excipients.

Provided herein are pharmaceutical compositions in film-coated dosage forms, which comprise a combination of an active ingredient, or a pharmaceutically acceptable salt, solvate, or prodrug thereof; and one or more tabletting excipients to form a tablet core using conventional tabletting processes and subsequently coating the core. The tablet cores can be produced using conventional granulation methods, for example wet or dry granulation, with optional comminution of the granules and with subsequent compression and coating.

Further provided herein are pharmaceutical compositions in enteric coated dosage forms, which comprise a combination of an active ingredient, or a pharmaceutically acceptable salt, solvate, or prodrug thereof; and one or more release controlling excipients for use in an enteric coated dosage form. The pharmaceutical compositions also comprise non-release controlling excipients.

Enteric-coatings are coatings that resist the action of stomach acid but dissolve or disintegrate in the intestine.

In one aspect, the oral solid dosage form disclosed herein include an enteric coating(s). Enteric coatings include one or more of the following: cellulose acetate phthalate; methyl acrylate-methacrylic acid copolymers; cellulose acetate succinate; hydroxy propyl methyl cellulose phthalate; hydroxy propyl methyl cellulose acetate succinate (hypromellose acetate succinate); polyvinyl acetate phthalate (PVAP); methyl methacrylate-methacrylic acid copolymers; methacrylic acid copolymers, cellulose acetate (and its succinate and phthalate version); styrol maleic acid co-polymers; polymethacrylic acid/acrylic acid copolymer; hydroxyethyl ethyl cellulose phthalate; hydroxypropyl methyl cellulose acetate succinate; cellulose acetate tetrahydrophtalate; acrylic resin; shellac.

An enteric coating is a coating put on a tablet, pill, capsule, pellet, bead, granule, particle, etc. so that it doesn't dissolve until it reaches the small intestine.

Sugar-coated tablets are compressed tablets surrounded by a sugar coating, which may be beneficial in covering up objectionable tastes or odors and in protecting the tablets from oxidation.

Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating.

Multiple compressed tablets are compressed tablets made by more than one compression cycle, including layered tablets, and press-coated or dry-coated tablets. In some embodiments, tablets are coated with water soluble, pH independent film coating which allows for immediate disintegration for fast, active release (e.g. Opadry products).

In some embodiments, the pharmaceutical compositions provided herein are in the form of a controlled release dosage form. As used herein, the term "controlled release" refers to a dosage form in which the rate or place of release of the active ingredient(s) is different from that of an immediate dosage form when orally administered. Controlled release dosage forms include delayed-, extended-, prolonged-, sustained-, pulsatile-, modified-, targeted-, programmed-release. The pharmaceutical compositions in controlled release dosage forms are prepared using a variety of modified release devices and methods including, but not limited to, matrix controlled release devices, osmotic controlled release devices, multiparticulate controlled release devices, ion-exchange resins, enteric coatings, multilayered coatings, and combinations thereof. The release rate of the active ingredient(s) can also be modified by varying the particle sizes.

In contrast to immediate release compositions, controlled release compositions allow delivery of an agent to a human over an extended period of time according to a predetermined profile. Such release rates can provide therapeutically effective levels of agent for an extended period of time and thereby provide a longer period of pharmacologic response. Such longer periods of response provide for many inherent benefits that are not achieved with the corresponding immediate release preparations. In one aspect, controlled release compositions of Compound I, or a pharmaceutically acceptable salt thereof, provide therapeutically effective levels of Compound I for an extended period of time and thereby provide a longer period of pharmacologic response.

Delayed release as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above.

In some embodiments, the pharmaceutical compositions provided herein is in a modified release dosage form that is fabricated using a matrix controlled release device (see, Takada et al in "Encyclopedia of Controlled Drug Delivery," Vol. 2, Mathiowitz ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

In some embodiments, a matrix controlled release system includes an enteric coating so that no drug is released in the stomach.

The pharmaceutical compositions provided herein may be provided in unit-dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include individually packaged tablets and capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include bottles of tablets or capsules.

In other embodiments a powder comprising the Compound I, or a pharmaceutically acceptable salt thereof (e.g. Compound 1 or Compound 2) formulations described herein are formulated to include one or more pharmaceutical excipients and flavors. Additional embodiments also comprise a suspending agent and/or a wetting agent. This bulk blend is uniformly subdivided into unit dosage packaging or multi-dosage packaging units. The term "uniform" means the homogeneity of the bulk blend is substantially maintained during the packaging process.

In still other embodiments, effervescent powders are prepared. Effervescent salts have been used to disperse medicines in water for oral administration. Effervescent salts are granules or coarse powders containing a medicinal agent in a dry mixture, usually composed of sodium bicarbonate, citric acid and/or tartaric acid.

The method of preparation of the effervescent granules described herein employs three basic processes: wet granulation, dry granulation and fusion. The fusion method is used for the preparation of most commercial effervescent powders. It should be noted that, although these methods are intended for the preparation of granules, the formulations of effervescent salts described herein, in one embodiment, are also prepared as tablets, according to technology for tablet preparation.

In one embodiment, pharmaceutical preparations which are used orally include push-fit capsules made of gelatin, as well as soft, sealed capsules made of gelatin and a plasticizer, such as glycerol or sorbitol. In one embodiment, the push-fit capsules contain the active ingredients in admixture with filler such as lactose, binders such as starches, and/or lubricants such as talc or magnesium stearate and, optionally, stabilizers. In one embodiment, the push-fit capsules contain the active ingredient only without additional inactive ingredients. In one embodiment, in soft capsules, the active compounds are dissolved or suspended in suitable liquids, such as fatty oils, liquid paraffin, or liquid polyethylene glycols. In addition, in one embodiment, stabilizers are added. In other embodiments, the formulation is placed in a sprinkle capsule, wherein the capsule is swallowed whole or the capsule is opened and the contents sprinkled on food prior to eating.

All formulations for oral administration should be in dosages suitable for such administration.

In some embodiments, pharmaceutical formulations are provided comprising Compound I, or a pharmaceutically acceptable salt thereof (e.g. Compound 1 or Compound 2) and at least one dispersing agent or suspending agent for oral administration to a subject. In one embodiment, the formulation is a powder and/or granules for suspension, and upon admixture with water, a substantially uniform suspension is obtained.

A suspension is "substantially uniform" when it is mostly homogenous, that is, when the suspension is composed of approximately the same concentration of Compound I, or a pharmaceutically acceptable salt thereof (e.g. Compound 1 or Compound 2) at any point throughout the suspension (USP Chapter 905).

Liquid formulation dosage forms for oral administration are aqueous suspensions or non-aqueous suspensions.

Liquid formulation dosage forms for oral administration are aqueous suspensions selected from, but not limited to, pharmaceutically acceptable aqueous oral dispersions, emulsions, solutions, and syrups. See, e.g., Singh et al., *Encyclopedia of Pharmaceutical Technology*, $2^{nd}$ Ed., pp. 754-757 (2002). In addition to including Compound I, or a pharmaceutically acceptable salt thereof (e.g. Compound 1 or Compound 2), the liquid dosage forms include additives, such as: (a) disintegrating agents; (b) dispersing agents; (c) wetting agents; (d) preservatives; (e) viscosity enhancing agents; (f) sweetening agents; (g) flavoring agents; (h) solibizing agents (bioavailability enhancers).

In one embodiment, the aqueous suspensions and dispersions described herein remain in a homogenous state, as defined above by USP Chapter 905, for at least 4 hours. Liquid compositions illustratively take the form of a liquid where the agent (e.g. Compound I, or a pharmaceutically acceptable salt thereof (e.g. Compound 1 or Compound 2)) is present in solution, in suspension or both. In one embodiment, the liquid composition is aqueous.

Liquid compositions illustratively take the form of a liquid where the agent (e.g. Compound I, or a pharmaceutically acceptable salt thereof (e.g. Compound 1 or Compound 2)) is present in solution, in suspension or both. In one embodiment, the liquid composition is non-aqueous.

In one embodiment, the aqueous suspension also contains one or more polymers as suspending agents. Useful polymers include water-soluble polymers such as cellulosic polymers, e.g., hydroxypropyl methylcellulose, and water-insoluble polymers such as cross-linked carboxyl-containing polymers. In one embodiment, useful compositions also comprise an mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

In one embodiment, pharmaceutical compositions also include one or more pH adjusting agents or buffering agents, including acids such as acetic, boric, citric, lactic, phosphoric and hydrochloric acids; bases such as sodium hydroxide, sodium phosphate, sodium borate, sodium carbonate, sodium citrate, sodium acetate, sodium lactate and tris-hydroxymethylaminomethane; and buffers such as citrate/dextrose, sodium carbonate, sodium bicarbonate and ammonium chloride. Such acids, bases and buffers are included in an amount required to maintain pH of the composition in an acceptable range.

In one embodiment, liquid pharmaceutical compositions also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In one embodiment, pharmaceutical compositions also include one or more preservatives to inhibit microbial activity.

Still other compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other compositions include one or more antioxidants to enhance chemical stability where required. Suitable antioxidants include, by way of example only, ascorbic acid, tocopherol, and sodium metabisulfite.

In one embodiment, aqueous compositions are packaged in single-dose non-reclosable containers. Alternatively, multiple-dose reclosable containers are used, in which case it is typical to include a preservative in the composition.

In some embodiments, aqueous pharmaceutical compositions do not include a preservative and are used within 24 hours of preparation.

In some embodiments, aqueous pharmaceutical compositions include one or more solubilizers which aid in enhancing the bioavailability of the active pharmaceutical ingredient. In some embodiments, the solubilizer is selected from Labrasol, Lutrol (macrogels, poloxamers), and others known in the art.

The oral pharmaceutical solutions described herein are beneficial for the administration to infants (less than 2 years old), children under 10 years of age and any patient group that is unable to swallow or ingest solid oral dosage forms.

For buccal or sublingual administration, in one embodiment, the compositions take the form of tablets, lozenges, or gels formulated in a conventional manner (see e.g. U.S. Pat. Nos. 4,229,447; 4,596,795; 4,755,386; and 5,739,136).

In one embodiment, dragee cores are prepared with suitable coatings. For this purpose, concentrated sugar solutions are used, which optionally contain gum arabic, talc, polyvinylpyrrolidone, carbopol gel, polyethylene glycol, and/or titanium dioxide, lacquer solutions, and suitable organic solvents or solvent mixtures. In one embodiment, dyestuffs or pigments are added to the tablets or dragee coatings for identification or to characterize different combinations of active compound doses.

It should be understood that many carriers and excipients may serve several functions, even within the same formulation.

In some embodiments, Compound I, or a pharmaceutically acceptable salt thereof (e.g. Compound 1 or Compound 2) is formulated in the form of a pharmaceutical composition that is suitable for inhalation/nasal delivery. In some embodiments, the pharmaceutical composition is in the form of a solution, suspension, emulsion, colloidal dispersion, spray, dry powder, aerosol, or combinations thereof. In some embodiments, the pharmaceutical composition comprises at least one pharmaceutically acceptable excipient that is commonly used in nasal/inhalable pharmaceutical compositions. In some embodiments, the pharmaceutical composition is administered with an atomizer, an insufflator, a nebulizer, a vaporizer, or a metered dose inhaler. In some embodiments, the pharmaceutical composition is inhaled nasally or orally. In some embodiments, crystalline Compound 1 is used in the pharmaceutical composition. In some embodiments, crystalline Compound 2 is used in the pharmaceutical composition. In some embodiments, amorphous Compound 1 is used in the pharmaceutical composition. In some embodiments, amorphous Compound 2 is used in the pharmaceutical composition.

Representative nasal/inhalation formulations are described in, for example, Ansel, H. C. et al., Pharmaceutical Dosage Forms and Drug Delivery Systems, Sixth Ed. (1995); REMINGTON: THE SCIENCE AND PRACTICE OF PHARMACY, 21st edition, 2005.

In some embodiments, Compound I, or a pharmaceutically acceptable salt thereof (e.g. Compound 1 or Compound 2) is formulated in the form of a nasal spray, nasal mist, and the like.

For administration by inhalation, Compound I, or a pharmaceutically acceptable salt thereof (e.g. Compound 1 or Compound 2) is formulated for use as an aerosol, a mist or a powder.

In some embodiments, pharmaceutical compositions suitable for nasal/inhalation administration are conveniently delivered in the form of an aerosol spray presentation from pressurized packs or a nebuliser, with the use of a suitable propellant. Capsules and cartridges for use in an inhaler or insufflator may be formulated containing a powder mix of the compound described herein and a suitable powder base such as lactose or starch.

In some embodiments, the pharmaceutical composition is in the form of a powder for nasal/inhalation delivery to a mammal. In some embodiments, powders comprise micronized and/or nano-sized particles of Compound I, or a pharmaceutically acceptable salt thereof (e.g. Compound 1 or Compound 2), blended with larger carrier particles that prevent aggregation. For example, in one embodiment a dry powder formulation is prepared as follows: Compound I or a pharmaceutically acceptable salt thereof (e.g. Compound 1 or Compound 2) is jet milled. Lactose is jet milled and the two ingredients are mixed and the final mixture is packaged in sterile insufflators. In some instances powder inhalable formulations described herein comprise crystalline particles of Compound 1. In some instances powder inhalable formulations described herein comprise crystalline particles of Compound 2. In some embodiments, powder inhalable formulations described herein comprise amorphous particles of Compound 1. In some embodiments, powder inhalable formulations described herein comprise amorphous particles of Compound 2.

Dose Amounts

In certain embodiments, the effective amount of Compound I, or a pharmaceutically acceptable salt thereof (e.g. Compound 1 or Compound 2) is about 1 mg to about 2.5 g per dose, 1 mg to about 2 g per dose, about 1 mg to about 1.5 g per dose, about 1 mg to about 1 g per dose, about 5 mg to about 600 mg per dose or about 50 mg to about 250 mg per dose. In some embodiments, the effective amount of Compound I, or a pharmaceutically acceptable salt thereof (e.g. Compound 1 or Compound 2) is about 1 mg to about 5 g per day, about 5 mg to about 2 g per day, about 5 mg to about 1 g per day, about 5 mg to about 0.6 g per day, or about 5 mg to about 0.5 g per day.

In some embodiments, the effective amount of Compound I is about 50 mg per dose, about 100 mg per dose, about 150 mg per dose, about 200 mg per dose, about 250 mg per dose, about 300 mg per dose, about 350 mg per dose, about 400 mg per dose, about 450 mg per dose, about 500 mg per dose, about 550 mg per dose, about 600 mg per dose, about 650 mg per dose, about 700 mg per dose, about 750 mg per dose, about 800 mg per dose, about 850 mg per dose, about 900 mg per dose, about 950 mg per dose, about 1000 mg per dose, about 1050 mg per dose, about 1100 mg per dose, about 1150 mg per dose, about 1200 mg per dose, about 1250 mg per dose, about 1300 mg per dose, about 1350 mg per dose, about 1400 mg per dose, about 1450 mg per dose, about 1500 mg per dose, about 1550 mg per dose, about 1600 mg per dose, about 1650 mg per dose, about 1700 mg per dose, about 1750 mg per dose, about 1800 mg per dose, about 1850 mg per dose, about 1900 mg per dose, about 1950 mg per dose, or about 2000 mg per dose.

In some embodiments, oral pharmaceutical solutions include about 6 mg/mL to about 63 mg/mL of Compound 2. In some embodiments, oral pharmaceutical solutions include about 1 mg/mL to about 100 mg/mL of Compound 2. In some embodiments, oral pharmaceutical solutions include about 1 mg/mL to about 100 mg/mL of Compound 1.

In one aspect, tablets include about 5% w/w to about 50% w/w of Compound I, or a pharmaceutically acceptable salt thereof (e.g. Compound 1 or Compound 2). In some embodiments, immediate release tablets include about 5% w/w to about 40% w/w of Compound I, or a pharmaceutically acceptable salt thereof (e.g. Compound 1 or Compound 2). In some embodiments, immediate release tablets include about 5% w/w, about 10% w/w, about 15% w/w, about 20% w/w, about 25% w/w, about 30% w/w, about 33% w/w, about 35% w/w, about 40% w/w of Compound I, or a pharmaceutically acceptable salt thereof (e.g. Compound 1 or Compound 2).

In some embodiments, capsules include Compound I, or a pharmaceutically acceptable salt thereof (e.g. Compound 1 or Compound 2) and the capsule shell only.

Methods of Dosing and Treatment Regimens

In one embodiment, Compound I, or a pharmaceutically acceptable salt or solvate thereof, is used in the preparation of medicaments for the treatment of diseases or conditions in a mammal that would benefit from inhibition or reduction of LOXL2 activity. Methods for treating any of the diseases or conditions described herein in a mammal in need of such treatment, involves administration of pharmaceutical compositions that include Compound I, or a pharmaceutically acceptable salt or solvate thereof, active metabolite, prodrug, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing Compound I, or a pharmaceutically acceptable salt or solvate thereof, are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising Compound I, or a pharmaceutically acceptable salt or solvate thereof, in order to prevent a return of the symptoms of the disease or condition.

In certain embodiments wherein the patient's condition does not improve, upon the doctor's discretion the administration of Compound I, or a pharmaceutically acceptable salt or solvate thereof, is administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%400%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

In one aspect, Compound I, or a pharmaceutically acceptable salt or solvate thereof, is administered daily to humans in need of therapy with Compound I, or a pharmaceutically acceptable salt or solvate thereof. In some embodiments, Compound I, or a pharmaceutically acceptable salt or solvate thereof, is administered once-a-day. In some embodiments, Compound I, or a pharmaceutically acceptable salt or solvate thereof, is administered twice-a-day. In some embodiments, Compound I, or a pharmaceutically acceptable salt or solvate thereof, is administered three times-a-day. In some embodiments, Compound I, or a pharmaceutically acceptable salt or solvate thereof, is administered every other day. In some embodiments, Compound I, or a pharmaceutically acceptable salt or solvate thereof, is administered twice a week.

In general, doses of Compound I, or a pharmaceutically acceptable salt or solvate thereof, employed for treatment of the diseases or conditions described herein in humans are typically in the range of from about 0.1 mg to about 10 mg/kg of body weight per dose. In one embodiment, the desired dose is conveniently presented in a single dose or in divided doses administered simultaneously (or over a short period of time) or at appropriate intervals, for example as two, three, four or more sub-doses per day. In some embodiments, Compound I, or a pharmaceutically acceptable salt or solvate thereof, is conveniently presented in divided doses that are administered simultaneously (or over a short period of time) once a day. In some embodiments, Compound I, or a pharmaceutically acceptable salt or solvate thereof, is conveniently presented in divided doses that are administered in equal portions twice-a-day.

In some embodiments, Compound I, or a pharmaceutically acceptable salt or solvate thereof, is administered orally to the human at a dose from about 0.1 mg to about 10 mg/kg of body weigh per dose. In some embodiments, Compound I, or a pharmaceutically acceptable salt or solvate thereof, is administered to the human on a continuous daily dosing schedule.

The term "continuous dosing schedule" refers to the administration of a particular therapeutic agent at regular intervals. In some embodiments, continuous dosing schedule refers to the administration of a particular therapeutic agent at regular intervals without any drug holidays from the particular therapeutic agent. In some other embodiments, continuous dosing schedule refers to the administration of a particular therapeutic agent in cycles. In some other embodiments, continuous dosing schedule refers to the administration of a particular therapeutic agent in cycles of drug administration followed by a drug holiday (for example, a wash out period or other such period of time when the drug is not administered) from the particular therapeutic agent. For example, in some embodiments the therapeutic agent is administered once a day, twice a day, three times a day, once a week, twice a week, three times a week, four times a week, five times a week, six times a week, seven times a week, every other day, every third day, every fourth day, daily for a week followed by a week of no administration of the therapeutic agent, daily for a two weeks followed by one or two weeks of no administration of the therapeutic agent, daily for three weeks followed by one, two or three weeks of no administration of the therapeutic agent, daily for four weeks followed by one, two, three or four weeks of no administration of the therapeutic agent, weekly administration of the therapeutic agent followed by a week of no administration of the therapeutic agent, or biweekly administration of the therapeutic agent followed by two weeks of no administration of the therapeutic agent. In some embodiments, daily administration is once a day. In some embodiments, daily administration is twice a day. In some embodiments, daily administration is three times a day. In some embodiments, daily administration is more than three times a day.

The term "continuous daily dosing schedule" refers to the administration of a particular therapeutic agent everyday at roughly the same time each day. In some embodiments, daily administration is once a day. In some embodiments, daily administration is twice a day. In some embodiments, daily administration is three times a day. In some embodiments, daily administration is more than three times a day.

In some embodiments, the amount of Compound I, or a pharmaceutically acceptable salt or solvate thereof, is administered once-a-day. In some other embodiments, the amount of Compound I, or a pharmaceutically acceptable salt or solvate thereof, is administered twice-a-day. In some other embodiments, the amount of Compound I, or a pharmaceutically acceptable salt or solvate thereof, is administered three times a day.

In certain embodiments wherein improvement in the status of the disease or condition in the human is not observed, the daily dose of Compound I, or a pharmaceutically acceptable salt or solvate thereof, is increased. In some embodiments, a once-a-day dosing schedule is changed to a twice-a-day dosing schedule. In some embodiments, a three times a day dosing schedule is employed to increase the amount of Compound I, or a pharmaceutically acceptable salt or solvate thereof, that is administered. In some embodiments, the frequency of administration by inhalation is increased in order to provide repeat high Cmax levels on a more regular basis. In some embodiments, the frequency of administration is increased in order to provide maintained or more regular exposure to Compound I, or a pharmaceutically acceptable salt or solvate thereof. In some embodiments, the frequency of administration is increased in order to provide repeat high Cmax levels on a more regular basis and provide maintained or more regular exposure to Compound I, or a pharmaceutically acceptable salt or solvate thereof.

In any of the aforementioned aspects are further embodiments in which the effective amount of Compound I, or a pharmaceutically acceptable salt or solvate thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of Compound I, or a pharmaceutically acceptable salt or solvate thereof, including further embodiments in which (i) Compound I, or a pharmaceutically acceptable salt or solvate thereof, is administered once a day; or (ii) Compound I, or a pharmaceutically acceptable salt or solvate thereof, is administered to the mammal multiple times over the span of one day.

In any of the aforementioned aspects are further embodiments comprising multiple administrations of the effective amount of Compound I, or a pharmaceutically acceptable salt or solvate thereof, including further embodiments in which (i) Compound I, or a pharmaceutically acceptable salt or solvate thereof, is administered continuously or intermittently: as in a single dose; (ii) the time between multiple administrations is every 6 hours; (iii) Compound I, or a pharmaceutically acceptable salt or solvate thereof, is administered to the mammal every 8 hours; (iv) Compound I, or a pharmaceutically acceptable salt or solvate thereof, is administered to the mammal every 12 hours; (v) Compound I, or a pharmaceutically acceptable salt or solvate thereof, is administered to the mammal every 24 hours. In further or alternative embodiments, the method comprises a drug holiday, wherein the administration of Compound I, or a pharmaceutically acceptable salt or solvate thereof, is temporarily suspended or the dose of Compound I, or a pharmaceutically acceptable salt or solvate thereof, being administered is temporarily reduced; at the end of the drug holiday, dosing of Compound I, or a pharmaceutically acceptable salt or solvate thereof, is resumed. In one embodiment, the length of the drug holiday varies from 2 days to 1 year.

In general, doses employed for adult human treatment are typically in the range of 1 mg-5000 mg per day. In some embodiments, doses employed for adult human treatment are from about 1 mg to about 4000 mg per day, about 150 mg to about 4000 mg per day, or about 150 mg to about 2000 mg per day. In some embodiments, 50 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, or 2000 mg of Compound I is administered to the adult human. In some embodiments, the desired dose is conveniently presented in a single dose or in divided doses administered simultaneously or at appropriate intervals, for example as two, three, four or more sub-doses per day.

In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the disease or condition to be treated, the mode of administration, the requirements of the individual subject, the severity of the disease or condition being treated, the identity (e.g., weight) of the human, and the particular additional therapeutic agents that are administered (if applicable), and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of Compound I, or a pharmaceutically acceptable salt or solvate thereof, lies within a range of circulating concentrations that include the $ED_{50}$ with minimal toxicity. In certain embodiments, the daily dosage range and/or the unit dosage amount varies within this range depending upon the dosage form employed and the route of administration utilized.

In some embodiments, the 7-day NOAEL for a rat administered Compound I, or a pharmaceutically acceptable salt or solvate thereof, is at least about 200, 300, 400, 500, 600, 700, 800, 900, or 1000 mpk. In some embodiments, the 7-day NOAEL for a dog administered Compound I, or a pharmaceutically acceptable salt or solvate thereof, is at least about 10, 20, 30, 40, 50, 60, 70, 80, 90, 100, 200, 300 and up to 500 mpk.

Combination Treatments

In certain instances, it is appropriate to administer or formulate Compound I, or a pharmaceutically acceptable salt or solvate thereof, in combination with one or more other therapeutic agents.

Kits and Articles of Manufacture

Described herein are kits for treating a condition, disease or disorder associated with LOXL2 activity comprising administering to said individual Compound I, or a pharmaceutically acceptable salt or solvate thereof.

For use in the therapeutic applications described herein, kits and articles of manufacture are also described herein. In some embodiments, such kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disorder that benefit by inhibition of LOXL2, or in which LOXL2 is a mediator or contributor to the symptoms or cause.

The container(s) optionally have a sterile access port (for example the container is an intravenous solution bag or a vial having a stopper pierceable by a hypodermic injection needle). Such kits optionally comprise a compound with an identifying description or label or instructions relating to its use in the methods described herein.

A kit will typically include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

In some embodiments, a label is on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, a pharmaceutical composition comprising Compound I, or a pharmaceutically acceptable salt or solvate thereof, is presented in a pack or dispenser device which can contain one or more unit dosage forms. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

It is to be understood that as used herein, pharmaceutical compositions described as comprising a pharmaceutically acceptable salt described herein, e.g., liquid solutions, encompass pharmaceutical compositions comprising the associated and/or disassociated forms of the salt. Thus, for example, a pharmaceutical composition described herein comprising an aqueous solution of Compound 2 encompasses a composition comprising a population of methansulfonate anions and a population of (2-(3-((3R,4R)-3-fluoro-4-hydroxypyrrolidine-1-carbonyl)phenoxy)-6-(trifluoromethyl)pyridin-4-yl)methanaminium cations.

EXAMPLES

The following examples are provided for illustrative purposes only and not to limit the scope of the claims provided herein.

Example 1: Preparation of Compound 1 Via Chiral Separation

Compounds 1 and Compound Ent-1 were prepared via chiral separation as shown below.

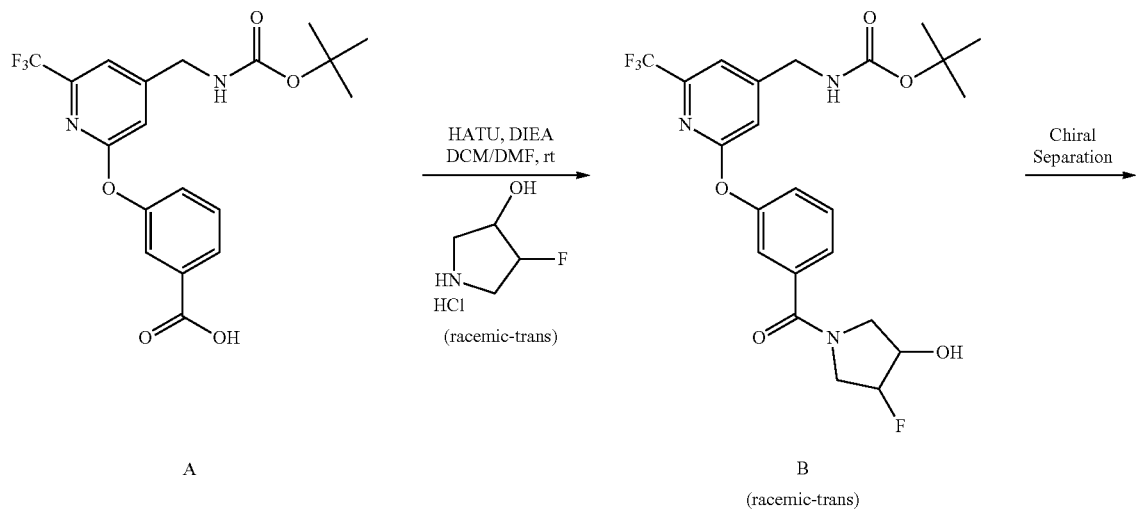

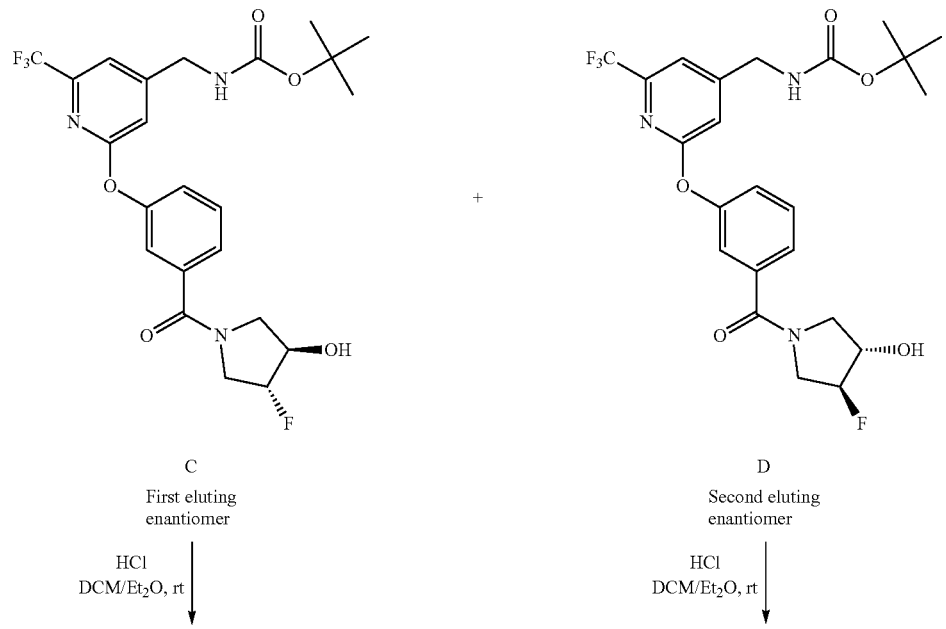

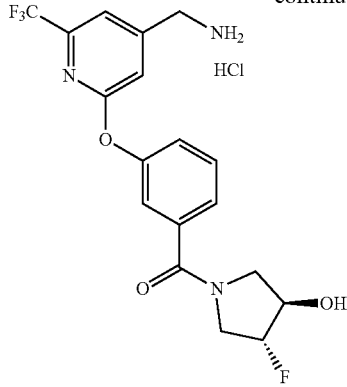

1

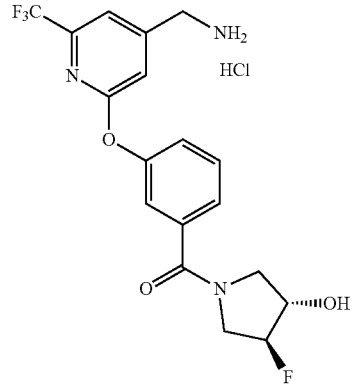

Ent-1

Step 1: Racemic-trans-tert-butyl ((2-(3-(3-fluoro-4-hydroxypyrrolidine-1-carbonyl)phenoxy)-6-(trifluoromethyl)pyridin-4-yl)methyl)carbamate (B)

Two separate equal reaction batches were set up as follows: To a stirred solution of Compound A (750 mg, 1.82 mmol) in a mixture of DCM/DMF (3:1, 11 mL), was added HATU (1.0 g, 2.63 mmol) and the mixture was stirred at RT for 20 min. Racemic-trans-4-fluoro-3-hydroxypyrrolidine hydrochloride (Synthonix; 304 mg, 2.14 mmol) and DIEA (938 mg, 7.27 mmol) were added and the mixture stirred at RT for 2.5 h. At this point both reaction batches were combined and the DCM was evaporated under reduced pressure. The remaining reaction mixture was partitioned between water (200 mL) and EtOAc (200 mL). The organic layer was separated, dried ($Na_2SO_4$), filtered, and then concentrated under reduced pressure. The crude residue was purified (silica gel; eluting with 10-100% EtOAc in hexanes), to afford Compound B (1.58 g, 87%) as a white solid. $^1$H NMR (300 MHz, DMSO-$d_6$): δ 7.60 (m, 1H), 7.47-7.56 (m, 2H), 7.36-7.44 (m, 2H), 7.31 (m, 1H), 7.14 (s, 1H), 5.56 (m, 1H), 4.93 (m, 1H), 4.10-4.30 (m, 3H), 3.45-3.90 (m, 4H), 1.38 (s, 9H); LCMS Mass: 522.0 ($M^+$+Na).

Step 2: (R,R)-trans-tert-Butyl ((2-(3-(3-fluoro-4-hydroxypyrrolidine-1-carbonyl)phenoxy)-6-(trifluoromethyl)pyridin-4-yl)methyl)carbamate (C) and (S,S)-trans-tert-butyl ((2-(3-(3-fluoro-4-hydroxypyrrolidine-1-carbonyl)phenoxy)-6-(trifluoromethyl)pyridin-4-yl)methyl)carbamate (D)

Compound C (102 mg) and Compound D (88 mg) were both obtained from Compound B (300 mg, 0.60 mmol) via chiral HPLC separation (Chiral Pak ADH, 250×20 mm, 5 µm column, eluting isocratically with 10% MeOH:isopropanol (1:1) and 90% hexanes (containing 0.1% DEA), flow rate 18 mL/min), wherein Compound C was the first to elute and Compound D was the second to elute.

Compound C: $^1$H NMR (400 MHz, DMSO-$d_6$): δ 7.59 (m, 1H), 7.47-7.56 (m, 2H), 7.35-7.45 (m, 2H), 7.31 (m, 1H), 7.16 (s, 1H), 5.56 (m, 1H), 4.94 (m, 1H), 4.25-4.30 (m, 2H), 4.17 (m, 1H), 3.45-3.90 (m, 4H), 1.39 (s, 9H); LCMS Mass: 500.0 ($M^+$+1). Chiral HPLC analysis: $R_t$=11.84 min (Chiral Pak ADH, 250×4.6 mm, 5 µm column, eluting isocratically with 10% MeOH:EtOH (1:1) and 90% hexanes (containing 0.1% DEA) over 25 mins; flow rate 1.0 mL/min).

Compound D: $^1$H NMR (400 MHz, DMSO-$d_6$): δ 7.59 (m, 1H), 7.47-7.56 (m, 2H), 7.35-7.45 (m, 2H), 7.31 (m, 1H), 7.16 (s, 1H), 5.56 (m, 1H), 4.95 (m, 1H), 4.25-4.30 (m, 2H), 4.17 (m, 1H), 3.45-3.90 (m, 4H), 1.39 (s, 9H); LCMS Mass: 500.0 ($M^+$+1). Chiral HPLC analysis: $R_t$=14.71 min (Chiral Pak ADH, 250×4.6 mm, 5 µm column, eluting isocratically with 10% MeOH:EtOH (1:1) and 90% hexanes (containing 0.1% DEA) over 25 mins; flow rate 1.0 mL/min).

Step 3: (S,S)-trans-(3-((4-(Aminomethyl)-6-(trifluoromethyl)pyridin-2-yl)oxy)phenyl)(3-fluoro-4-hydroxypyrrolidin-1-yl)methanone hydrochloride salt (Compound Ent-1)

The title compound (Compound Ent-1) (77 mg, 100%) was prepared by dissolving Compound D in DCM (27 mL) at RT. 2 M HCl in $Et_2O$ (9.69 mL, 19.38 mmol) was added and the mixture was stirred at RT for 18 h. Additional 2 M HCl in $Et_2O$ (9 mL, 18.0 mmol) was added and the mixture stirred for a further 2 h. The mixture was concentrated under reduced pressure to afford the title compound (88 mg, 0.176 mmol). $^1$H NMR (300 MHz, DMSO-$d_6$): δ 8.61 (br s, 3H), 7.84 (s, 1H), 7.51-7.57 (m, 2H), 7.43 (m, 1H), 7.28-7.37 (m, 2H), 5.57 (br m, 1H), 4.95 (m, 1H), 4.12-4.30 (br m, 3H), 3.30-3.92 (m, 4H); LCMS Mass: 400.0 ($M^+$+1).

Step 4: (R,R)-trans-(3-((4-(Aminomethyl)-6-(trifluoromethyl)pyridin-2-yl)oxy)phenyl)(3-fluoro-4-hydroxypyrrolidin-1-yl)methanone, hydrochloride salt (1)

The title compound (Compound 1) (89 mg, 100%) was prepared from dissolving Compound D in DCM (27 mL) at RT. 2 M HCl in $Et_2O$ (9.69 mL, 19.38 mmol) was added and the mixture was stirred at RT for 18 h. Additional 2 M HCl in $Et_2O$ (9 mL, 18.0 mmol) was added and the mixture stirred for a further 2 h. The mixture was concentrated under reduced pressure to afford the title compound (102 mg, 0.204 mmol). $^1$H NMR (300 MHz, DMSO-$d_6$): δ 8.61 (br s, 3H), 7.84 (s, 1H), 7.51-7.57 (m, 2H), 7.43 (m, 1H), 7.28-7.37 (m, 2H), 5.62 (br m, 1H), 4.95 (m, 1H), 4.12-4.30 (br m, 3H), 3.30-3.92 (m, 4H); LCMS Mass: 400.0 ($M^+$+1).

Example 2: Preparation of Compound 1 with Enantiomerically Pure (R,R)-4-Fluoro-3-hydroxypyrrolidine hydrochloride Compound 1 was synthesized using enantiomerically pure (R,R)-4-fluoro-3-hydroxypyrrolidine hydrochloride as shown below. Using the same methodology, Compound Ent-1 was prepared from (S,S)-4-fluoro-3-hydroxypyrrolidine hydrochloride.

EtOAc (100 mL) and filtered through celite. The filtrate was concentrated and the resulting residue was partitioned between water (200 mL) and EtOAc (200 mL). The water-

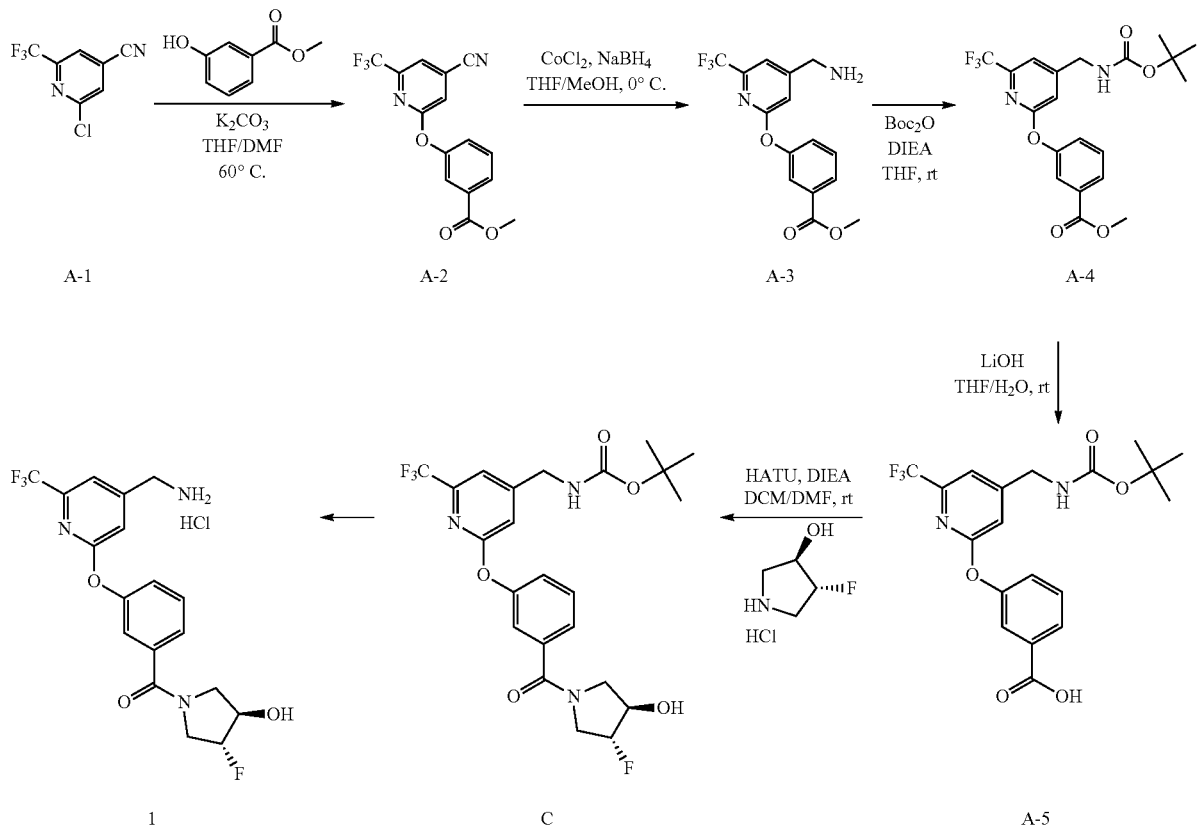

Step 1: Methyl 3-((4-cyano-6-(trifluoromethyl)pyridin-2-yl)oxy)benzoate (Compound A-2)

To a solution of 2-chloro-6-(trifluoromethyl)isonicotinonitrile (Compound A-1) (4.0 g, 19.4 mmol) and methyl 3-hydroxybenzoate (3.24 g, 21.3 mmol) in a mixture of THF/DMF (4:1, 55 ml), was added $K_2CO_3$ (8.0 g, 58 mmol). The reaction mixture was heated at 60° C. for 2 h. The THF was evaporated under reduced pressure and the remaining reaction mixture was partitioned between water (200 mL) and EtOAc (100 mL). The organic layer was separated and the aqueous layer was re-extracted with EtOAc (1×100 mL). The combined organic layers were dried ($Na_2SO_4$), filtered, and then concentrated under reduced pressure. The crude residue was purified (silica gel; eluting with 0-50% EtOAc in hexanes), to afford Compound A-2 as a light yellow solid (5.63 g, 91%). $^1$H NMR (300 MHz, DMSO-$d_6$): δ 8.21 (m, 1H), 8.07 (m, 1H), 7.87 (m, 1H), 7.77 (m, 1H), 7.64 (m, 1H), 7.55 (m, 1H), 3.85 (s, 3H); LCMS Mass: 323.0 ($M^+$+1).

Step 2: Methyl 3-((4-(aminomethyl)-6-(trifluoromethyl)pyridin-2-yl)oxy)benzoate (Compound A-3)

To a stirred solution of methyl 3-((4-cyano-6-(trifluoromethyl)pyridin-2-yl)oxy)benzoate (Compound A-2) (1.5 g, 4.65 mmol) in THF/MeOH (1:1, 140 mL) at 0° C., was added portion-wise $CoCl_2$ (1.8 g, 13.98 mmol) followed by $NaBH_4$ (1.77 g, 46.5 mmol). The reaction mixture was stirred at 0° C. for 20 minutes. The mixture was diluted with organic layer was filtered through celite and the organic layer was separated, dried ($Na_2SO_4$), filtered, and then concentrated under reduced pressure to obtain Compound A-3 as an amber oil (1.38 g, 92%) which did not require further purification. $^1$H NMR (300 MHz, DMSO-$d_6$): δ 7.83 (m, 1H), 7.67 (m, 1H), 7.65 (br m, 1H), 7.60 (m, 1H), 7.47 (m, 1H), 7.33 (br m, 1H), 3.80-3.83 (m, 5H); LCMS Mass: 327.0 ($M^+$+1).

Step 3: Methyl 3-((4-(((tert-butoxycarbonyl)amino)methyl)-6-(trifluoromethyl)pyridin-2-yl)oxy)benzoate (Compound A-4)

To a stirred solution of ester Compound A-3 (1.38 g, 4.24 mmol) in THF (25 mL) at 0° C., was added di-tert-butyl dicarbonate (1.29 g, 5.94 mmol) and DIEA (2.21 mL, 12.74 mmol). The mixture was warmed to RT and stirred for a further 4 h. The mixture was concentrated and the residue partitioned between EtOAc (50 mL) and water (50 mL). The organic layer was separated, dried ($Na_2SO_4$), filtered, and concentrated in vacuo. The residue was purified (silica gel; 0-60% EtOAc in hexanes), to afford Compound A-4 as an amber oil (1.42 g, 78%). $^1$H NMR (300 MHz, DMSO-$d_6$): δ 7.85 (m, 1H), 7.69 (m, 1H), 7.58-7.62 (m, 2H), 7.48-7.51 (m, 2H), 7.13 (br m, 1H), 4.20 (m, 2H), 3.84 (s, 3H), 1.36 (s, 9H); LCMS Mass: 427.0 ($M^+$+1).

Step 4: 3-((4-(((tert-Butoxycarbonyl)amino)methyl)-6-(trifluoromethyl)pyridin-2-yl)oxy)benzoic acid (Compound A-5)

To a stirred solution of ester Compound A-4 (1.42 g, 3.34 mmol) in a mixture of THF/H$_2$O (6:1, 21 mL) was added aqueous 4M LiOH (17 mL, 68 mmol). The mixture was stirred at RT for 16 h, then diluted with water (30 ml) and acidified to pH 3-4 using aq. sat. citric acid. The mixture was extracted with EtOAc (2×50 mL), and the combined organic layers were dried (Na$_2$SO$_4$), filtered, and concentrated under reduced pressure to afford Compound A-5 as an off-white solid (1.2 g, 87%). $^1$H NMR (300 MHz, DMSO-d$_6$): δ 13.17 (br s, 1H), 7.83 (m, 1H), 7.66 (br m, 1H), 7.53-7.62 (m, 2H), 7.44-7.51 (m, 2H), 7.12 (br m, 1H), 4.25 (m, 2H), 1.36 (s, 9H); LCMS Mass: 413.0 (M$^+$+1).

Step 5: tert-Butyl ((2-(3-((3R,4R)-3-fluoro-4-hydroxypyrrolidine-1-carbonyl)phenoxy)-6-(trifluoromethyl)pyridin-4-yl)methyl)carbamate (Compound C)

To a solution of Compound A-5 (160 g, 0.388 mol, 1.0 eq) in a mixture of DCM (2.40 L, 15 Vol) and DMF (0.56 L, 3.5 vol), was added HATU (177 g, 0.466 mol, 1.2 eq). The mixture was stirred for 10 min at ambient temperature, and then (3R,4R)-4-fluoropyrrolidin-3-ol hydrochloride (71.5 g, 0.466 mol, 1.3 eq) and DIPEA (0.226 L, 1.37 mol, 3.5 eq) were added to above solution. The resulting mixture was stirred at ambient temperature for 1.5 h. After the reaction was completed as evidence by HPLC analysis, the DCM was removed under reduced pressure.

The residue was partitioned between water (1.0 L) and EtOAc (1.0 L). The combined organic layers were dried (Na$_2$SO$_4$), filtered and the filtrate was concentrated under reduced pressure. The crude residue was purified by chromatography (silica gel: eluting with 20-50% EtOAc in PE). The elution was concentrated under reduced pressure to afford colorless oil. The oil was diluted with EtOAc (3.0 L), and then washed with 5% NaHCO$_3$ solution. The organic layer was concentrated under reduced pressure to afford Compound C (160 g) as a white solid. Yield: 82%, HPLC purity: 95.1% area.

Step 6: (3-((4-(Aminomethyl)-6-(trifluoromethyl)pyridin-2-yl)oxy)phenyl)((3R,4R)-3-fluoro-4-hydroxypyrrolidin-1-yl)methanone, hydrochloride salt (Compound 1)

To a solution of Compound C (151 g, 0.3 mol, 1.0 eq) in DCM (3.37 L, 22 Vol) was added 6.6N HCl in MTBE (695 mL, 6.9 mol, 23 eq). The reaction mixture was stirred at ambient temperature overnight. After the reaction was completed as evidence by HPLC analysis, the mixture was concentrated under reduced pressure to afford a yellow solid. The solid was slurried in MTBE (400 mL) and filtered. The wet cake was washed with MTBE and dried to afford Compound 1 (110 g) as a yellow solid. Yield: 83%, HPLC purity 98.4% area, ee: 100%. (DAICEL Chiralcel AD-H column: 5 μm×4.6*150 mm, 80% HEX/10% MeOH/10% EtOH with 0.1% DEA).

Example 3: Preparation of Compound 2

In some embodiments, Compound 2 is prepared by using enantiomerically pure R,R-4-fluoro-3-hydroxypyrrolidine hydrochloride as below.

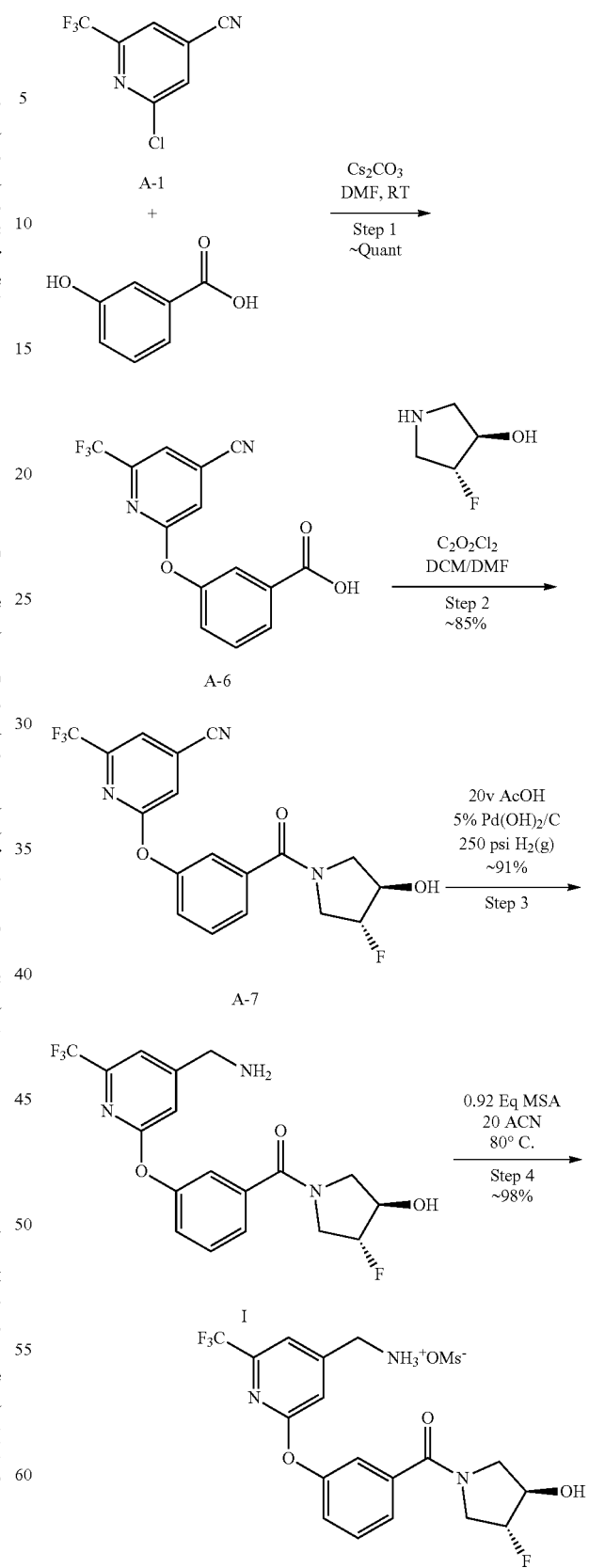

Step 1: 3-((4-Cyano-6-(trifluoromethyl)pyridin-2-yl)oxy)benzoic acid (Compound A-6)

20 g of 2-chloro-6-(trifluoromethyl)isonicotinonitrile (Compound A-1) and Cs$_2$CO$_3$ (78 g, 0.242 mol, 2.5 eq) were suspended in 80 mL DMF in the reactor. A solution of 3-hydroxybenzoic acid (13.4 g, 0.096 mol, 1.0 eq) in 40 mL DMF, was slowly added to the reactor maintaining the temperature below 30° C. The reactor's contents were heated to 30±5° C. and aged until reaction completion (69 hours). The reaction was deemed completed with Compound A-1=1%. The reaction mixture was diluted with 1 L purified process H$_2$O and washed with 2×200 mL EtOAc. The pH of the aqueous solution was ~9 and was adjusted to pH ~3-4 via the addition of 97 mL of 3M HCl(aq) while maintaining a temperature of 20±5° C. The aqueous layer was extracted 2×300 mL with EtOAc and the organic layers were washed with 150 mL brine, dried (Na$_2$SO$_4$) and concentrated to dryness for afford compound A-6. Appearance: tan solid. Mass=29.98 g

Step 2: 2-(3-((3R,4R)-3-Fluoro-4-hydroxypyrrolidine-1-carbonyl)phenoxy)-6-(trifluoromethyl)isonicotinonitrile (Compound A-7)

The 3-((4-cyano-6-trifluoromethyl)pyridine-2-yl)oxy)benzoic acid (Compound A-6) was telescoped in DCM from Step 1, by concentrating down to 100 mL based on theoretical yield of Compound A-6. Maintaining a temperature of 0±5° C., the reactor was charged with oxalyl chloride, (1.2 eq) and allowed to slowly warm to room temperature over 1 hour. After 2 hours, the conversion was deemed complete. (3R,4R)-4-Fluoropyrrolidin-3-ol hydrochloride was combined with 150 mL DMF and 350 mL DCM. Maintaining a temperature of 0±5° C., the acid chloride of A-6 was added to the solution of (3R,4R)-4-fluoropyrrolidin-3-ol hydrochloride, followed by the slow addition of 3.5 eq DIPEA.

The reaction was quenched with 40 mL H$_2$O and the DCM was distilled off, resulting in a DMF/H$_2$O mixture of Compound A-7 which was diluted with 720 mL MTBE, then washed with 3×600 mL H$_2$O, 1×400 mL Brine, dried (Na$_2$SO$_4$), and concentrated down to 100 ml. The concentrate was allowed to crystallize over 20 hours, then charged with 15v heptane, and then aged an additional 20 hours. The solid was collected via filtration, then rinsed with 2×50 mL Heptane, and dried at 45° C. to constant weight to give Compound A-7. Appearance=white solid; Mass=16.5, theoretical 18.94 g; HPLC=98%

Step 3: 3-((4-(Aminomethyl)-6-(trifluoromethyl)pyridin-2-yl)oxy)phenyl)((3R,4R)-3-fluoro-4-hydroxypyrrolidin-1-yl)methanone (Compound I)

Combined 16 g of Compound A-7, 350 mL AcOH, 5% Pd(OH)$_2$/C into a degassed reactor pressurized with 250 PSI H$_2$(g) for 3 hours. The material was polish filtered, rinsed with 700 mL H$_2$O at 0±5° C., and quenched with 50% NaOH—used 16.9v to pH-11. Extracted 2×20v EtOAc, aged for 2 hour, then cut the layers, and warmed to 25±5° (salts are in solution while above 25° C.) to give Compound I. HPLC=91.1%, 7.026 min; Mass=16.44 g; Yield=101%-quantitative.

Step 4: (3-((4-(Aminomethyl)-6-(trifluoromethyl)pyridin-2-yl)oxy)phenyl)((3R,4R)-3-fluoro-4-hydroxypyrrolidin-1-yl)methanone, methanesulfonate salt (Compound 2)

8.0 g of Compound I was converted to the MSA salt (Compound 2) by diluting Compound I in 160 mL ACN, slowly adding MSA, and adjusting the MSA concentration by HPLC purity. The solution was aged for 1 hour at 20±5° C. and heated to reflux (~82°-85° C.) for 2 hours. The mixture was allowed to stir over night at room temperature and the heating cycle was repeated 3 more times until the DSC conformed (total reflux hold time 10 hours) to give Compound 2. HPLC=99.5%; Mass=7.36 g; ee=99.7% (DAICEL Chiralcel OD-H column: 5 μm×4.6*150 mm, 90% HEX/10% IPA with 0.1% DEA).

Example 4: Preparation of (3R,4R)-4-fluoropyrrolidin-3-ol-hydrochloride (C6)

In some embodiments, Compound C6 is prepared as shown below.

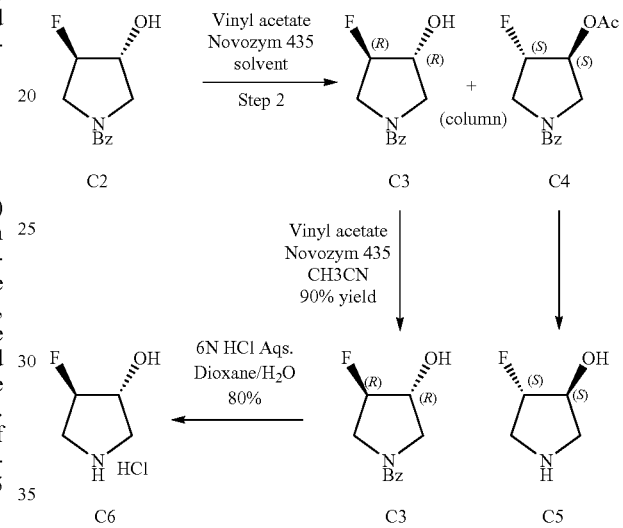

Step 1: ((3R,4R)-3-Fluoro-4-hydroxypyrrolidin-1-yl)(phenyl)methanone (Compound C3)

190.0 kg of Acetone was charged into the reactor, followed by 50 kg of Compound C2. The reaction mixture was mixed at 20-25° C. for 15 minutes. 15.6 kg of vinyl acetate and 2 kg of Novozyme® 435 were charged into the reactor The Reaction mixture was mixed at 20-25° C. for 37 hours. The reaction progress was monitored by Chiral HPLC until Compound C3 (ee %) >95.0%. The mixture was filtered and the cake was washed with 10 kg of acetone. The acetone was removed under reduced pressure at 40-50° C. for 11 hours to give 10.5 kg of crude Compound C3. This was charged into the reactor, followed by 16.0 kg of silica gel and 14.0 kg of DCM and the slurry was mixed at 20-25° C. for 15 minutes. 3.60 kg of silica gel was loaded onto chromatographic column, followed by 6.3 kg of petroleum ether. 0.90 kg of Na$_2$SO$_4$ followed by an additional 6.3 kg of petroleum ether were loaded onto the column for 30 minutes. 60 L of a mixture DCM (70.2 kg) and of EtOAc (5.34 kg) were loaded onto the column. 2.9 kg of Compound C3 was obtained after evaporation (ee %=94.9 DAICEL Chiralcel OD-H column: 5 μm×4.6*150 mm, 90% HEX/10% IPA with 0.1% DEA).

Step 2: (3R,4R)-3-Fluoro-4-hydroxypyrrolidin-1-yl)(phenyl)methanone (Compound C3)

75 kg of Acetone was charged into the reactor, followed by 2.9 kg of Compound C3. The reaction mixture was mixed at 20-25° C. for 15 minutes. 6.0 kg of vinyl acetate and 2.8 kg of Novozyme® 435 were charged into the reactor The reaction mixture was mixed at 20-25° C. for 54 hours. The reaction progress was monitored by Chiral HPLC until Compound C3 (ee %) >99.5%. The mixture was filtered and the cake was washed with 5.5 kg of acetone. The acetone was removed under reduced pressure at 40-50° C. for 6 hours to give 2.5 kg of crude Compound C3. The 2.5 kg of Compound C3 was charged into the reactor, followed by 3.8 kg of Silica gel and 14.0 kg of DCM and the slurry was mixed at 20-25° C. for 30 minutes. 3.60 kg of silica gel was loaded onto chromatographic column, followed by 5.3 kg of petroleum ether. 0.50 kg of $Na_2SO_4$ followed by an additional 6.3 kg of petroleum ether were loaded onto the column for 30 minutes. 60 L of a mixture DCM (70.2 kg) and of EtOAc (5.34 kg), followed by 50 L of EtOAc were loaded onto the column (repeated 3 times). 2.0 kg of Compound C3 was obtained after evaporation (ee %=99.1 DAICEL Chiralcel OD-H column: 5 μm×4.6*150 mm, 90% HEX/10% IPA with 0.1% DEA)

Step 3: (3R,4R)-4-Fluoropyrrolidin-3-ol hydrochloride (Compound C6)

12.0 kg of 1,4-Dioxane into the reactor followed by 2.40 kg of Compound C3. The reaction mixture was mixed at 20-25° C. for 15 minutes and 12.0 kg of concentrated hydrochloric acid was charged into the reactor and the 1,4-dioxane was evaporated under reduced pressure at 65-75° C. for 5 hours. 15.0 kg of DCM into the reactor and the reaction mixture was mixed at 20-25° C. for 15 minutes followed by evaporation under reduced pressure (repeated 4 times). The remaining water was removed reduced pressure at 65-75° C. for 5 hours. 20.0 kg of methylbenzene was added into the spin steaming bottle and removed under reduced pressure at 40-50° C. for 6 hours to give 1.54 kg of Compound C6 (ee %=99.1 DAICEL Chiralcel OD-H column: 5 μm×4.6*150 mm, 90% HEX/10% IPA with 0.1% DEA).

Example 5: Determination of Absolute Configuration of (3R,4R)-4-fluoropyrrolidin-3-ol hydrochloride (Compound C6)

In some embodiments, the absolute configuration of the (R,R)-4-fluoropyrrolidin-3-ol hydrochloride (Compound C6) was determined by x-ray crystallography analysis of C7.

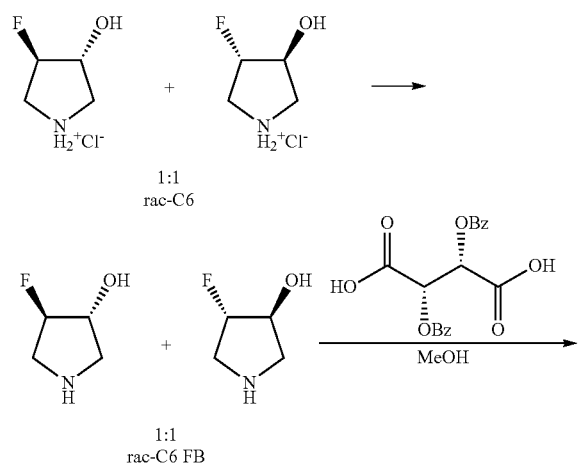

1:1
rac-C6

1:1
rac-C6 FB

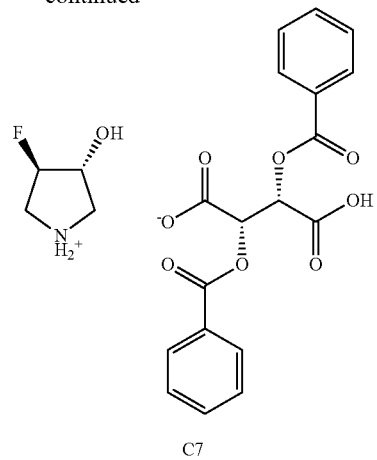

C7

Step 1:
racemic-trans-3-Fluoro-4-hydroxypyrrolidine
(rac-C6 FB)

To a solution of NaOH (2.83 g, 70.6 mmol) in EtOH (100 mL), racemic-trans-3-fluoro-4-hydroxypyrrolidine hydrochloride (rac-C6) (10 g, 70.6 mmol) was added. Then the above solution was stirred at room temperature for 1 h. The precipitation was filtered and the filtrate was concentrated to give free base (rac-C6 FB) as a brown liquid (7.0 g).

Step 2: (3R,4R)-3-Fluoro-4-hydroxypyrrolidin-1-ium(2S,3S)-2,3-bis(benzoyloxy)-3-carboxypropanoate salt C7

(3R,4R)-3-Fluoro-4-hydroxypyrrolidin-1-ium(2S,3S)-2, 3-bis(benzoyloxy)-3-carboxypropanoate salt was formed by the treatment of racemic-trans-3-fluoro-4-hydroxypyrrolidine (rac-C6 FB) with (2S,3S)-2,3-bis(benzoyloxy)-3-carboxypropanoic acid and repeatedly recrystallized from methanol to yield the substantially pure enantiomer corresponding to C6 by chiral HPLC (94.4% ee; DAICEL Chiralcel AD-H column: 5 μm×4.6*150 mm, 90% HEX/10% IPA with 0.1% DEA). X-Ray crystallography confirmed the (R,R) configuration.

Example 6: Alternative Synthetic Process for Compound 2

In some embodiments, Compound 2 is prepared as shown below.

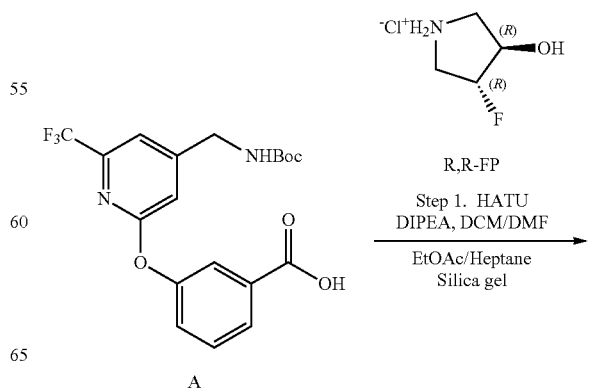

A

R,R-FP

Step 1. HATU
DIPEA, DCM/DMF

EtOAc/Heptane
Silica gel

-continued

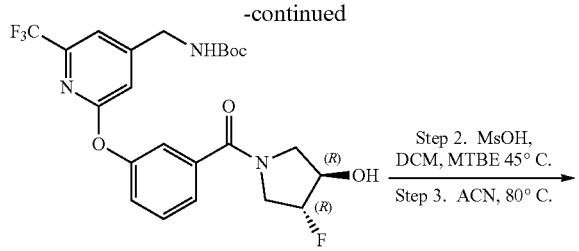

Step 2. MsOH, DCM, MTBE 45° C.
Step 3. ACN, 80° C.

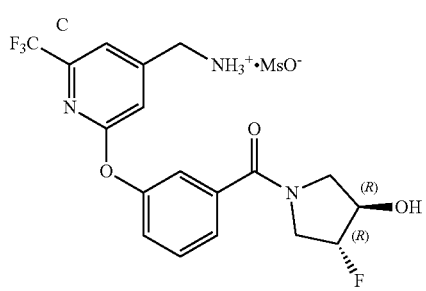

Compound 2

Combined 3-(4-(((tert-butoxycarbonyl)methyl)-6-(trifluoromethyl)pyridin-2-yloxy)benzoic acid (1.0 eq) (Compound A), (3R,4R)-4-fluoropyrrolidin-3-ol hydrochloride ((R,R)-FP) (1.4 eq), HATU (1.2 eq), and dichloromethane (DCM) (32 kg). While agitating slowly, 5.2 kg N,N-dimethylformamide (DMF) and 3.5 eq N,N-diisopropylethylamine (DIPEA) were added. The reaction was heated to reflux until complete. The DCM was then removed under vacuum. Compound C in DMF was diluted with EtOAc and washed with water and brine. Crude Compound C was concentrated to dryness and purified via silica plug using a gradient with final elution solvent ratio 7:3 EtOAc/heptane. All Compound C fractions were concentrated and washed with sodium bicarbonate solution, water, brine, and dried with $Na_2SO_4$. Concentration of the organics afforded Compound C with 98% high-performance liquid chromatography (HPLC) purity and 98.5% yield.

tert-Butyl (2-(3-((3R,4R)-3-fluoro-4-hydroxypyrrolidine-1-carbonyl)phenoxy)-6-(trifluoromethyl)pyridin-4-yl)methylcarbamate (Compound C) was dissolved in DCM, transferred to the reactor, and diluted with DCM. Methanesulfonic acid (0.93 eq) was charged and the reaction heated to reflux and stirred over night until being deemed complete. At this point the thick white slurry was diluted with DCM, cooled and filtered, and rinsed with methyl-tert-butyl-ether (MTBE). The organics were concentrated to afford Compound 2 in 98.5% HPLC purity and 91% yield.

Compound 2 was triturated in acetonitrile and heated for approximately 4 hours and then cooled to 20° C. A sample of solid was removed and dried to test for residual DCM and acetonitrile (ACN). The trituration was repeated until residual DCM and ACN was below the limits of 1200 parts per million (ppm) and 820 ppm, respectively. The purity of Compound 2 was monitored by HPLC to control impurity formation. The process produced Compound 2 at 99.3% HPLC purity and 91% recovery.

Example 7: Chemical Purity Determination

A reverse phase HPLC method was developed to measure purity and related substances.

TABLE 1

| HPLC Method Parameters for Chemical Purity Determination | |
|---|---|
| Column | Agilent Eclipse XDB-$C_8$, 5 μm column (4.6 mm × 150 mm) |
| Mobile Phase A | 0.1% TFA in water: 90% to 0% |
| Mobile Phase B | 0.1% TFA in acetonitrile: 10% to 100% |
| Detection | UV: λ = 275 nm |
| Column Temperature | 25° C. |
| Injection Volume | 5.0 μL |
| Flow Rate | 1.0 mL/min. |
| Acquisition Time | 20 minutes |

Samples of Compound 2 were found to be greater than 90% pure. In some embodiments, samples of Compound 2 were found to be greater than 95% pure, greater than 96% pure, greater than 97% pure, greater than 98% pure, or greater than 99% pure.

In some embodiments, samples of Compound 2 include a detectable amount of at least one of the following compounds:

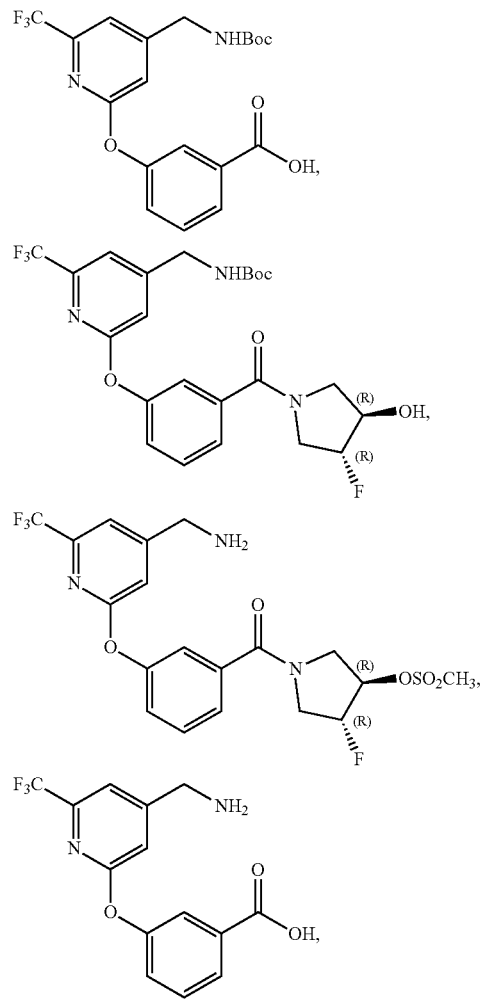

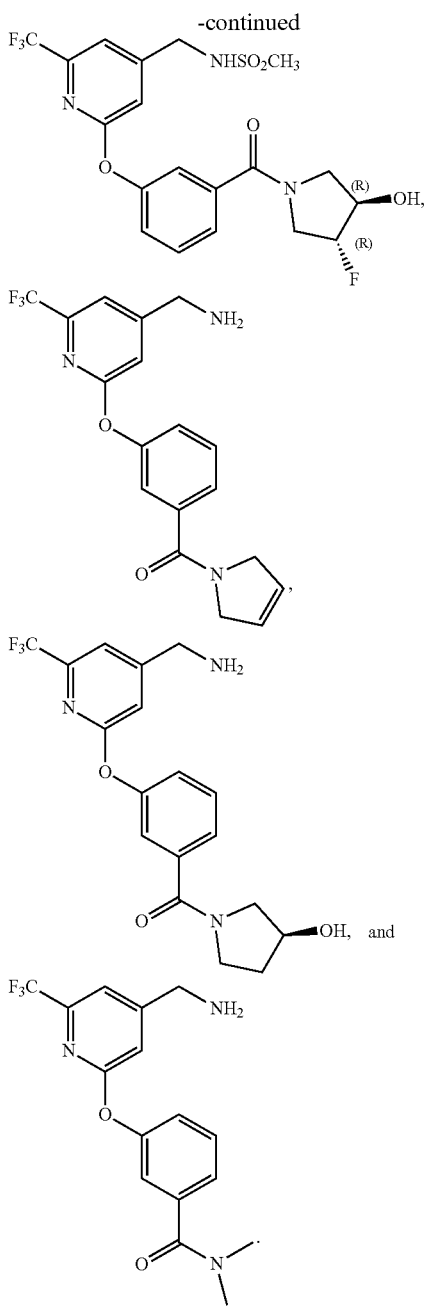

In some embodiments, samples of Compound 2 do not include a detectable amount of the compounds noted above.

Example 8: Chiral Purity Determination

Chiral HPLC was used to measure chiral purity. The following conditions were used.

TABLE 2

| HPLC Method Parameters for Optical Purity Determination | |
|---|---|
| Column | ChiralPak IC-3, 3 μm column |
| | (4.6 mm × 250 mm) |
| Mobile Phase: | 0.05% ESA in hexane/EtOH (75:25 v/v). |
| Detection | UV: λ = 220 nm |
| Column Temperature | 15° C. |

TABLE 2-continued

| HPLC Method Parameters for Optical Purity Determination | |
|---|---|
| Injection Volume | 10 μL |
| Flow Rate | 1.0 mL/min. |
| Acquisition Time | 45 minutes |

The chiral purity (area %) is determined by the peak area response for each enantiomer.

Samples of Compound 2 have a chiral purity of greater than 90% enantiomeric excess (e.e.). In some embodiments, samples of Compound 2 have a chiral purity of greater than 95%, greater than 96%, greater than 97%, greater than 98%, or greater than 99% e.e. In some embodiments, samples of Compound 2 have a chiral purity of 100% e.e.

In some embodiments, samples of Compound 2 include a detectable amount of the (S,S)-enantiomer of Compound 2. In some embodiments, samples of Compound 2 do not include a detectable amount of the (S,S)-enantiomer of Compound 2.

Example 9: Residual (R,R)-FP Determination

A reverse phase HPLC method was developed to measure residual (R,R)-FP [(3R,4R)-4-fluoropyrrolidin-3-ol].

TABLE 3

| HPLC Method Parameters for Residual (R,R)-FP Determination | |
|---|---|
| Column | Agilent Eclipse Plus C18 column |
| | (4.6 mm × 100 mm, 3.5 μm) |
| Mobile Phase A | 0.05% TFA in water: 55% to 0% |
| Mobile Phase B: | 0.05% TFA in ACN: 45% to 100% |
| Detection | λ = 235 |
| Column Temperature | 20° C. |
| Injection Volume | 1.0 μL |
| Flow Rate | 1.0 mL/min. |
| Acquisition Time | 15 minutes |

Samples of Compound 2 contain less than 5% of (3R, 4R)-4-fluoropyrrolidin-3-ol. In some embodiments, samples of Compound 2 contain less 5%, 4%, 3%, 2%, or 1% of (3R,4R)-4-fluoropyrrolidin-3-ol.

Example 10: Residual Solvents

Residual solvents were determined by gas chromatography, using USP G43 capillary column with flame ionization detection (FID). The sample solution is prepared in NMP at 10 mg/mL.

Potential residual solvents include methanol, acetone, isopropanol, acetonitrile, dichloromethane, t-butylmethylether, hexane, ethyl acetate, tetrahydrofuran, cyclohexane, heptane, dioxane, isobutylmethylketone, toluene, and dimethylformamide.

In some embodiments, compound 2 contains a detectable amount of at least one of the following: dichloromethane, ethyl acetate, heptane, t-butylmethylether, acetone, dimethylformamide, and acetonitrile.

Example 11: Polymorph Screening of Compound 1

Preliminary Solubility Assessment

Amorphous Compound 1 (30 mg) was treated with increasing volumes of solvent until the compound had fully dissolved or until a maximum of 100 vol had been used. After each addition of solvent, the system was shaken gently for 10 minutes at 50° C. and then allowed to stand at room temperature for 5 min before the addition of a new aliquot of solvent. After the assessment was completed, any suspensions obtained were matured and clear solutions were cooled at 5° C. Table 4 shows the results of these studies.

TABLE 4

Solubility Assessment

| Solvent | 5 vol RT | 5 vol 50°C. | 10 vol RT | 10 vol 50°C. | 20 vol RT | 20 vol 50°C. | 50 vol RT | 50 vol 50°C. | 70 vol RT | 70 vol 50°C. | 100 vol RT | 100 vol 50°C. | Solubility mg/mL | XRPD |
|---|---|---|---|---|---|---|---|---|---|---|---|---|---|---|
| Toluene | x | x | x | x | x | x | x | x | ☑ | ☑ | ☑ | ☑ | <10 | n/a |
| Dichloromethane | x | x | x | x | x | x | x | x | x | x | x | x | <10 | n/a |
| Tetrahydrofuran (THF) | x | x | x | x | x | x | x | x | x | x | x | x | <10 | Form 1 |
| 2-Propanol | ☑ | ✓ | | | | | | | | | | | >200 | n/a |
| Ethanol | ☑ | ✓ | | | | | | | | | | | >200 | n/a |
| Ethyl Acetate | x | x | x | x | x | x | x | x | x | x | x | x | <10 | Form 1 |
| Nitromethane | x | ☑ | ☑ | ☑ | ☑ | x | x | x | x | x | x | x | <10 | n/a |
| Acetonitrile | x | x | x | x | x | x | x | x | x | x | x | x | <10 | Form 1 |
| Dimethoxyethane | x | x | x | x | x | x | x | x | x | x | x | x | <10 | Form 1 |
| THF:water 95:5 | ☑ | x | ✓ | | | | | | | | | | 200-100 | Form 1 |

Maturation

Suspensions obtained after the solubility assessment were shaken in the maturation chamber between 25-50° C. (8 h cycles). After 3 days the solids were filtered and air dried. Solids obtained were initially analysed by XRPD, as shown in Table 5.

TABLE 5

Polymorphism screen results from maturation (cycling between 25-50° C.)

| Procedure | Solvent | Volume (µL) | Final Temperature (° C.) | Isolation | XRPD |
|---|---|---|---|---|---|
| Maturation | Toluene | 3000 | 25 | Filtration | 2 peaks - Form 1 |
| Maturation | Dichloromethane | 3000 | 25 | Filtration | Form 1 |
| Maturation | Tetrahydrofuran | 3000 | 25 | Filtration | Form 1 |
| Maturation | Ethyl Acetate | 3000 | 25 | Filtration | Form 1 |
| Maturation | Nitromethane | 3000 | 25 | Filtration | Form 1 |
| Maturation | Acetonitrile | 3000 | 25 | Filtration | Form 1 |
| Maturation | Dimethoxyethane | 3000 | 25 | Filtration | Form 1 |

Cooling

Solutions obtained after the solubility assessment were placed in a fridge (5° C.) for 3 days. The solids were air dried and the residues were analysed by XRPD, shown in Table 7.

TABLE 6

Polymorphism screen results from cooling at 5° C.

| Procedure | Solvent | Volume (µL) | Final Temperature (° C.) | Isolation | XRPD |
|---|---|---|---|---|---|
| Cooling | 2-Propanol | 150 | 5 | Drying at RT | Form 1 |
| Cooling | Ethanol | 150 | 5 | Drying at RT | Form 1 |
| Cooling | Tetrahydrofuran:water 95:5 | 300 | 5 | Drying at RT | Form 1 |

Evaporation

Supernatants from maturation were allowed to slowly evaporate at ambient conditions. No solids were recovered.

Discussion of Results

During the solubility assessment, some samples displayed an evident visual change after the addition of the solvent (see Table 4). Solids did not dissolve but had a different texture. Therefore, a small amount of solid was retrieved and analysed by XRPD before continuing with the solubility assessment. All diffractograms showed a crystalline pattern, named Form 1 of Compound 1. The solubility value in such circumstances does not correlate to an absolute value in mg/ml but rather to a volume at which the crystallisation occur. After XRPD analysis, solids were stored at 40° C. and 75% RH, deliquescing after 24 hours.

Additional crystallisation attempts were carried via several approaches including heat/cool cycles, cooling and slow evaporation. Form 1 of Compound 1 was obtained from maturation and at 5° C. No solids were recovered after evaporating the supernatants, thus indicating that the formed Form 1 of Compound 1 is insoluble in those solvents.

All retrieved solids from the crystallisation attempts were stored at 40° C. and 75% RH. After 12 days, they transformed to a glassy solid surrounded by some droplets. They remained crystalline by XRPD but a new pattern, Form 2 of Compound 1 was displayed.

Form 2 of Compound 1 was left upon storage conditions for 1 week. It remained unchanged.

Characterisation of the New Crystalline Forms

Two new crystalline patterns, Form 1 and Form 2 of Compound 1, were identified during the polymorph screen. The characterisation results of these two forms in addition to the amorphous form are summarised in Table 7.

TABLE 7

Characterisation of Polymorphs of Compound 1

| | Amorphous | Form 1 | Form 2 |
|---|---|---|---|
| Salt Form | HCl salt | HCl salt | HCl salt |
| XRPD | Amorphous trace | Form 1 | Form 2 |
| $^1$H-NMR | Consistent with structure | Consistent with structure | Consistent with structure |
| DSC | No re-crystallisation events observed | Endotherm (153.1° C., 51.3 J/g) | Endotherm (43.1° C., 17.9 J/g): Endotherm (118.9° C., 32.2 J/s) |

TABLE 7-continued

Characterisation of Polymorphs of Compound 1

| | Amorphous | Form 1 | Form 2 |
|---|---|---|---|
| 7 days storage @ 40° C./ 5% RH | Glassy material | Waxy/glassy solid + deliquescence of small particles - Form 2 | Waxy/glassy solid + deliquescence of small particles - Form 2 |
| IC | 1:1 | 1:1 | 1:1 |

$^1$H-NMR did not reveal any relevant amount of solvent or degradation in any of the crystalline solids studied. This result is corroborated by the DSC trace observed for Form 1 of Compound 1, where no significant events are observed before the relatively high melt (153.1° C.), indicating that Form 1 of Compound 1 is more likely an anhydrous form.

In the case of Form 2 of Compound 1, a broad event at 43° C. was seen before an endotherm at 118.9° C. representing the solid melting. This indicates that Form 2 of Compound 1 is more likely a hydrate form.

Based on these results, Form 1 of Compound 1 is a hygroscopic form, which rearranges itself to accommodate the water, changing its structure to Form 2 of Compound 1. Once the water is released, DSC data showed a different melting point from Form 1 of Compound 1, lower, indicating it does not revert back to Form 1 of Compound 1. A new anhydrous form could possibly be formed through the dehydration process of Form 2 of Compound 1.

Additionally, to quick estimate the aqueous solubility of Form 1 of Compound 1 in water, a brief solubility assessment was carried out. A mixture of Form 1 samples were weighed out in vials and aliquots of water were added at 25° C. as shown in Table 8. Form 1 displayed a solubility of at least 1000 mg/mL.

TABLE 8

Water solubility of Form 1 of Compound 1

| Sample (mg) | Water (μL) | Result |
|---|---|---|
| 30 | 150 μL (2.5 vol) | Dissolved |
| 10 | 10 μL (1 vol) | Dissolved |

Example 12: Salt Screening of Compound I

Commercial chemicals and solvents were purchased from Aldrich or Fluka. Acid stock solutions used in the screen were prepared as shown in Table 9.

TABLE 9

Stock Solutions Used in Salt Screen

| Counter-ion | Concentration | Solvent |
|---|---|---|
| Sulfuric acid - SO4 | 1.0M | THF |
| Methanesulfonic acid - MSA | 1.0M | THF |
| Maleic acid - MEA | 1.0M | THF |
| Phosphoric acid - PHOA | 1.0M | THF |
| L-Tartaric acid - TAR | 1.0M | THF |
| Fumaric acid - FUA | 0.5M | MeOH:THF 1:1 |
| Succinic acid - SUCA | 1.0M | Methanol |
| Acetic acid - AcOH | 1.0M | THF |

Preliminary Free Base Solubility Assessment

Compound I (10 mg) was treated with increasing volumes of solvent until the material fully dissolved or until a maximum of 50 vol had been used). After each addition of solvent, the system was shaken at 50° C. for 10 min and then allowed to stand at room temperature for 5 min before the addition of a new aliquot of solvent.

After the assessment was completed, systems were heated to 50° C. and treated with 1.1 eq of HCl (1M in THF, 27.5 μL). The solutions/suspensions were left at 50° C. for 1 hour and then cooled down to 5° C. at 0.1° C./min and stirred at this temperature overnight. Recovered solutions were allowed to evaporate to dryness at ambient conditions Table 10 shows the initial results of the solubility assessment.

TABLE 10

Solubility Assessment of Compound I

| Solvent | Solubility | After evaporation of solutions |
|---|---|---|
| Toluene | >20 mg/mL | Gum |
| Dichloromethane | >100 mg/mL | Gum |
| Tetrahydrofuran | >100 mg/mL | Gum |
| 2-Propanol | >100 mg/mL | Gum |
| Ethanol | >100 mg/mL | Gum |
| Ethyl Acetate | >100 mg/mL | Gum |
| Hexane | >100 mg/mL | Gum |
| Acetonitrile | >100 mg/mL | Gum |

No crystalline material was recovered from any of the initial experiments. Additional techniques/approaches were carried out to recover crystalline solids and are described hereafter.

Sonication

Gums were placed in the ultrasonic bath. After 1 hour no change was noticed. 100 μl of each solvent was added and they were placed in the ultrasonic bath for an additional hour to favour precipitation. They remained as gums.

Maturation

Recovered gums from sonication (still with 100 μl of solvent) were matured for 12 hours (cycling between 25-50° C.). Solutions were recovered.

Cooling

After maturation, solutions were placed in the freezer (−20° C.) overnight. No precipitation occurred, however a gum was recovered.

Drying Under Vacuum

Solutions and gum obtained at −20° C. were allowed to dry at room temperature and they were placed in the oven (25° C./vacuum) over the weekend. Two solids were recovered from EtOH and ACN respectively. These solids were amorphous and the peak shifts observed with respect to the free base observed in the $^1$H-NMR suggest salt formation has occurred. Based on these results, ethanol and acetonitrile were selected for the salt screen.

General Procedure (EtOH)

Compound I (15 mg) was dissolved in EtOH at 50° C. The solutions were treated with the selected counter-ions and stirred for 1 hour at 50° C. The solutions were then cooled down to 5° C. at 0.1° C./min and stirred at this temperature over the weekend. Suspension was allowed to dry at room temperature. Solutions were evaporated at ambient conditions and the recovered oils were placed in the oven (RT/vacuum). All solids were analysed by XRPD. Table 12 shows the results of the salt screen.

TABLE 11

Salt Screen Results (EtOH)

| Solvent | Counter-ion | After addition of acid | At 5° C. | After drying in oven (25° C./vacuum) - XRPD |
|---|---|---|---|---|
| Ethanol | Sulfuric acid - SO4 | Solution | Solution | Oil - no XRPD |
| Ethanol | Methanesulfonic acid - MSA | Solution | Suspension | n/a - Crystalline pattern (Form 1, Compound 2) |
| Ethanol | Maleic acid - MEA | Solution | Solution | Solid - Amorphous[1] |
| Ethanol | Phosphoric acid - PHOA | Solution | Solution | Solid - Amorphous |
| Ethanol | L-Tartaric acid - TAR | Solution | Solution | Solid - Amorphous |
| Ethanol | Fumaric acid - FUA | Solution | Solution | Oil - no XRPD |
| Ethanol | Succinic acid - SUCA | Solution | Solution | Oil - no XRPD |
| Ethanol | Acetic acid - AcOH | Solution | Solution | Oil - no XRPD |

[1]Solid was recovered after 1 week under vacuum.

General Procedure (Acetonitrile)

Compound I (15 mg) was dissolved in acetonitrile at 50° C. The solutions were treated with the selected counter-ions. The solutions were stirred for 1 hour at 50° C., cooled down to 5° C. at 0.1° C./min and stirred at this temperature overnight. Suspension was allowed to dry at room temperature. Gums were placed in the maturation chamber (cycling between 25-50° C., 8H cycle) for 24 hours, followed by drying in the oven (RT/vacuum). Solutions were evaporated at ambient conditions and the recovered oils were placed in the oven (RT/vacuum). All solids were analysed by XRPD. Table 12 shows the results of the salt screen.

TABLE 12

Salt screen results (Acetonitrile)

| Solvent | Counter-ion | After addition of acid | At 5° C. | After drying in oven (25° C./vacuum) - XRPD |
|---|---|---|---|---|
| Acetonitrile | Sulfuric acid - SO4 | Solution | Solution | Solid - Amorphous |
| Acetonitrile | Methanesulfonic acid - MSA | Suspension | Suspension | n/a - Crystalline pattern (Form 1, Compound 2) |
| Acetonitrile | Maleic acid - MEA | Solution | Solution | Oil - no XRPD |
| Acetonitrile | Phosphoric acid - PHOA | Suspension | Gum | Solid - Amorphous |
| Acetonitrile | L-Tartaric acid - TAR | Suspension | Gum | Solid - Amorphous |
| Acetonitrile | Fumaric acid - FUA | Solution | Solution | Oil - no XRPD |
| Acetonitrile | Succinic acid - SUCA | Solution | Solution | Oil - no XRPD |
| Acetonitrile | Acetic acid - AcOH | Solution | Solution | Oil - no XRPD |

Example 13: Preparation of Form 1 of Compound 2

Compound I (500 mg) were dissolved in acetonitrile (3623 µL). 1.1 equivalents of methanesulfonic acid were slowly added (1380 µL) through a peristaltic pump (Vt=5 mL, 10 vol). A very thick suspension was obtained therefore an additional 5 mL of solvent were added to favor stirring. Suspension was left stirring at 25° C. during 1 one hour and a cycle was set for 24 hours:

Ramp to 5° C. at 0.2° C./min 2H at 5° C.

Ramp to 25° C. at 0.2° C./min 2H at 25° C.

At 25° C., a white suspension was recovered. It was filtered (0.45 µm) and left air drying over the weekend. 471.6 mg of Form 1 of Compound 2 (76% yield) was obtained and confirmed via XRPD analysis.

In another embodiment, Form 1 of Compound 2 was obtained by dissolving 1.0 g of Compound 2 in 10v ACN refluxing for 24 hrs. The solution was cooled, filtered, and dried under vacuum to provide the title compound.

The properties of the crystalline Form 1 of Compound 2 are shown in the Table 13.

TABLE 13

Characterization Details for Form 1 of Compound 2

| | |
|---|---|
| Salt form | Mesylate (1 equivalent) |
| Appearance: | White to pale yellow solid |
| Thermal Gravimetric Analysis (TGA) | 0.7% w/w loss (from 78° C. to 243° C.), degradation above 250° C. |
| Differential Scanning Calorimetry (DSC) | Endotherm at ~231.05° C. (82.7 J/g) - small shoulder observed |
| Specific rotation: | 14 ± 2° (c = 0.02 g/mL, methanol) at λ = 589.2 |

| Aqueous Solubility: | pH | Solubility |
|---|---|---|
| | pH 2 | >107 mg/mL (Freely soluble) |
| | pH 7.4 | >107 mg/mL (Freely soluble) |
| | pH 10 | >85 mg/mL (Soluble) |

| Organic Solubility: | Solvents | Qualitative Solubility |
|---|---|---|
| | water, dimethyl sulfoxide | >200 mg/mL (Freely soluble) |
| | methanol tetrahydrofuran/water (90:10) | ~100 mg/mL (Freely soluble) |
| | Ethanol/Water (90:10) isopropanol/water (90:10) | ~50 mg/mL (Soluble) |
| | EtOH | ~15 mg/mL (Sparingly soluble) |
| | isopropyl acetate, isopropanol, methyl-ethyl ketone, acetone, ethanol, methyl-t-butyl ether, 1,4 dioxane, toluene, tetrahydrofuran, dichloromethane, acetonitrile | ≤10 mg/mL (Slightly soluble) |

TABLE 13-continued

Characterization Details for Form 1 of Compound 2

| | |
|---|---|
| Hygroscopicity (Gravimetric Vapor Sorption [GVS]): | Reversible water uptake (~2.1% w/w) between 0 and 90% RH |
| | X-ray powder diffraction (XRPD): Unchanged |
| Crystallinity: | Crystalline |
| Polymorphs: | Form 1, which is stable for 7 days at 40° C./75% RH and 25° C./97% RH |

Example 14: Crystallization Studies of Compound 2

Compound 2 (20 mg) was weighed out into vials and solvents were added (100 μL, 5 vol) aiming at obtaining slurries. Suspensions were placed in the maturation chamber (cycling between 25-50° C.) for 24 hours and recovered solids were analysed by XRPD. Table 14 summarizes the crystallation studies.

TABLE 14

Crystallization studies

| Salt (mg) | Solvent | Volume (μL) | XRPD |
|---|---|---|---|
| 20 | Toluene | 100 | Form 1, Compound 2 |
| 20 | Dichloromethane | 100 | Form 1, Compound 2 |
| 20 | Tetrahydrofuran | 100 | Form 1, Compound 2 |
| 20 | 2-Propanol | 100 | Form 1, Compound 2 |
| 20 | Ethanol | 100 | Form 1, Compound 2 |
| 20 | Ethyl Acetate | 100 | Form 1, Compound 2 |
| 20 | Nitromethane | 100 | Form 1, Compound 2 |
| 20 | Acetonitrile | 100 | Form 1, Compound 2 |
| 20 | 1,2-Dimethoxyethane | 100 | Form 1, Compound 2 |
| 20 | Tetrahydrofuran:water 95:5 | 100 | Form 1, Compound 2 |

Example 15: Screen for Other Potential Salts from Compound I

Procedure for Forming Other Salts

Compound I (100/50 mg) were dissolved in acetonitrile/ethanol (10 vol). 1.1 eq of counter-ions were slowly added and suspensions were left stirring at 25° C. during 1 hour. A cycle was set for 24 hours:

Ramp to 5° C. at 0.2° C./min 2H at 5° C.

Ramp to 25° C. at 0.2° C./min 2H at 25° C.

At 25° C., a mixture of solutions, gums and a white solid were recovered, which transformed to gums upon drying at room temperature. Gums were placed in the oven (25° C./vacuum) and yellow solids were recovered and analysed by XRPD. Table 15 shows the procedures of making these salts.

TABLE 15

Procedure of Making Other Salts

| Weight (mg) | Solvent | Volume (μl) | Counter-ion | Equivalents | Volume (μl) | Observations after addition of counter-ion |
|---|---|---|---|---|---|---|
| 100 | Acetonitrile | 1000 | Sulfuric acid—SO4 | 1.1 | 275 | Suspension transformed to gum after 175 μL |
| 100 | Acetonitrile | 1000 | Phosphoric acid—PHOA | 1.1 | 275 | Remained as suspension |
| 100 | Acetonitrile | 1000 | L-Tartaric acid—TAR | 1.1 | 275 | Suspension transformed to gum after 200 μL |
| 50 | Acetonitrile | 500 | Citric acid—CA | 1.1 | 138 | Suspension transformed to gum after 125 μL |
| 50 | Ethanol | 500 | Citric acid—CA | 1.1 | 138 | Remained as solution |

Procedure of Crystallisation Studies on Other Salts

Amorphous salts were triturated, weighed out into vials and solvents were added (5 vol). Suspensions were placed in the maturation chamber (cycling between 25-50° C.) for 24 hours. Solutions were left evaporating and recovered solids were analysed by XRPD. Table 16 shows the results of making these salts.

TABLE 16

Results with Other Salts

| Counter-ion | Observations after maturation cycle | Observations after drying at RT | Yield after drying in oven |
|---|---|---|---|
| Sulfuric acid - SO4 | Solution | Gums | 53% |
| Phosphoric acid - PHOA | Gum | Gums | 77% |
| L-Tartaric acid - TAR | White solid | Gums | 70% |
| Citric acid - CA | Gum | Gums | 62% |
| Citric acid - CA | Solution | Gums | 54% |

[1] Indication of hygroscopicity for this salt

After the addition of the counter ion, only one white thick suspension was formed (phosphate salt), however it transformed to a gum after maturation. Tartrate salt crystallised after maturation cycle but it became a gum upon drying, indicating its ability to take water. Remaining salts were either solutions or gums.

Sulfuric acid was used to form the sulfate salt of Compound I. Crystallization studies with the sulfate salt of Compound I was carried out with the following solvents: toluene, dichloromethane, tetrahydrofuran, 2-propanol, ethanol, ethyl acetate, nitromethane, acetonitrile, 1,2-dimethoxyethane, and tetrahydrofuran/water (95:5). Oils were obtained.

Phosphoric acid was used to form the phosphate salt of Compound I. Crystallization studies with the phosphate salt of Compound I was carried out with the following solvents: toluene, dichloromethane, tetrahydrofuran, 2-propanol, ethanol, ethyl acetate, nitromethane, acetonitrile, 1,2-dimethoxyethane, and tetrahydrofuran/water (95:5). Amorphous compound was obtained with toluene and dicloromethane; and oils were obtained with the other solvents.

L-Tartaric acid was used to form the tartrate salt of Compound I. Crystallization studies with the tartrate salt of Compound I was carried out with the following solvents: toluene, dichloromethane, tetrahydrofuran, 2-propanol, ethanol, ethyl acetate, nitromethane, acetonitrile, 1,2-dimethoxyethane, and tetrahydrofuran/water (95:5). Oils were obtained from ethanol and tetrahydrofuran:water (95:5) while amorphous compound was obtained from other solvents.

Citric acid was used to form the citrate salt of Compound I from acetonitrile. Crystallization studies with the citrate salt of Compound I was carried out with the following solvents: toluene, dichloromethane, tetrahydrofuran, 2-propanol, ethanol, ethyl acetate, nitromethane, acetonitrile, 1,2-dimethoxyethane, and tetrahydrofuran/water (95:5). Amorphous compound was obtained from toluene and dichloromethane while oils were obtained from other solvents.

Citric acid was used to form the citrate salt of Compound I from ethanol. Crystallization studies with the citrate salt of Compound I was carried out with the following solvents: toluene, dichloromethane, tetrahydrofuran, 2-propanol, ethanol, ethyl acetate, nitromethane, acetonitrile, 1,2-dimethoxyethane, and tetrahydrofuran/water (95:5). Oils were obtained.

Example 16: Preparation of Form 2 of Compound 2

The crystalline Form 2 of Compound 2 was obtained by dissolving Compound 2 (700 mg) in EtOH (49 mL) at 50° C. The solution was stirred at 50° C. and after 15 min the stirring was stopped. n-Heptane was added (70 mL) and the system was placed in a dry ice/acetone bath for 2 hr. The solid was filtered, air-dried and characterised Example 17: Preparation of Form 3 of Compound 2

The crystalline Form 3 of Compound 2 was obtained by dissolving Compound 2 in DMSO at 50° C. The solution was stirred at 50° C. and after 15 min the stirring was stopped. MeCN was added and the system was cooled to RT or 5° C. or dry ice/acetone.

Example 18: Preparation of Form 4 of Compound 2

The crystalline Form 4 of Compound 2 was obtained by treating 8.0 g of (R,R)-trans-(3-((4-(aminomethyl)-6-(trifluoromethyl)pyridin-2-yl)oxy)phenyl)(3-fluoro-4-hydroxy-pyrrolidin-1-yl)methanone (Compound I) in 160 mL ACN with 0.92 eq of methanesulfonic acid. The solution was allowed to stand for 1 hour at 20±5° C. and then heated to reflux (~82°-85° C.) for 2 hours, allowed to stir over night at room temperature, repeated heating cycle 3 more times until DSC conformed, total reflux hold time 10 hours. The crystalline compound was isolated by filtrating and drying under vacuum.

Example 19: Conversion of Compound 2 Mixture of Form 1 and 4 to Compound 2 Form 1

Compound 2 (a mixture of Forms 1 and 4) was treated with cooled IPA:water (95:5; 1 mL) and heated from −8 to 70° C. at a rate of 0.5° C./min. The samples were then cooled from 70 back to −8° C. at the same rate. The clear point upon heating (at 100% transmission) and the cloud point upon re-cooling (<100% transmission) were recorded using the Crystal16 instrument and the data is shown in Table 17. XRPD analysis was performed on all solids obtained post cooling. XRPD analysis of the isolated solids post cooling revealed Form 1 to be the only isolated form.

TABLE 17

Summarisation of the solubility and metastable limit curves

| Sample Weight (mg) | Clear Point Temperature (° C.) | Cloud Point Temperature (° C.) |
|---|---|---|
| 5 | 6.9 | N/A |
| 10 | 20.3 | N/A |
| 20 | 37.2 | N/A |
| 30 | 48.5 | −7.8 |
| 40 | 55.8 | −1.8 |
| 60 | 64 | 14.5 |
| 70 | 68.6 | 24.7 |
| 100 | N/A | N/A |

Example 20: Stability Studies

Stability studies were performed according to the conditions shown in Table 18. The compounds were assayed according to appearance, purity, related Substances, chiral purity, moisture, DSC, and XRPD

TABLE 18

Stability Studies

| Study | Storage Condition |
|---|---|
| 3 Month accelerated Forced degradation: | 40° C./75% RH<br>Acid (2N HCl)<br>Base (0.33N NaOH)<br>Peroxide (10% $H_2O_2$)<br>Solution, Heat (50° C., 24 h.)<br>Solution, Light (365 nm, 24 hours)<br>Solid Heat (100° C., 24 hours)<br>Solid Light (365 nm, 24 hours) |
| 1-year ICH Stability | 25° C./60%<br>40° C./75% |
| 2-year ICH Stability | 25° C./60%<br>40° C/75% |

ICH = International Conference on Harmonisation;
RH = relative humidity.

Compound 1

Compound 1 showed no significant changes in purity or absorption of moisture for the 3 month accelerated condition (40° C./75% RH).

Compound 2

For Compound 2, the 1 month data for long-term and accelerated conditions of the 1-year ICH study and the 2-year ICH study are within limits for all attributes tested, with no notable chemical or physical changes.

Example 21: Forced Degradation Studies

A forced degradation study of Compound 2 was performed using the HPLC chemical purity conditions of Example 7.

Solid State

Compound 2 was stable as a solid exposed to heat (100° C., 24 hours) and light (max 365 nm, 24 hours).

Solution State

Compound 2 was stable when heated in solution (50° C. for 24 hours). No significant changes in related substances or purity were noted.

Example 22: X-Ray Powder Diffraction (XRPD)

Bruker AXS C2 GADDS

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Gobel multilayer mirror coupled with a pinhole collimator of 0.3 mm. A weekly performance check is carried out using a certified standard NIST 1976 Corundum (flat plate).

The beam divergence, i.e. the effective size of the X-ray beam on the sample, was approximately 4 mm. A θ-θ continuous scan mode was employed with a sample-detector distance of 20 cm which gives an effective 2θ range of 3.2°-29.7°. Typically the sample would be exposed to the X-ray beam for 120 seconds. The software used for data collection was GADDS for XP/2000 4.1.43 and the data were analysed and presented using Diffrac Plus EVA v15.0.0.0.

Samples run under ambient conditions were prepared as flat plate specimens using powder as received without grinding. Approximately 1-2 mg of the sample was lightly pressed on a glass slide to obtain a flat surface.

Bruker AXS D8 Advance

X-Ray Powder Diffraction patterns were collected on a Bruker D8 diffractometer using Cu Kα radiation (40 kV, 40 mA), 0-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.6.1 and the data were analysed and presented using Diffrac Plus EVA v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection are:
- Angular range: 2 to 42° 2θ
- Step size: 0.05° 2θ
- Collection time: 0.5 s/step Form 1 of Compound 1

The X-Ray powder diffraction pattern for Form 1 is displayed in FIG. 9. Characteristic peaks include the peaks listed in the following table:

| Angle 2-Theta ° | Intensity % |
| --- | --- |
| 5.5 | 100 |
| 7.5 | 61 |
| 18.5 | 40.5 |
| 19.4 | 41.9 |
| 20.2 | 27.7 |
| 21.8 | 54.6 |
| 23.5 | 48.7 |
| 25.2 | 27.1 |
| 26.6 | 27.5 |

Form 2 of Compound 1

The X-Ray powder diffraction pattern for Form 2 is displayed in FIG. 11. Characteristic peaks include the peaks listed in the following table:

| Angle 2-Theta ° | Intensity % |
| --- | --- |
| 6.6 | 34.9 |
| 13.2 | 37.1 |
| 19.7 | 100 |
| 22.3 | 45.5 |
| 22.5 | 53.4 |
| 23.7 | 40.2 |
| 24.5 | 45 |
| 26.4 | 49.3 |

FIG. 11 shows the X-Ray powder diffraction pattern for Form 2 after storage at 40° C. and 75% RH for 7 days.

Form 1 of Compound 2

The X-Ray powder diffraction pattern for Form 1 is displayed in FIG. 1. Characteristic peaks include the peaks listed in the following table.

| Angle (2-Theta °) | Intensity (%) |
| --- | --- |
| 13.6 | 37.1 |
| 14.0 | 22.6 |
| 15.4 | 26.6 |
| 16.9 | 90.3 |
| 17.3 | 24.3 |
| 18.3 | 30.7 |
| 19.4 | 75.7 |
| 20.1 | 52.2 |
| 20.3 | 60.1 |
| 20.6 | 40.4 |
| 21.3 | 29 |
| 22.6 | 27 |
| 23.1 | 100 |
| 23.6 | 36.6 |
| 27.9 | 30.2 |

Form 2 of Compound 2

The X-Ray powder diffraction pattern for Form 2 is displayed in FIG. 3. Characteristic peaks include the peaks listed in the following table.

| Angle (2-Theta °) | Intensity (%) |
| --- | --- |
| 2.6 | 38.5 |
| 3.2 | 100 |
| 6.3 | 12.9 |
| 9.4 | 13.2 |
| 15.7 | 96.3 |
| 22.1 | 14.6 |

Form 3 of Compound 2

The X-Ray powder diffraction pattern for Form 3 is displayed in FIG. 5. Characteristic peaks include the peaks listed in the following table.

| Angle (2-Theta °) | Intensity (%) |
| --- | --- |
| 2.9 | 63.1 |
| 3.2 | 67.5 |
| 3.3 | 59.9 |
| 3.8 | 20.5 |
| 9.5 | 11.9 |
| 13.5 | 26.2 |
| 15.8 | 100 |
| 16.9 | 91.1 |
| 19.0 | 10.4 |
| 19.5 | 13.9 |
| 20.2 | 59.8 |
| 22.2 | 21.9 |

Form 4 of Compound 2

The X-Ray powder diffraction pattern for Form 4 is displayed in FIG. 7. Characteristic peaks include the peaks listed in the following table:

| Angle 2-Theta ° | Intensity % |
| --- | --- |
| 11.3 | 27.9 |
| 13.3 | 30.4 |
| 13.9 | 45.6 |
| 16.6 | 98.1 |
| 18.8 | 100 |
| 19.1 | 44.4 |
| 19.7 | 56.5 |
| 19.9 | 70.7 |
| 20 | 43.7 |
| 21.2 | 83.7 |
| 22.3 | 60 |
| 22.7 | 59.4 |
| 23.4 | 74.5 |
| 23.8 | 81.9 |

Example 23: Differential Scanning Calorimetry (DSC) and Thermogravimetric Analysis (TGA)

DSC data were collected on a TA Instruments Q2000 equipped with a 50 position auto-sampler. The calibration for thermal capacity was carried out using sapphire and the calibration for energy and temperature was carried out using certified indium. Typically 0.5-3 mg of each sample, in a pin-holed aluminium pan, was heated at 10° C./min from 25° C. to 300° C. A purge of dry nitrogen at 50 ml/min was maintained over the sample.

The instrument control software was Advantage for Q Series v2.8.0.394 and Thermal Advantage v5.5.3 and the data were analysed using Universal Analysis v4.5A.

TGA data were collected on a TA Instruments Q500 TGA, equipped with a 16 position auto-sampler. The instrument was temperature calibrated using certified Alumel and Nickel. Typically 5-10 mg of each sample was loaded onto a pre-tared aluminium DSC pan and heated at 10° C./min from ambient temperature to 350° C. A nitrogen purge at 60 ml/min was maintained over the sample.

The instrument control software was Advantage for Q Series v2.5.0.256 and Thermal Advantage v5.5.3 and the data were analysed using Universal Analysis v4.5A.

Amorphous Compound 1

An endotherm having a temperature at about 66.8° C. was observed. A broad endotherm starting at about 200° C. was observed. TGA revealed a weight loss of ca. 2% from 25° C. to 130° C. with degradation observed starting at about 280° C. This event corresponds to the endotherm at 70° C. observed in the DSC. No significant amounts of solvent (less than 0.02 eq of diethyl ether) were apparent by $^1$HNMR thus indicating that Compound 1 is more likely to contain ca. 0.5 molecules of water based on the TGA weight loss.

Form 1 of Compound 1

An endotherm having a temperature of about 153.1° C. was observed, wherein no significant events were observed before the relatively high melt. From this, Form 1 is more likely an anhydrous form. A representative thermogram for Form 1 is displayed in FIG. 10.

Form 2 of Compound 1

A broad event at 43.1° C. was seen before an endotherm at 118.9° C. representing the solid melting. This indicates that Form 2 is more likely a hydrate form. A representative thermogram for Form 2 is displayed in FIG. 12.

Form 1 of Compound 2

An endotherm is observed at about 230.5° C. with a small shoulder observed. A representative thermogram for Form 1 is displayed in FIG. 2. TGA analysis revealed a 0.7% w/w/loss from 78° C. to about 243° C. with degradation observed at above 250° C.

Form 1 is an anhydrous mesylate salt.

Form 2 of Compound 2

Three endotherms were at about 121.7° C., 231.1° C. and 236.1° C. A representative thermogram for Pattern 4 is displayed in FIG. 4.

Form 2 is most likely an anhydrous mesylate salt.

Under thermal analysis, it displays three endothermic peaks: the first peak matched Form 1 followed by a melt which presented two peaks. The second endotherm is considered to be the melt of Form 2. The heat of fusion rule points towards an enantiotropic system between Form 1 and Form 2.

Form 2 can transform to Form 1 when it is heated above 150° C.

$^1$H-NMR showed ca. 0.1 equivalents of ethanol, which roughly matches with the weight loss observed by TGA. The first event could be the desolvation of the ethanol.

Form 3 of Compound 2

Two endotherms were observed at about 132.2° C. and 238.8° C. A representative thermogram for Form 3 is displayed in FIG. 6.

Form 3 is suspected of being a DMSO solvate. A XRPD changed to Form 1 was observed when heating the sample to 130° C. and upon the storage conditions, which could indicate that Form 3 is a metastable solvate that transforms to Form 1.

Form 4 of Compound 2

An endotherm is observed at about 232.8° C. with a small shoulder observed. A representative thermogram for Form 4 is displayed in FIG. 8.

Form 4 is an anhydrous mesylate salt.

Example 24: Gravimetric Vapor Sorption (GVS)

Gravimetric Vapor Sorption (GVS) isotherms were obtained using an SMS DVS Intrinsic moisture sorption analyser, controlled by DVS Intrinsic Control software v1.0.1.2 (or v 1.0.1.3), over a range of 0 to 90% relative humidity (RH).

Form 1 of Compound 2

Testing Form 1 of Compound 2 showed a reversible water uptake (~2.1% w/w) between 0 and 90% RH. The XRPD was unchanged after the GVS analysis.

Form 2 of Compound 2

Form 2 undergoes a phase transformation towards Form 1 (although not entirely identical) after GVS analysis and 7 days at 40° C./75% RH. The change also occurs after 7 days at 25° C./97% RH.

Example A-1: Capsule Formulation of Compound 1

Compound 1 was directly added to a size 9 capsule (Torpac, Inc., New Jersey).

Example A-2: Tablet Formulations of Compound 2

Two different tablet formulations were manufactured at 50 mg and 250 mg strengths (based on amount of Compound I). Tablets are manufactured using standard tableting techniques.

TABLE 19

Formulation A
250 mg dose (Compound I)

| | Wt % | Wt per Tablet (mg) | Wt per 50-g batch (g) |
|---|---|---|---|
| Compound 2 | 35.27% | 317.42 | 17.634 |
| Prosolv HD90 | 55.73% | 501.58 | 27.866 |
| Ac-Di-Sol | 5.00% | 45.00 | 2.500 |
| HPC Klucel EXF | 3.00% | 27.00 | 1.500 |
| Aerosil 200 | 0.50% | 4.50 | 0.250 |
| Magnesium Stearate | 0.50% | 4.50 | 0.250 |
| Total | 100.00% | 900.00 | 50.000 |

TABLE 20

Formulation B
250 mg dose (Compound I)

| | Wt % | Wt per Tablet (mg) | Wt per 50-g batch (g) |
|---|---|---|---|
| Compound 2 | 35.27% | 317.42 | 17.634 |
| Avicel PH102 | 14.06% | 126.52 | 7.029 |
| Parteck M200 (Mannitol) | 42.17% | 379.56 | 21.087 |
| Explotab | 5.00% | 45.00 | 2.500 |
| PVP VA 64 | 3.00% | 27.00 | 1.500 |
| PRUV | 0.50% | 4.50 | 0.250 |
| Total | 100.00% | 900.00 | 50.000 |

Two different tablet strength formulations were manufactured at 50 mg and 250 mg strengths (based on amount of Compound I). Tablets are manufactured according to standard tableting techniques and stored at 20° C. to 25° C. The tablets are formulated as a direct blend and compressed into 900 mg capsule shaped tablets.

TABLE 21

Composition of Compound 2 Tablets, 50 mg (Compound I)

| Component | Amount per Tablet - (% wt) |
|---|---|
| Compound 2 | 62.46 mg (6.94%) |
| Silicified microcrystalline cellulose | 756.5 mg (84.1%) |
| Croscarmellose sodium | 45.00 mg (5.0%) |
| Hydroxypropylcellulose | 27.00 mg (3.0%) |
| Collodial silicon dioxide | 4.50 mg (0.5%) |
| Magnesium Stearate | 4.50 mg (0.5%) |
| Total | 900 mg |

TABLE 21

Composition of Compound 2 Tablets, 250 mg (Compound I)

| Component | Amount per Tablet - (% wt) |
|---|---|
| Compound 2 | 312.3 mg (34.7%) |
| Prosolv HD90 | 506.7 mg (56.3%) |
| Ac-Di-Sol ® | 45.00 mg (5.0%) |
| HPC Klucel EXF | 27.00 mg (3.0%) |
| Aerosil 200 | 4.50 mg (0.5%) |
| Magnesium Stearate | 4.50 mg (0.5%) |
| Total | 900 mg |

Briefly, Compound 2 tablet batches were manufactured under conditions as follows: Add excipients (except lubricant) and compound 2 to a V-shell blender. Order of addition: half of the filler, super disintegrant, dry binder, glidant, Compound 2, and finally the remaining filler. Blend for 10 minutes. Then co-mill through an 813 µm Round Flat screen at 50% power or 2000 to 3000 rotations per minute (rpm). Return the co-milled blend to the V-shell blender and mix for an additional 10 minutes. Screen magnesium stearate. Add the screened magnesium stearate to the blend and mix in a V-shell blender for 2 minutes. Compress tablets using a using tooling of 0.400"×0.750" capsule tablet shape, plain-faced to a tablet weight of 900 mg. Package tablets in HDPE bottles and seal with CRC.

Blend uniformity was performed after mixing and milling the blend with exception of magnesium stearate. After the blend was prepared, tablets were produced to the proper weight (900 mg) and hardness (18 kp; range 15-21 kp). Friability was measured and was <1.0%. Tablets were randomly weight checked to a tolerance of ±5%. Each tablet was visually inspected for defects, such as capping, cracking, or misshape and rejected for any defect noted.

The tablets contain a white to off-white capsule shaped tablet.

Example B-1: Preparation of Concentrated Conditioned Media (CCM)

Human LOXL2/CHO and human LOX/HEK stable cell lines were cultured under normal growth conditions in 15 cm tissue culture plates until cells were ~80% confluent. Cells were then washed with PBS before the addition of 25-30 mL serum-free media (Phenol red-free DMEM/F12 mix w/glutamax containing pen/strep, 10-100 µM $CuCl_2$±0.1% BSA). Cells were incubated at 37° C., 5% $CO_2$ in serum-free media for 40-48 hours before the conditioned media was removed and centrifuged at 2000 rpm for 5 min at 4° C. to pellet cells/debris. The media was concentrated 10-20× using 10-30 MWCO centriprep columns according to the manufacturer's instructions (EMD Millipore, Billerica, Mass.) before aliquoting and storing at −80° C.

Example B-2: Human LOXL2 CCM Assay

LOXL2 amine oxidase activity was evaluated by measuring Amplex Red fluorescence using 10-20× concentrated conditioned media (non BSA-containing) from CHO cells stably expressing human LOXL2. To assay for amine oxidase activity, 10 µL of the concentrated conditioned media was incubated with 2 µL of test compound in DMSO and 73 µL Assay Buffer (50 mM Borate Buffer, pH8) for 2 h at 37° C. After the 2 h incubation, 5 µL of 10 mM 1,5-Diaminopentane (DAP) diluted in Assay Buffer and 10 µL of Amplex Red Mix (8.5 µL Assay Buffer+0.5 µL of 10 mM Amplex Red+1 µL of 500 U/ml Horseradish Peroxidase) were added and the plate mixed and immediately placed on the FlexStation for fluorescence measurements. Fluorescence was read in kinetic mode every 2 min for 0.5-1 hour at excitation=544 and emission=590. The amine oxidase activity was calculated from the slope of the linear portion of the curve. Wells containing vehicle (DMSO) represented maximum activity and were set to 0% inhibition and wells containing 100 µM βAPN (3-aminopropionitrile) represented no activity and were set to 100% inhibition.

TABLE 23

| Compound | IC$_{50}$ |
|---|---|
| Rac-1 | A |
| Ent-1 | A |
| 1 | A |
| 2 | A |

A is <300 nM.

The examples and embodiments described herein are for illustrative purposes only and various modifications or changes suggested to persons skilled in the art are to be included within the spirit and purview of this application and scope of the appended claims.

What is claimed is:

1. A pharmaceutical composition comprising (R,R)-trans-(3-((4-(aminomethyl)-6-(trifluoromethyl)pyridin-2-yl)oxy)phenyl)(3-fluoro-4-hydroxypyrrolidin-1-yl)methanone, methanesulfonate salt (Compound 2) having the following structure:

Compound 2

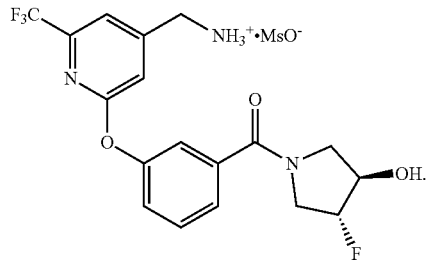

wherein:
a) Compound 2 is crystalline and has an X-ray powder diffraction (XRPD) pattern with characteristic peaks at 13.6° 2-Theta, 16.9° 2-Theta, 19.4° 2-Theta, 20.1° 2-Theta, 20.3° 2-Theta, 20.6° 2-Theta, 23.1° 2-Theta, and 23.6° 2-Theta; or an X-ray powder diffraction (XRPD) pattern substantially the same as shown in FIG. 1; or
b) Compound 2 is crystalline and has an X-ray powder diffraction (XRPD) pattern with characteristic peaks at 2.6° 2-Theta, 3.2° 2-Theta, 6.3° 2-Theta, 9.4° 2-Theta, 15.7° 2-Theta, and 22.1° 2-Theta; or an X-ray powder diffraction (XRPD) pattern substantially the same as shown in FIG. 3; or
c) Compound 2 is crystalline and has an X-ray powder diffraction (XRPD) pattern with characteristic peaks at 2.9° 2-Theta, 3.2° 2-Theta, 3.3° 2-Theta, 15.8° 2-Theta, 16.9° 2-Theta, and 20.2° 2-Theta; or an X-ray powder diffraction (XRPD) pattern substantially the same as shown in FIG. 5; or
d) Compound 2 is crystalline and has an X-ray powder diffraction (XRPD) pattern with characteristic peaks at 13.9° 2-Theta, 16.6° 2-Theta, 18.8° 2-Theta, 19.1° 2-Theta, 19.7° 2-Theta, 19.9° 2-Theta, 20° 2-Theta, 21.2° 2-Theta, 22.3° 2-Theta, 22.7° 2-Theta, 23.4° 2-Theta, and 23.8° 2-Theta; or an X-ray powder diffraction (XRPD) pattern substantially the same as shown in FIG. 7.

2. The pharmaceutical composition of claim 1, wherein the pharmaceutical composition is in the form of a solid form pharmaceutical composition.

3. The pharmaceutical composition of claim 1, wherein the pharmaceutical composition is in the form of a tablet, a pill, or a capsule.

4. The pharmaceutical composition of claim 1, wherein the pharmaceutical composition comprises about 1 mg to about 2000 mg of (R,R)-trans-(3-((4-(Aminomethyl)-6-(trifluoromethyl)pyridin-2-yl)oxy)phenyl)(3-fluoro-4-hydroxypyrrolidin-1-yl)methanone.

5. The pharmaceutical composition of claim 1, wherein the pharmaceutical composition is in the form of a tablet and comprises about 50 mg or about 250 mg of (R,R)-trans-(3-((4-(Aminomethyl)-6-(trifluoromethyl)pyridin-2-yl)oxy)phenyl)(3-fluoro-4-hydroxypyrrolidin-1-yl)methanone per tablet.

* * * * *